United States Patent
Buckland et al.

(10) Patent No.: US 11,338,296 B2
(45) Date of Patent: May 24, 2022

(54) VARIABLE TEMPERATURE REACTOR, HEATER AND CONTROL CIRCUIT FOR THE SAME

(71) Applicant: LEX Diagnostics Ltd., Royston (GB)

(72) Inventors: Justin Buckland, Royston (GB); Tom Jellicoe, Royston (GB); Alex Stokoe, Royston (GB); Amaru Araya-Williams, Royston (GB)

(73) Assignee: Lex Diagnostics Ltd., Hertfordshire (GB)

( * ) Notice: Subject to any disclaimer, the term of this patent is extended or adjusted under 35 U.S.C. 154(b) by 0 days.

(21) Appl. No.: 17/324,457

(22) Filed: May 19, 2021

(65) Prior Publication Data

US 2021/0276016 A1 Sep. 9, 2021

Related U.S. Application Data

(63) Continuation of application No. 14/124,001, filed on Dec. 16, 2020, now abandoned, which is a continuation-in-part of application No. PCT/GB2019/052100, filed on Jul. 26, 2019.

(51) Int. Cl.
  *B01L 7/00* (2006.01)
  *B01L 3/00* (2006.01)
  (Continued)

(52) U.S. Cl.
  CPC .............. *B01L 7/52* (2013.01); *B01L 3/5027* (2013.01); *C12Q 1/6806* (2013.01); *C12Q 1/686* (2013.01);
  (Continued)

(58) Field of Classification Search
  None
  See application file for complete search history.

(56) References Cited

U.S. PATENT DOCUMENTS 5,210,015 A   5/1993   Gelfand et al.
5,561,058 A   10/1996  Gelfand et al.
(Continued)

FOREIGN PATENT DOCUMENTS

AU   2012161566   3/1992
AU   199734812    1/1998
(Continued)

OTHER PUBLICATIONS

Farrar, J.S. and Wittwer, C.T. (2015). Extreme PCR: Efficient and Specific DNA Amplification in 15-60 Seconds. Clinical Chemistry, 61:1, 145-153.
(Continued)

*Primary Examiner* — William H. Beisner
(74) *Attorney, Agent, or Firm* — Fish & Richardson P.C.

(57) ABSTRACT

There is described a variable-temperature reactor for hosting a predetermined reaction therein. The reactor comprises a reaction cell, a heater, and a heat sink. The reaction cell has a reaction volume with thickness $H_v$ and width $W_v$ where $W_v > 4H_v$ and is defined by faces with one of the larger area faces of the reaction volume being bounded by an outer wall with thickness $H_w$. The heater is in contact with the said outer wall. The heater comprises a heat-generating heater element located on the face closer to the reaction volume and a heater support on the opposite face. The heater support is in contact with a heat sink, such that the heater support provides a thermal resistance $R_T$ between the heater element and the heat sink. The reactor, when filled with reagents having thermal diffusion coefficient $D_v$, has a diffusion time $t_v$, in the thickness direction, $t_v = H_v^2/D_v$. $t_v$ is less than the reaction time constant $t_R$. The outer wall has a thermal diffusion coefficient $D_w$ and has a thermal diffusion time $t_w = H_w^2/D_w < t_v$.

24 Claims, 50 Drawing Sheets

(51) Int. Cl.
   *C12Q 1/6806* (2018.01)
   *C12Q 1/686* (2018.01)
(52) U.S. Cl.
   CPC ............... *B01L 2300/0883* (2013.01); *B01L 2300/1827* (2013.01); *B01L 2300/1883* (2013.01)

(56) References Cited

U.S. PATENT DOCUMENTS

| | | |
|---|---|---|
| 5,624,833 A | 4/1997 | Gelfand et al. |
| 5,674,738 A | 10/1997 | Abramson et al. |
| 6,020,130 A | 2/2000 | Gold et al. |
| RE42,325 E | 5/2011 | Wittwer et al. |
| 8,455,190 B2 | 6/2013 | Makrigiorgos |
| 9,415,392 B2 | 8/2016 | Ismagilov et al. |
| 2002/0022261 A1 | 2/2002 | Anderson et al. |
| 2002/0028452 A1 | 3/2002 | Wittwer et al. |
| 2002/0119465 A1 | 8/2002 | Zhao et al. |
| 2002/0142300 A1 | 10/2002 | Bernard et al. |
| 2002/0168671 A1 | 11/2002 | Burns et al. |
| 2003/0008286 A1 | 1/2003 | Zou et al. |
| 2003/0017482 A1 | 1/2003 | Godfrey et al. |
| 2003/0165867 A1 | 9/2003 | Eyre et al. |
| 2004/0096964 A1 | 5/2004 | Mastromatteo et al. |
| 2004/0206749 A1 | 10/2004 | Villa et al. |
| 2004/0214315 A1* | 10/2004 | Saluz .............. B01L 7/52 435/303.1 |
| 2004/0227529 A1 | 11/2004 | Brooks et al. |
| 2005/0002835 A1 | 1/2005 | Shaw et al. |
| 2005/0006372 A1 | 1/2005 | Murakami et al. |
| 2005/0009101 A1 | 1/2005 | Blackburn |
| 2005/0019902 A1 | 1/2005 | Mathies et al. |
| 2005/0255499 A1 | 11/2005 | Gelfand et al. |
| 2006/0110763 A1 | 5/2006 | Kopp |
| 2006/0191887 A1 | 8/2006 | Baer et al. |
| 2008/0248535 A1 | 10/2008 | Ankenbauer et al. |
| 2009/0111149 A1 | 4/2009 | Cao |
| 2009/0269766 A1 | 10/2009 | Heindl et al. |
| 2009/0317806 A1 | 12/2009 | Hasson |
| 2009/0317874 A1 | 12/2009 | Dale et al. |
| 2010/0086991 A1 | 4/2010 | Fish |
| 2010/0104485 A1 | 4/2010 | Yuan |
| 2010/0191482 A1 | 7/2010 | Hasson et al. |
| 2010/0311070 A1 | 12/2010 | Oh et al. |
| 2011/0014605 A1 | 1/2011 | Stone |
| 2011/0048547 A1 | 3/2011 | Hasson et al. |
| 2011/0077897 A1 | 3/2011 | Hasson et al. |
| 2011/0091877 A1 | 4/2011 | Murphy et al. |
| 2012/0051390 A1 | 3/2012 | Coursey et al. |
| 2012/0264202 A1 | 10/2012 | Walker et al. |
| 2013/0171630 A1 | 7/2013 | Qin |
| 2013/0330818 A1 | 12/2013 | Koeda et al. |
| 2014/0045191 A1 | 2/2014 | DeJohn et al. |
| 2014/0199699 A1 | 7/2014 | Lee |
| 2014/0220668 A1 | 8/2014 | Tachibana et al. |
| 2015/0321195 A1 | 11/2015 | Malik et al. |
| 2016/0340632 A1 | 11/2016 | Breinlinger et al. |
| 2016/0377562 A1 | 12/2016 | Sundberg et al. |
| 2017/0239662 A1 | 8/2017 | Hwang |
| 2017/0342360 A1 | 11/2017 | Kim et al. |
| 2018/0154363 A1 | 6/2018 | Figley et al. |

FOREIGN PATENT DOCUMENTS

| | | |
|---|---|---|
| AU | 200022334 | 6/2000 |
| AU | 200135165 | 10/2001 |
| AU | 2006214085 A1 | 8/2006 |
| CA | 2922813 A1 | 3/2016 |
| CN | 101935697 | 1/2011 |
| DE | 202010013705 U1 | 12/2010 |
| EP | 0436644 | 4/1996 |
| EP | 0506889 B1 | 4/1997 |
| EP | 0919565 A2 | 6/1999 |
| EP | 0972848 A2 | 1/2000 |
| EP | 1033411 A2 | 9/2000 |
| EP | 1059523 A2 | 12/2000 |
| EP | 1362928 A2 | 11/2003 |
| EP | 0906449 B1 | 3/2004 |
| EP | 1897612 A1 | 3/2008 |
| EP | 1978109 A1 | 10/2008 |
| EP | 1778877 B1 | 10/2009 |
| EP | 2240610 B1 | 8/2012 |
| EP | 2064346 B1 | 11/2013 |
| EP | 2315848 B1 | 12/2014 |
| EP | 2582839 B1 | 5/2016 |
| EP | 2089542 B1 | 1/2017 |
| EP | 2598653 B1 | 8/2017 |
| EP | 1941035 B1 | 11/2017 |
| EP | 2710859 B1 | 9/2019 |
| EP | 2625286 B1 | 4/2020 |
| KR | 1020130128724 | 11/2013 |
| WO | 9408032 A1 | 4/1994 |
| WO | 9615270 A1 | 5/1996 |
| WO | 9711085 A1 | 3/1997 |
| WO | 9746707 A2 | 12/1997 |
| WO | 9804746 A1 | 2/1998 |
| WO | 0009651 A1 | 2/2000 |
| WO | 0018965 A1 | 4/2000 |
| WO | 0112854 A2 | 2/2001 |
| WO | 0214555 A2 | 2/2002 |
| WO | 0244339 A2 | 6/2002 |
| WO | 02070751 A1 | 9/2002 |
| WO | 03004991 A2 | 1/2003 |
| WO | 03006161 A1 | 1/2003 |
| WO | 03033722 A2 | 4/2003 |
| WO | 03091408 A2 | 11/2003 |
| WO | 2004038038 A2 | 5/2004 |
| WO | 2004065629 A1 | 8/2004 |
| WO | 2006034215 A2 | 3/2006 |
| WO | 2006089192 | 8/2006 |
| WO | 2006121423 A2 | 11/2006 |
| WO | 2007035806 A2 | 3/2007 |
| WO | 2007092643 A2 | 8/2007 |
| WO | 2008005241 A2 | 1/2008 |
| WO | 2008005321 A2 | 1/2008 |
| WO | 2008061129 A2 | 5/2008 |
| WO | 2008066869 A2 | 6/2008 |
| WO | 2009032087 A1 | 3/2009 |
| WO | 2009135093 A2 | 11/2009 |
| WO | 2010033338 A1 | 3/2010 |
| WO | 2010118427 A1 | 10/2010 |
| WO | 2010118430 A1 | 10/2010 |
| WO | 2010132813 A2 | 11/2010 |
| WO | 2011106724 A2 | 9/2011 |
| WO | 2011124918 A1 | 10/2011 |
| WO | 2011153385 A2 | 12/2011 |
| WO | 2012045668 A1 | 4/2012 |
| WO | 2012161566 A1 | 11/2012 |
| WO | 2013074627 A2 | 5/2013 |
| WO | 2013142364 A1 | 9/2013 |
| WO | 2013177429 A2 | 11/2013 |
| WO | 2014058919 A1 | 4/2014 |
| WO | 2014210199 A2 | 6/2014 |
| WO | 2014143228 A1 | 9/2014 |
| WO | 2014152544 A1 | 9/2014 |
| WO | 2015058104 A1 | 4/2015 |
| WO | 2015069743 A1 | 5/2015 |
| WO | WO-2015073689 A1 * | 5/2015 ............... B01L 7/52 |
| WO | 2015103320 A1 | 7/2015 |
| WO | 2017079636 A1 | 5/2017 |
| WO | 2017119902 A1 | 7/2017 |
| WO | 2017127570 A1 | 7/2017 |
| WO | 2018023118 A1 | 2/2018 |
| WO | 2018094091 A1 | 5/2018 |
| WO | 2019046860 A1 | 3/2019 |

OTHER PUBLICATIONS

Trauba, J.M. and Wittwer, C.T. (2017). Microfluidic Extreme PCR: <1 Minute DNA Amplification in a Thin Film Disposable. J. Biomedical Science and Engineering, 10, 219-231.

(56) References Cited

OTHER PUBLICATIONS

Hindson, B. J. (2011). High-Throughput Droplet Digital PCR System for Absolute Quantitation of DNA Copy Number. Anal. Chem., 83, 8604-8610.
Chakrabarti, M. C. and Schwarz, F. P. (1999). Thermal stability of PNA/DNA and DNA/DNA duplexes by differential scanning calorimetry. Nucleic Acids Research, 24, 4801-4806.
PCT Patent Application PCT/GB2019/052100 International Search Report and Written Opinion dated Oct. 18, 2019.
Marin, E., "Characteristic dimensions for heat transfer," Lat. Am. J. Phys. Educ., 1, 56-60, 2010.
Lukacs, G.L. et al., "Size-dependent DNA mobility in cytoplasm and nucleus," J Biol Chem. 275(3):1625-9, 2000.
Kulin'ski, T et al.,"Comparative calorimetric studies on the dynamic conformation of plant 5S rRNA: 11 structural interpretation of the thermal unfolding patterns for lupin seeds and wheat germ," Nucleic Acids Research, vol. 19, No. 9, Apr. 11, 1991.
Barciszewski, J. et al., "Comparative calorimetric studies on the dynamic conformation of plant 5S rRNA. I. Thermal unfolding pattern of lupin seeds and wheat germ 5S rRNAs, also in the presence of magnesium and sperminium cations," Nucleic Acids Research, vol. 16, No. 2, Dec. 3, 1987.
International Preliminary Report on Patentability in Appl. No. PCT/GB2019/052100, dated Jan. 26, 2021, 6 pages.

\* cited by examiner 600 outer guard heater 610 inner guard heater

VARIABLE TEMPERATURE REACTOR, HEATER AND CONTROL CIRCUIT FOR THE SAME

RELATED APPLICATIONS

This application is a continuation of U.S. patent application Ser. No. 17/124,001, filed Dec. 16, 2020, which is a continuation of PCT Patent Application No. PCT/GB2019/052100, filed Jul. 26, 2019, which claims priority to Great Britain Patent Application No. 1812192.1, filed Jul. 26, 2018, the disclosures of which are incorporated herein by reference.

BACKGROUND

The present invention relates a reactor for reactions where rapid adjustment of temperature is required. It also relates to a heater and driving and sensing circuit for the same as well as a corresponding method of operating the reactor.

One example process where such a reactor is required is DNA amplification by the polymerase chain reaction (PCR), where the reactor is suitable for fast thermocycling to reduce the time for completion of PCR. Another example is DNA sequencing by synthesis where base addition can optimised by adjusting the temperature for each step of a multi-step reaction.

The reactor of the invention is also suitable for monitoring of the progress of PCR by the calorimetric detection of oligonucleotides in solution. The reactor is also suitable for digital PCR or multiplexed PCR to provide independent analysis of sub-samples at multiple locations within a continuously connected liquid sample.

The invention also relates to a heater for rapid adjustment of temperature of a reaction volume and with a high degree of temperature uniformity and with precise temperature control.

The invention also relates to a device for differential scanning calorimetry (DSC) or differential thermal analysis (DTA) using sample and reference heaters configured in a Wheatstone bridge circuit.

PCR requires repeated temperature cycling between temperatures of approximately 60° C. and 95° C. Conventionally heating and cooling are carried out using a Peltier element to drive heat from a heat sink into a sample when increased temperature is required, or to drive heat from the sample to a heat sink when decreased temperature is required. The heat sink is often cooled with a fan.

This approach has many disadvantages: the apparatus required is large and has high power consumption. The heat capacity of the part of the apparatus that changes temperature during a thermal cycle is significantly larger than the heat capacity of the sample, resulting in increased energy use and slower thermal cycling. Temperature ramp rates are limited and the thermal cycling time is increased by long thermal diffusion times through the Peltier element and parts used to make thermal contact with and contain the sample, and through the sample itself. These factors result in slow and energy-inefficient PCR thermocycling.

Conventionally a temperature sensor remote from the Peltier and sample is used to control the thermocycler. Inevitably there is a lag in the thermal response of the temperature sensor, compared with the Peltier, and this complicates the thermal control of the system. A tuned PID algorithm is often used to maximise temperature ramp rates and minimise overshoot, but this can be complex to develop and implement, and may fail to provide the intended time-temperature profile within the sample.

A further disadvantage is that the lifetime of the Peltier element is limited, due to mechanical stresses resulting from repeated thermal cycling.

These disadvantages apply to other reactions requiring precise temperature control and rapid temperature changes.

An alternative prior art approach to thermocycling is to move the sample between fixed temperature water baths or heaters. Three examples are shown in FIGS. 1-3. In FIG. 1, a sample is transferred between water baths and in FIG. 2 a sample is transferred between heater blocks. These solutions have high mechanical complexity and large space requirements due to the moving parts. In FIG. 3 the sample is passed through a microfluidic chip containing a serpentine path passing over two heater blocks, with the disadvantage that the sample is exposed to a large surface area of microfluidic channel. This gives two disadvantages: the sample and reagents may adhere to the channel walls, decreasing sensitivity, increasing sample volume requirement and increasing reagent costs, and the size and cost of the microfluidic chip is increased.

The large size and surface area of the long serpentine channel shown in FIG. 3 is due to the requirement for the channel to pass between two different temperature zones which are spatially separated, typically by a distance of >1 mm. Furthermore, the sample volume is smaller than the internal volume of the serpentine channel, increasing the ratio of channel surface area to sample volume.

It is desirable to carry out thermal cycling at a speed fast enough that the time required for temperature changes does not account for the majority of the total time for thermocycling. The total time for thermocycling is the sum of the time for temperature changes and the time for reactions, and the slowest part of the PCR reaction is the extension phase, which requires approximately 1 s or more for a typical sequence length of 100 base pairs. Therefore we target a time of <1 s for temperature ramping. The target temperatures for PCR are typically between 60° C. and 95° C. so we need temperature ramp rates of 70° C./s or more for heating and cooling to achieve to reduce the temperature change time to 1 s. Much higher temperature ramp rates (200° C./s or higher) offer limited speed advantage as the total time required will be dominated by the reaction time and not the time required for temperature changes.

In this invention we disclose a reactor for carrying out fast thermocycling at approximately 100° C./s without the disadvantages of mechanical movement systems or long serpentine channels. It is possible to contain the sample in a wide channel reduce the surface area of the side walls, compared to the case of a serpentine channel. When using a wide channel, it may be necessary to introduce internal support structures such as ribs or pillars to avoid large unsupported spans to and increase the mechanical strength of a fluidic channel.

Additionally, in this invention we disclose a reactor which includes a serpentine channel. Although some serpentine channels have disadvantages as explained above, in an alternative approach, it is possible to contain the sample in a shorter serpentine channel located over a single heater capable of variation of temperature over time. In this case, the sample does not flow between different temperature zones during amplification; instead the heater temperature varies over time. This allows the serpentine channel length to be reduced and the channel internal volume can be equal to the sample volume, reducing the ratio of channel surface area to sample volume. A further benefit is that this configuration is more convenient for quantitative PCR experiments, in which the concentration of amplified DNA can be monitored over time at a single location, for example by using fluorescent probes or intercalating dyes.

The reactor contains three main elements: a reaction cell which contains a volume to be temperature-controlled, a heat sink to absorb heat, and a heater in thermal contact with the reaction cell and the heat sink. The heater has a heat-generating heater element on the face contacting the reaction cell and a heater support on the face contacting the heat sink. The thermal resistance of the heater support is chosen to give a low thermal cycle time for a given set of target reaction temperatures, heat sink temperature and power requirement.

In one aspect, the present invention provides a variable-temperature reactor for hosting a predetermined reaction therein, the reactor comprising a reaction cell, a heater, and a heat sink, wherein the reaction cell has a reaction volume with thickness $H_V$ and width $W_V$ where $W_V > 4 H_V$ and is defined by faces with one of the larger area faces of the reaction volume being bounded by an outer wall with thickness $H_W$;

wherein the heater is in contact with the said outer wall, where the heater comprises a heat-generating heater element located on the face closer to the reaction volume and a heater support on the opposite face, the heater support being in contact with a heat sink, such that the heater support provides a thermal resistance $R_T$ between the heater element and the heat sink, where the reactor, when filled with reagents having thermal diffusion coefficient $D_V$ has a diffusion time $t_V$, in the thickness direction, $t_V = H_V^2 / D_V$ and in $t_V$ is less than the reaction time constant $t_R$, and wherein the outer wall has a thermal diffusion coefficient $D_W$ and has a thermal diffusion time $t_W = H_W^2 / D_W \lesssim t_V$.

Preferably, the heater element functions both as a heater and as a temperature sensor.

Preferably, the reactor further comprises a controller, wherein the heater is connected to the controller and is controlled by the controller to vary the temperature of the reactor between a higher temperature $T_{High}$ and a lower temperature $T_{Low}$, both temperatures being above the temperature of the heat sink $T_{Sink}$.

Preferably, the reaction volume thickness, $H_V$, is less than 250 microns.

Preferably, the reaction cell contains a reaction volume with width $W_V$ and length $L_V$ formed by a serpentine channel located within an area having width $W_V$ and length $L_V$.

Preferably, the reaction volume is bounded on both of its large area faces by outer walls with thickness $H_W$, with heaters in contact with both said outer walls, and with heat sinks in contact with both heaters.

Preferably, the heater element is a resistive heating element.

Preferably, the heater element is fabricated from an electrically conductive material and the heater support is fabricated from an electrically insulating material.

Preferably, the heater is separable from the heat sink.

Preferably, the reactor is arranged such that the thermal resistance $R_T$ between the heater element and the heat sink is chosen to satisfy the following relationships:

$$R_T > (T_{HIGH} - T_{Sink}) / p_{Heat} \text{ and}$$

$$0.5 R_{T,Opt} < R_T < 2 R_{T,Opt}$$

where $R_{T,Opt} = (T_{HIGH} + T_{LOW} - 2 T_{Sink}) / p_{Heat}$, and the reactor is arranged to cycle repeatedly between a lower temperature $T_{LOW}$ and a higher temperature $T_{HIGH}$ using a heater with power output $p_{Heat}$ and a heat sink at a temperature $T_{Sink}$.

Preferably, the reactor is arranged such that the thermal resistance of the heater support $R_T$ and the sum of the heat capacity of the filled reaction volume and the heat capacity of the part of the thin outer wall located between the reaction volume and the heater element, $C_V$ satisfy the relationship $R_T C_V < t_R$, where $t_R$ is the time constant for the reaction.

Preferably, the reactor is arranged such that the sum of the heat capacity of the filled reaction volume and the heat capacity of the part of the thin outer wall located between the reaction volume and the heater element, $C_V$, and the heat capacity of the heat sink, $C_S$, satisfy the relationship: $C_S / C_V > 100$.

Preferably, the thermal conductivity of the heat sink material is more than 10 times the thermal conductivity of the heater support material.

Preferably, the heat capacity of the part of the thin outer wall and heater located between the reaction volume and the heat sink is lower than the heat capacity of liquid within the reaction volume.

Preferably, the thermal effusivity of the heat sink material is more than 10 times the thermal effusivity of the heater support material, where thermal effusivity e is a function of the material's thermal conductivity k, density ρ and specific heat capacity $c_p$ and is defined as $e = \sqrt{k \rho c_p}$.

Preferably, the heater element extends across the full area of the reaction volume.

Preferably, the heater element is resistive and has a rectangular or square shape.

Preferably, the heater element is fabricated from an electrically conductive material with absolute value of temperature coefficient of resistance greater than 500 ppm/K, preferably greater than 2,500 ppm/K, and more preferably greater than 10,00 ppm/K, across the operating temperature range of the heater.

Preferably, the heater comprises Kelvin contacts for electrical resistance measurements.

Preferably, the heater element is arranged to have higher heat output per unit area near its perimeter than near its centre.

Preferably, the heater element comprises a main heater surrounded by one or more guard heaters.

Preferably, the main heater is elongate in the direction of current flow and where guard heaters are placed adjacent to the long sides of the main heater.

Preferably, the sheet resistance of the heater element is locally increased in end zones located on the heater element edges perpendicular to the direction of current flow.

Preferably, the reaction volume is arranged to contain, in use, reagents used for polymerase chain reaction (PCR) amplification of nucleic acid sequences.

Preferably, the reactor is configured to carry out DNA amplification by polymerase chain reaction (PCR) thermocycling.

BRIEF DESCRIPTION OF THE DRAWINGS

Examples of the present invention will now be described with reference to the accompanying drawings, in which.

DETAILED DESCRIPTION

Figure 1A:
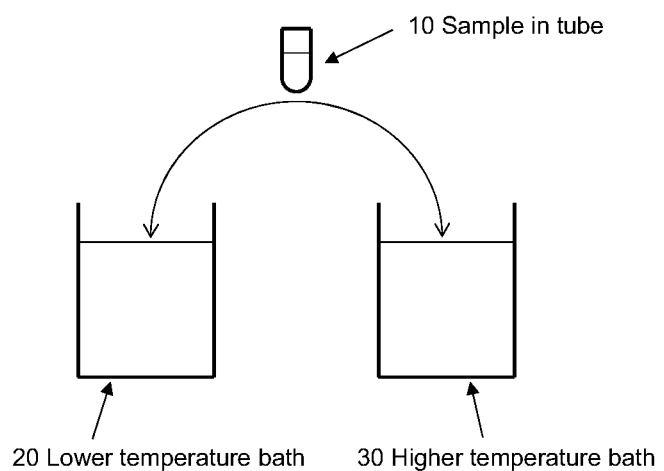
FIGS. 1A and 1B (prior art) show thermal cycling by moving a sample between water baths held at different temperatures.
Figure 1B:
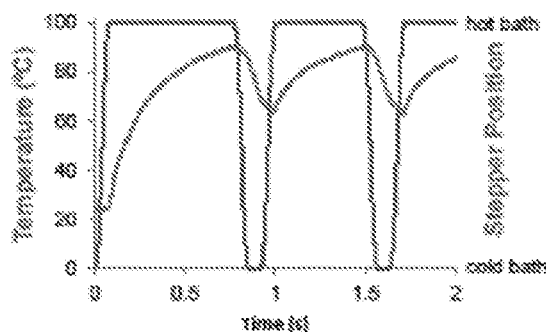

FIG. 1A-B (prior art) shows thermal cycling by moving a sample between water baths held at different temperatures. The apparatus is shown in schematic form (A). The sample temperature and position are plotted against time in (B). Reference: Farrar, J. S. and Wittwer, C. T. (2015) Extreme PCR: Efficient and Specific DNA Amplification in 15-60 Seconds. Clinical Chemistry, 61:1145-153.

Figure 2:
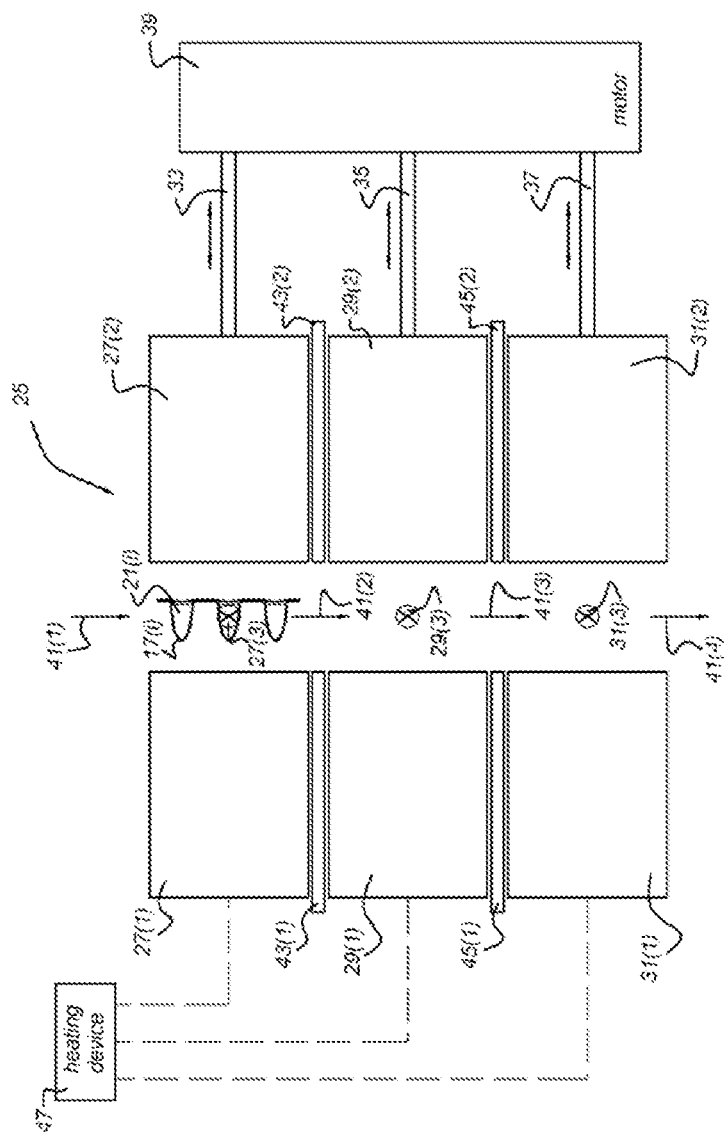
FIG. 2 (prior art) shows thermal cycling by moving a sample between heater blocks held at different temperatures.

FIG. 2 (prior art) shows thermal cycling by moving a sample between heater blocks held at different temperatures. Reference: WO2012161566.

Figure 3:
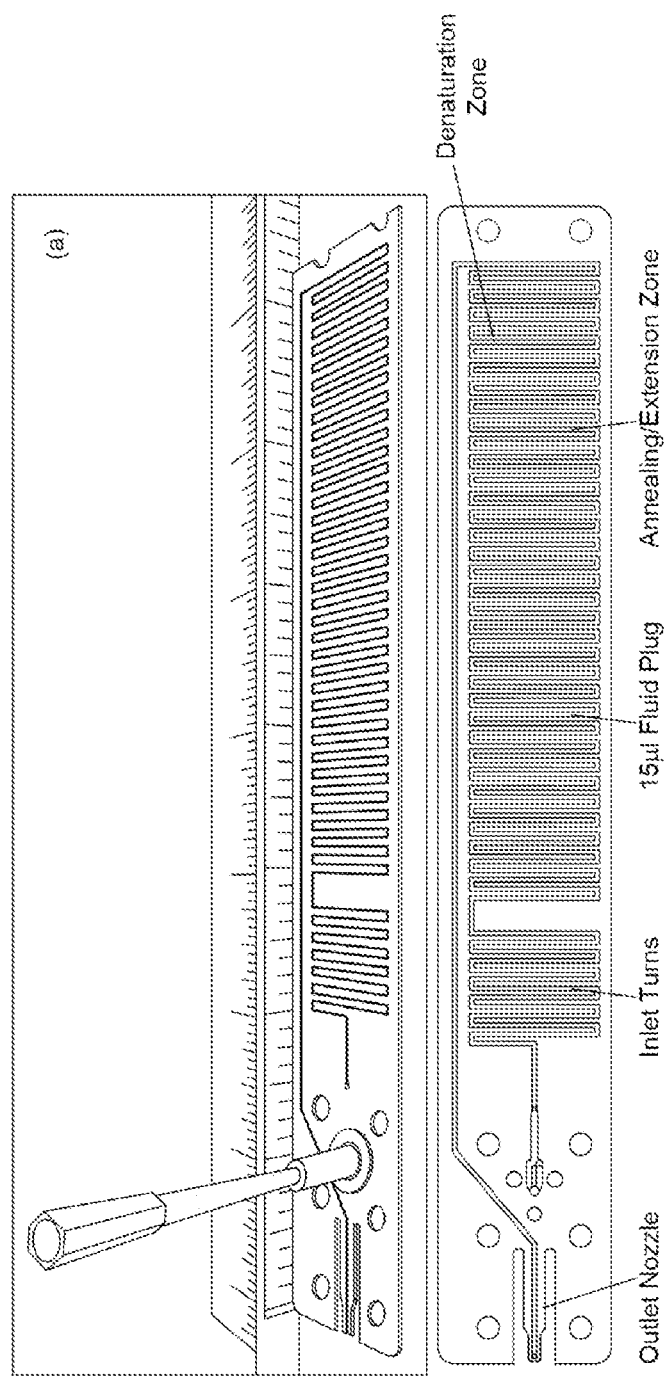
FIG. 3 (prior art) shows thermal cycling by passing a sample through a serpentine path that passes alternately over higher and lower temperature zones.

FIG. 3 (prior art) shows thermal cycling by passing a sample through a serpentine path that passes alternately over higher and lower temperature zones. Reference: Trauba, J. M. and Wittwer, C. T. (2017) Microfluidic Extreme PCR: <1 Minute DNA Amplification in a Thin Film Disposable. J. Biomedical Science and Engineering, 10, 219-231.

Figure 4:
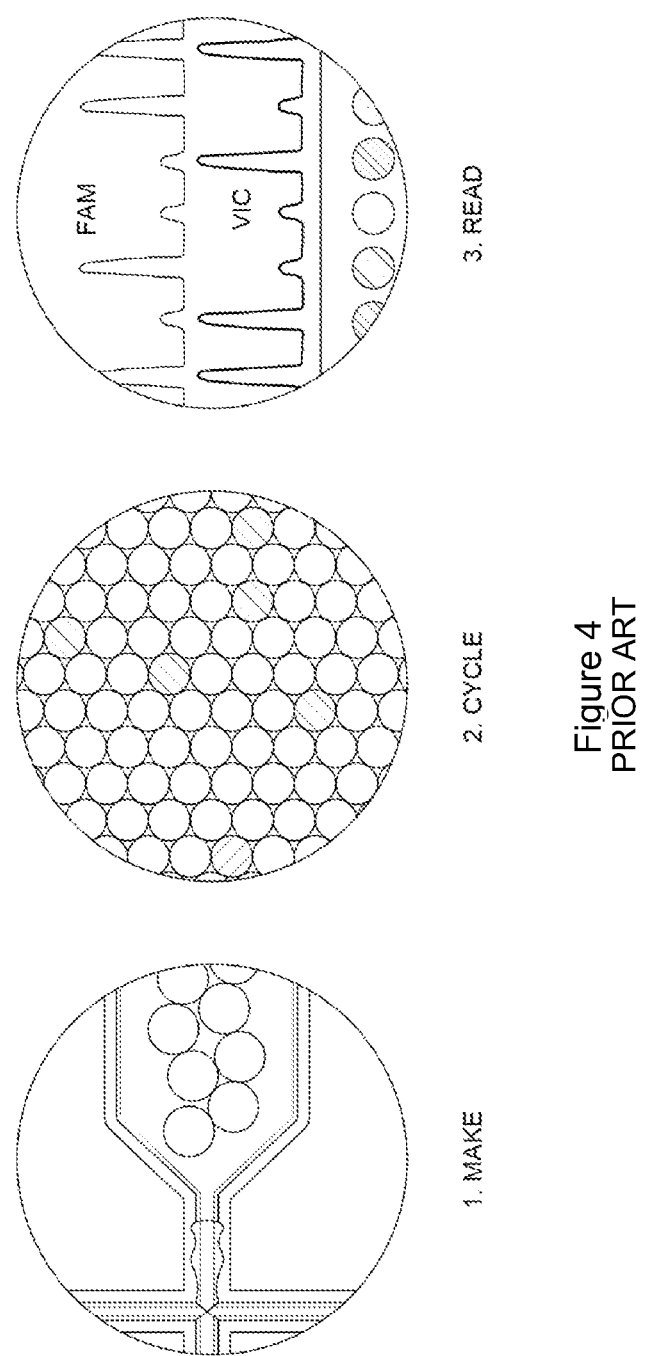
FIG. 4 (prior art) shows digital PCR by creating droplets of the sample contained in an immiscible liquid, usually a fluorinated oil.

FIG. 4 (prior art) shows digital PCR by creating droplets of the sample contained in an immiscible liquid, usually a fluorinated oil. Reference: Hindson, B. J. (2011) High-Throughput Droplet Digital PCR System for Absolute Quantitation of DNA Copy Number. Anal. Chem., 83, 8604-8610.

Figure 5:
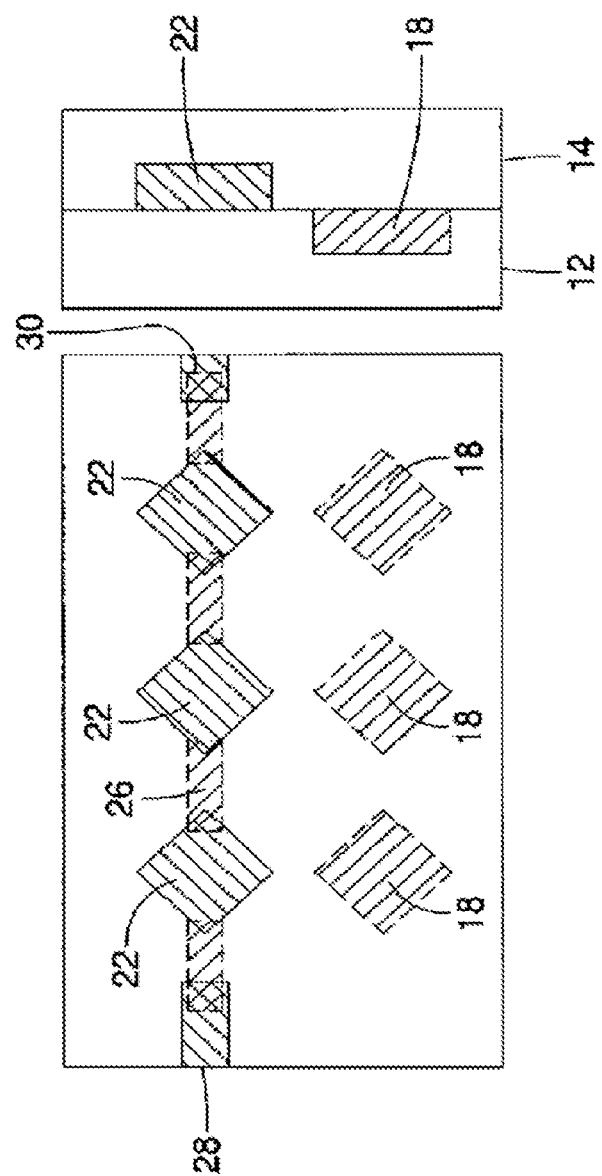
FIG. 5 (prior art) shows a top view and a side view of a slip chip device.
Figure 6A:
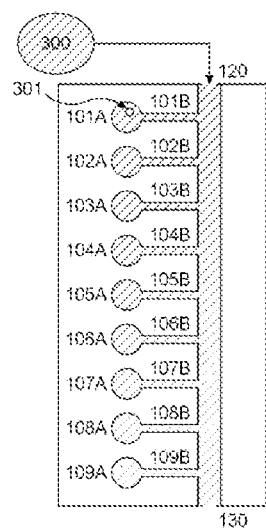
FIGS. 6A, 6B, 6C and 6D (prior art) show digitisation for digital PCR by filling first with the sample liquid and then with a gas which can pass through a gas-permeable barrier and which divides the sample into disconnected volumes.
Figure 6B:
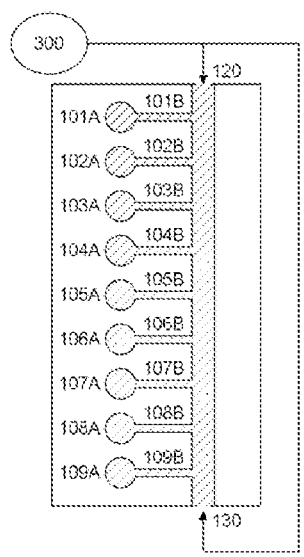
Figure 6C:
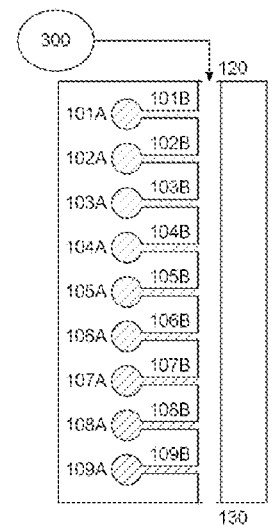
Figure 6D:
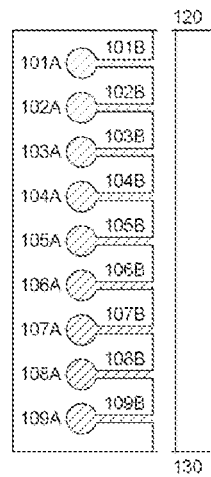

FIG. 5 (prior art) shows a top view and a side view of a slip chip device. The slip chip uses relative motion of two parts to create isolated sub-samples for digital or multiplexed PCR. Reference: U.S. Pat. No. 9,415,392 B2.

FIG. 6A-D (prior art) shows digitisation for digital PCR by filling first with the sample liquid and then with a gas which can pass through a gas-permeable barrier and which divides the sample into disconnected volumes. Reference: WO 2018094091.

Figure 7:
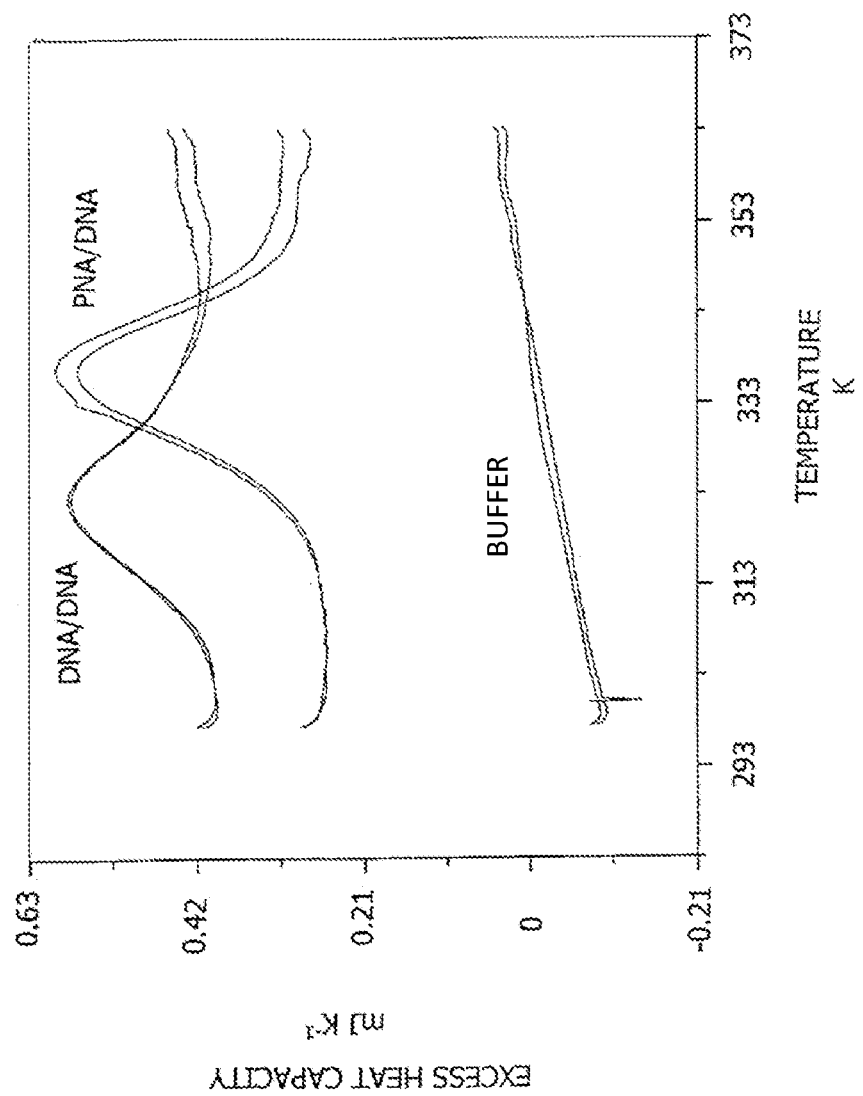
FIG. 7 (prior art) shows two repeat DSC scans of a 0.0244 mM PNA(TG)/DNA duplex solution, a 0.0303 mM DNA (TG)/DNA duplex solution, and the buffer solution.

FIG. 7 (prior art) shows two repeat DSC scans of a 0.0244 mM PNA(TG)/DNA duplex solution, a 0.0303 mM DNA (TG)/DNA duplex solution, and the buffer solution. The temperature scan rate was 60K/h and the cell volume was 0.511 ml. Reference: Chakrabarti, M. C. and Schwarz, F. P. (1999) Thermal stability of PNA/DNA and DNA/DNA duplexes by differential scanning calorimetry. Nucleic Acids Research, 24, 4801-4806.

For reactions of the type for which the invention is employed, thermal cycling requires the thermal diffusion time between the heater and sample to be small compared with the target cycle time. Thermal diffusion time t is given by:

$$t = R^2/D_T,$$

where R is the characteristic length scale and $D_T$ is the thermal diffusivity of the material. Table 1 below shows an example reactor design, which will be described below, in which the thermal diffusion times of the reaction volume and thin outer wall are both less than the reaction time for PCR which we take as approximately 1 s for a 100 base pair sequence.

In order to heat efficiently, it is desirable to minimise the ratio of the heat capacity of the reaction cell materials and heater relative to the heat capacity of the sample. The heat capacity of the reaction volume should be a large fraction of the sum of the reaction cell and heater heat capacities, preferably >10% and more preferably >50%.

In order to heat the reaction volume, the heater element is switched on and heat generated by the heater element flows into the reaction volume and into the heat sink. In order to cool the reaction volume, the heater element is switched off and heat flows from the reaction volume through the heater and into the heat sink. The heat capacity of the heat sink is chosen to be much larger than the combined heat capacity of the reaction cell and heater, in order to limit the heat sink temperature rise over the series of thermal cycles needed to complete a reaction. In the example given below, the heat sink heat capacity is >100 times that of the combined heat capacity of the heater and reaction cell. In order to further limit the temperature rise of the heat sink, the heat sink can be cooled continuously, for example by natural or forced convection, liquid circulation, spray cooling, or connection to a heat pipe or a Peltier device.

The thermal resistance of the heater support $R_T$ can be optimised to minimise the thermal cycling time for a given temperature profile and heatsink temperature $T_{Sink}$ and heater element power $p_{Heat}$. The time required for thermal cycling between a $T_{LOW}$ and $T_{HIGH}$ is minimised when the heating time is equal to the cooling time and this condition is satisfied when $R_T = R_{T, Opt}$ as follows:

$$R_{T,Opt} = (T_{HIGH} + T_{LOW} - 2T_{Sink})/p_{Heat}.$$

We define the axial direction to be perpendicular to the contact surface between the heater and the reaction cell and a lateral direction to be in the plane of the contact surface between the heater and the reaction cell. It is desirable to limit lateral heat flow as lateral heat flow implies temperature gradients and temperature nonuniformity within the reaction cell, reducing the precision of temperature control.

In order to limit lateral heat flow, the reaction volume is chosen to have a ratio of height $H_V$ (in the axial direction) to width $W_V$ (in the lateral direction) such that the side area is smaller than the area of the face nearest the heater element. This condition is satisfied for a square or circular reaction volume as follows:

$$W_V > 4H_V.$$

In order to further limit lateral heat flow, the heater element may be designed to have higher heat output near its edges and to extend beyond the reaction volume. The higher heat output of the heater element near its edges can compensate for lateral heat flow and provide more uniform temperature conditions across the reaction volume.

An electrical heater element may have a square or rectangular shaped heat-generating area with electrical terminals on two opposite sides of the heat-generating area and a direction of current flow from one terminal to the other. One approach to improving the temperature uniformity of such a heater element is to increase the sheet resistance of the heater element near the sides of the electrical terminals so that the heat output per unit area is increased locally near these sides, relative to the heat output near the centre of the heater element. To further improve temperature uniformity, it is also desirable to increase the heat output of the heater element along the sides parallel to the direction of current flow. This can be done by locally reducing the sheet resistance near these sides so that the current density is increased near these sides and the heat output per unit area is increased, relative to the heat output near the centre of the heater element.

The resistance of the heater element can be increased locally by reducing the thickness of the material or by patterning the material with holes or slots or material variation which has the effect of increasing the length of the electrical conduction path and reducing the cross-section area of the electrical conduction path. These hole or slot features must be small compared with the thickness of the reaction volume so that they do not disturb the temperature uniformity within the reaction volume.

Guard heaters can be used to further limit lateral heat flow at the edges of the heater. Guard heaters are additional heaters located near the edge of a heater element and driven to maintain a temperature close to the target temperature of the main heater element. The heat output per unit are of the guard heater is higher than that of the main heater element, to compensate for lateral heat loss. The guard heater may be operated with closed loop control with the same temperature setpoint as the main heater element or the guard heater may be operated with the same controller or on/off timing as the main heater element but with a different drive voltage which can be adjusted to optimise the temperature uniformity at a specific temperature setpoint.

The reactor can be configured as a single-sided cell or a double-sided cell. The single-side configuration has a reaction cell with one thin outer wall in contact with a heater which is in turn in contact with a heat sink. The double-sided configuration has a reaction cell with two thin outer walls in contact with heaters which are in turn in contact with heat sinks.

The reaction cell, heater and heat sink can have planar or curved forms. A planar form may be preferred for ease of construction and optical monitoring of the reaction. However other forms such as part-spherical or cylindrical are possible and these may have benefits in allowing tensioned flexible reaction cell and heater layers to make good thermal contact with each other and with the heat sink which is typically a rigid metal part.

TABLE 1

Example reactor materials, thermal properties and geometry. Single layer and double layer heater examples are given. The thermal properties of the sample contained in the reaction volume are assumed to be the same as for water.

| material | | Reaction cell | | Heater (double layer) | | Heater (single layer) | |
|---|---|---|---|---|---|---|---|
| | | reaction volume water | thin outer wall polypropylene | rigid layer glass | flexible layer thermal pad | flexible layer polyimide | Heat sink aluminium |
| thermal conductivity | W/m/K | 0.6 | 0.15 | 0.8 | 0.5 | 0.12 | 200 |
| specific heat capacity | J/K/kg | 4182 | 1920 | 753 | 1200 | 1090 | 897 |
| density | kg/m$^3$ | 1000 | 946 | 2700 | 1100 | 1420 | 2700 |
| thermal diffusivity | m$^2$/s | 1.4E−07 | 8.3E−08 | 3.9E−07 | 3.8E−07 | 7.8E−08 | 8.3E−05 |
| thermal effusivity | W · s$^{1/2}$/m$^2$/K | 1584 | 522 | 1275 | 812 | 431 | 22009 |
| volume | μl | 5 | 1.2 | 15 | 6.4 | 3.8 | 5000 |
| area | mm$^2$ | 50 | 50 | 50 | 50 | 50 | 500 |
| side (if square) | mm | 7.1 | 7.1 | 7.1 | 7.1 | 7.1 | 22.4 |
| thickness | mm | 0.1 | 0.024 | 0.3 | 0.127 | 0.076 | 10 |
| thermal diffusion time | s | 0.07 | 0.007 | 0.23 | 0.043 | 0.075 | 1.2 |
| thermal resistance | K/W | 3.3 | 3.2 | 7.5 | 5.1 | 12.7 | 0.10 |
| heat capacity | J/K | 0.021 | 0.0022 | 0.031 | 0.0084 | 0.0059 | 12.1 |

Thermal control of the heater element with a spatially separated temperature sensor introduces difficulties as there will be a time lag between temperature changes at the heater element and temperature changes at the temperature sensor. This time lag can cause problems such as overshoot or oscillation of the heater element temperature. To avoid these problems, the heater element may be configured as a temperature sensor where the resistance of the heater element is used to determine its temperature. The heater element may have a positive temperature coefficient of resistance (such as a metal) or a negative temperature coefficient of resistance (such as a metal oxide or other dielectric). In either case it is desirable that the magnitude of the temperature coefficient of resistance (TCR) of the heater element is large, preferably greater than 500 ppm/K, more preferably greater than 2,500 ppm/K and most preferably greater than 10,000 ppm/K.

The heater element may be provided with four-terminal Kelvin contacts to allow more precise measurement of the resistance of the heater element and more precise temperature measurement.

If the heater element material has a lower than desired sheet resistance then it may be patterned with slots or gaps perpendicular to the direction of current flow to increase the sheet resistance.

If the heater element has a higher than desired sheet resistance then it may be provided with interdigitated contact terminals to decrease the path length through the heater element and to increase the cross-sectional area for current flow.

It is desirable to monitor the state of a reaction while thermal cycling and at the end of a number of thermal cycles. In particular, PCR amplification of DNA can be detected using fluorescently labelled dyes, or electrochemically active labels. These methods respectively have disadvantages of: requirement for labels which may be costly or may inhibit the PCR amplification process, requirements for complex optical instrumentation and optical interface with the sample, and requirements for electrochemical interface with the sample.

This invention provides calorimetric detection of amplified DNA by detecting the heat of melting during the heating phase of the thermal cycle, which leads to an increased heat capacity at the melting temperature. This allows PCR amplification to be monitored continuously in a label-free manner with minimal additional instrumentation hardware.

The format of the reactor of the current invention is well suited to scanning calorimetric detection because the design allows rapid temperature ramp rates and because the heat capacity of the sample contained in the reaction volume is a significant fraction of the total heat capacity of the heater, reaction cell and sample. These factors increase the strength of the calorimetric signal and improve the sensitivity of calorimetric detection.

In order to detect the presence of DNA by an increase in heat capacity at the DNA melting temperature, a differential thermal analysis (DTA) method can be used, in which the temperature difference between a sample and reference cell is measured as a function of temperature or time while the temperature is ramped through the melting point, with equal heat input to both sample and reference. The evolution of the differential temperature scan over the course of the reaction can be monitored to detect a change in the concentration of reaction products. An alternative method uses differential scanning calorimetry (DSC) in which the difference in heat flux input to a sample and reference cell is measured as a function of temperature or time while the temperatures of both sample and reference are ramped and held equal.

AC calorimetry can be combined with the current invention, using a pulsed or oscillating heater drive to increase the robustness and sensitivity of a calorimetric measurement. One example approach is to drive a resistive heater with a sinusoidal drive voltage at a drive frequency, generating oscillatory heat output at twice the drive frequency. The temperature of the heater element will also oscillate at twice the drive frequency, and the amplitude of this oscillation will depend on the heat capacity of the sample. The amplitude of temperature oscillation can be detected by measuring oscillations in the electrical resistance of the heater element when the heater is also configured to be a temperature sensor with non-zero temperature coefficient of resistance. The advantage of this approach is that the method is insensitive to slow DC drifts in heater resistance and synchronous detection of the temperature oscillation can be used to reject sources of external noise.

The optimum range of frequencies of heat input for AC calorimetry can be estimated by considering the penetration depth L of temperature oscillations produced by an oscillating heat source (reference: Marin, E. (2010) Characteristic dimensions for heat transfer Lat. Am. J. Phys. Educ., 1, 56-60).

$$L = \sqrt{\frac{2D_T}{\omega}}$$

$D_T$ is the thermal diffusivity of the material into which the heat diffuses and $\omega$ is the angular frequency of the heat source oscillation. It is preferable to choose conditions to give a penetration depth L equal to or smaller than the height of the reaction volume, $H_V$, for the case of a reactor with heater on one side only. A benefit of using a higher frequency oscillation and smaller penetration depth is that the calorimetric measurement is less sensitive to variations in $H_V$ and this reduces the sensitivity to differences between sample and reference reaction volume geometries.

The condition $L \leq H_V$ occurs for a sinusoidal electrical drive at frequency $f_{DRIVE}$ applied to a resistive heater element to generate an oscillating heat output at frequency $2 f_{DRIVE}$, where $f_{DRIVE}$ satisfies the condition:

$$f_{DRIVE} \geq \frac{1}{2\pi} \frac{D_V}{H_V^2}$$

For the case of a reactor with a heater on one side only and for a typical reaction volume according to the invention, height $H_V=100$ μm, thermal diffusivity for water $D_V=1.43 \times 10^{-7}$ m²/s, and $f_{DRIVE} \geq 2.3$ Hz.

For the case of a reactor with a heater on both sides, it is preferable that the penetration depth L be equal to or smaller than half the height of the reaction volume and for a typical reaction volume according to the invention, height $H_V=100$ μm, thermal diffusivity for water $D_V=1.43 \times 10^{-7}$ m²/s, and $f_{DRIVE} \geq 9.1$ Hz. In general, for a reactor with a heater on both sides, $f_{DRIVE}$ satisfies the condition:

$$f_{DRIVE} \geq \frac{4}{2\pi} \frac{D_V}{H_V^2}$$

It is also desirable that the penetration depth L be greater than or equal to the thickness $H_W$ of the thin outer wall in contact with the reaction volume. This gives the condition:

$$f_{DRIVE} \leq \frac{1}{2\pi} \frac{D_W}{H_W^2}$$

For a typical reaction volume according to the invention, wall thickness $H_W=24$ μm, thermal diffusivity for a polypropylene wall $D_W=8.26 \times 10^{-8}$ m²/s, and $f_{DRIVE} \leq 23$ Hz. Preferably, as referred to herein, a "volume" may also connote a "vessel" or "cell", which define a volume, and vice versa.

When using an AC calorimetric method, it is advantageous to measure the variations in heater resistance at a frequency of 2× the frequency of the AC electrical drive. Feeding a sinusoidal electric drive waveform at frequency $\omega$ into a heater element creates a temperature fluctuation on it at a frequency $2\omega$, and accordingly a resistance fluctuation at $2\omega$. This further leads to a voltage fluctuation at $3\omega$. Measurement of the voltage fluctuation at frequency of 3× the frequency of the AC electrical drive using the "3-ω" method allows narrow-band detection techniques to be used, giving an increased signal-to-noise ratio.

When a differential calorimetric method is used, it is advantageous to configure electrically resistive heater elements for the sample and reference reactions in a Wheatstone bridge circuit. This approach allows the difference between the sample and reference temperature to be measured directly and avoids the errors associated with detecting the sample temperature and reference temperature independently and then calculating a small difference between two relatively much larger quantities.

In a further configuration of the Wheatstone bridge, the sample and reference are each heated with two heater elements and the four heater elements are configured in a full bridge arrangement so that the voltage output of the bridge circuit is doubled for a given temperature difference.

Differences between the resistances of sample and reference heater elements may lead to non-zero bridge circuit output and unequal heating of the sample and reference. It is desirable to balance the bridge circuit so that the bridge circuit output is zero when the sample and reference are at the same temperature, and also to balance the bridge circuit so that the sample and reference receive the same power input when a voltage is applied across the bridge circuit. The combination of voltage and power balancing can be achieved with four trim resistors, either in series or parallel configurations.

Digital PCR is a technique in which a sample including PCR reagents is first partitioned into sub-samples in a number of separate compartments (for example droplets or regions partitioned by walls), and all sub-samples are then temperature cycled to allow progression of the PCR reaction.

The objective is to determine the concentration(s) of one or more target oligonucleotides in the original sample more precisely and more accurately than is possible with real-time PCR. Real-time PCR quantifies DNA concentration by determining CT, the number of amplification cycles required for a measurement of the PCR reaction to exceed a threshold value. The starting concentration of DNA is related to CT, with higher concentrations resulting in a smaller value of CT.

Statistical analysis of the number of sub-samples in which PCR successfully progresses allows a more accurate and precise estimate of the DNA concentration in a sample. Sub-samples where PCR progresses must have contained one or more target oligonucleotides, whereas sub-samples where PCR does not progress are assumed to contain none. The statistical method requires a large number of sub-samples for precise determination of concentration, and typically more than 1000 sub-samples are used, and more than 10,000 sub-samples for applications requiring higher sensitivity.

A significant disadvantage of existing digital PCR techniques lies in the requirement to first partition the sample into sub-samples. This requirement adds significantly to the complexity and hardware costs associated with the process. Droplet digital PCR requires microfluidic droplet generation with more complex reaction cells, precisely controlled flows of aqueous sample and immiscible oil, and additional time for generation of droplets prior to PCR amplification. An alternative to droplet digital PCR is to use a gas to divide reaction volumes. This requires controlled sample addition followed by controlled gas addition combined with use of gas-permeable barriers to allow gas to escape.

This invention provides a wall-free, droplet-free digital PCR system and method where the sample is not partitioned into disconnected sub-samples. Instead, PCR proceeds (or fails to proceed) in a number of reaction zones within the sample, where these reaction zones are defined only by the range of temperatures they experience. There are no physical barriers between reaction zones, and movement of oligonucleotides from one reaction zone to another is prevented only by the relatively slow diffusion of oligonucleotides through the solution. The sample is contained as a continuous body of liquid without solid, immiscible liquid, or gas barriers between sub-samples. This is enabled by the possibility of performing PCR with short cycle times, so that between 30 and 50 cycles of PCR amplification can be completed in less than 100-200 seconds, limiting the time for diffusion and the distance over which diffusion can occur.

In a variation of this approach, partial barriers may be introduced to define sub-sample locations for ease of subsequent reaction detection and analysis, and to reduce the speed of diffusion between adjacent sub-sample locations, thereby allowing the sub-samples to be more closely spaced and increasing the number of sub-samples for a given size of reactor and total volume of sample.

The diffusion coefficient of a double-stranded DNA molecule in water, DDNA with length [bp size] can be calculated using the following expression (reference: Lukacs, G. L. et al (2000) Size-dependent DNA mobility in cytoplasm and nucleus. J Biol Chem. 275(3):1625-9):

$$D_{DNA} = [bp\ size]^{-0.72} \times 4.9 \times 10^{-6}\ cm^2/s.$$

We consider the diffusion of a 100-base pair DNA sequence, representing a typical target for PCR amplification. The diffusion length $R_D$ on a 100 s timescale is 84 µm, so an isolated cluster of amplified DNA will spread by approximately this distance over 100 s. The equivalent volume of a sample partition for digital PCR, $V_P$ for a reaction volume of height $H_V$ can be calculated as:

$$V_P = \pi R_D^2 H_V.$$

This gives a volume of 2.2 nl for a reaction volume height of 100 µm, allowing a typical 5 µl sample to be divided into more than 1000 partitions, as is typically required for digital PCR. It is desirable to divide a sample into a large number of partitions when quantifying DNA concentrations using digital PCR, as a larger number of partitions will increase the precision of the determination and will enable a larger range of concentrations to be determined. Therefore fast amplification, of the order of 100 s, in combination with small reaction volume cell height, of the order of 100 µm, enables typical PCR sample volumes (typically up to 20 µl) to be analysed with digital PCR.

In addition to enabling small partition volumes, the flat reaction volume shape of the reactor described in this invention is convenient for fluorescence detection of amplified DNA for digital PCR using an array detector such as a digital camera.

Multiplexed PCR is a technique in which a sample is analysed to detect the presence of multiple different oligonucleotide sequences. One conventional approach is to use fluorescent labels with different fluorescence wavelengths to multiplex detection of different species, but this approach is typically limited to detection of up to approximately six species, due to the overlap of fluorescence wavelengths. An alternative conventional approach is to sub-divide the sample into different reaction volumes partitioned by barriers which can be solid, immiscible liquid or gas. This approach has the same disadvantages of increased complexity and analysis time as for digital PCR described above.

Figure 8A:
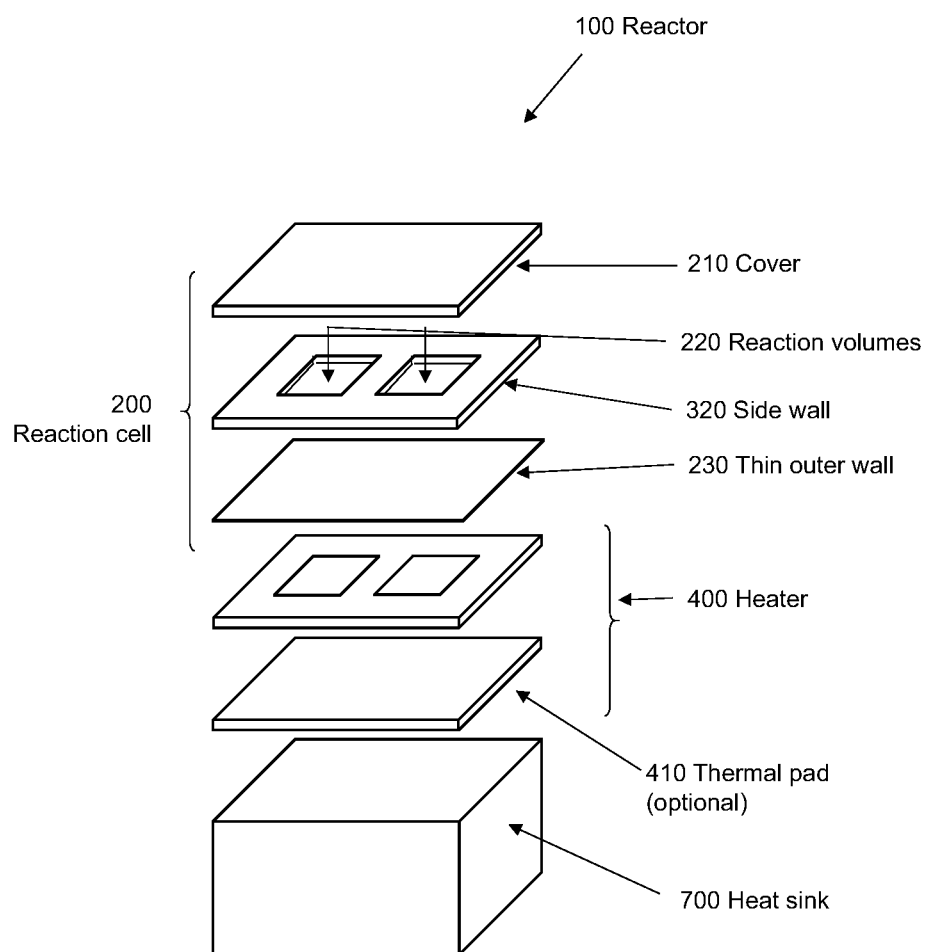
FIG. 8A shows a single sided reactor and FIG. 8B shows a double sided reactor according to the invention.
Figure 8B:
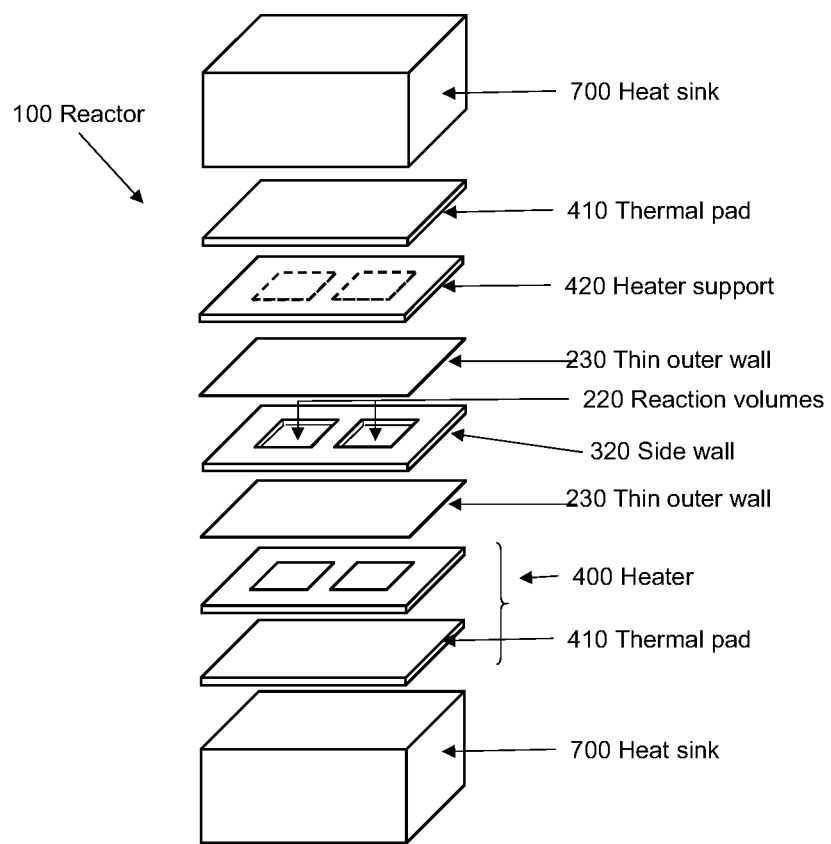

FIG. 8 shows a single sided reactor A (left) and a double sided reactor B (right) according to the invention. Each reactor comprises a reaction cell with one or more heaters and heat sinks. The heater comprises a heat-generating heater element on a heater support in contact with a heat sink. The heater support may include a softer and more flexible thermal pad layer to provide good thermal contact between a harder and more rigid heater support layer and a harder and more rigid heat sink. Embodiment A, a reactor with single-sided heater, comprises a single heater and heat sink and a reactor comprising a side wall, thin outer wall and cover. In Embodiment A the reaction volumes are enclosed by the cover, side wall and thin outer wall. Embodiment B, a reactor with double-sided heater comprises a reaction cell with two thin outer walls surrounding a side wall. In Embodiment B the reaction volumes are enclosed by the side wall and thin outer walls.

Figure 9A:
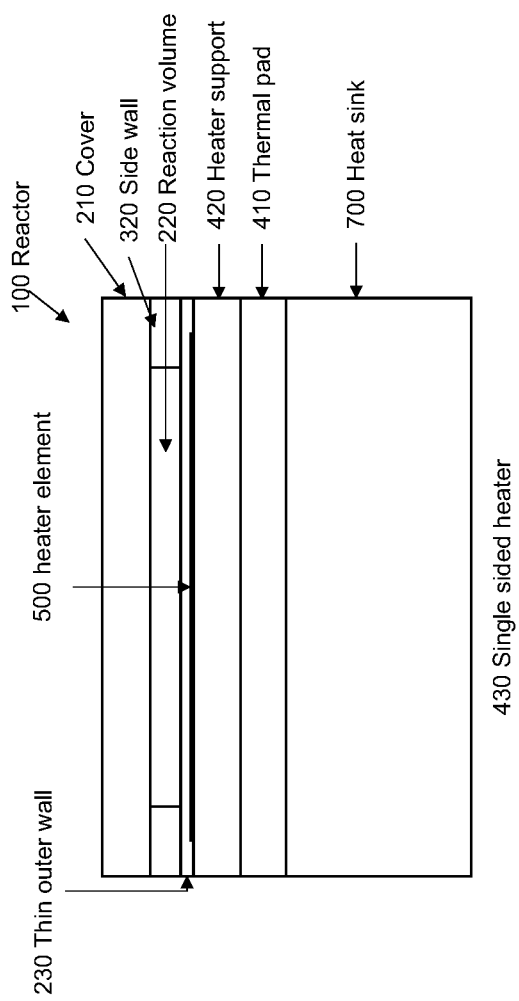
FIG. 9A shows a side view of a single sided reactor and FIG. 9B shows a side view of a double sided reactor according to the invention.
Figure 9B:
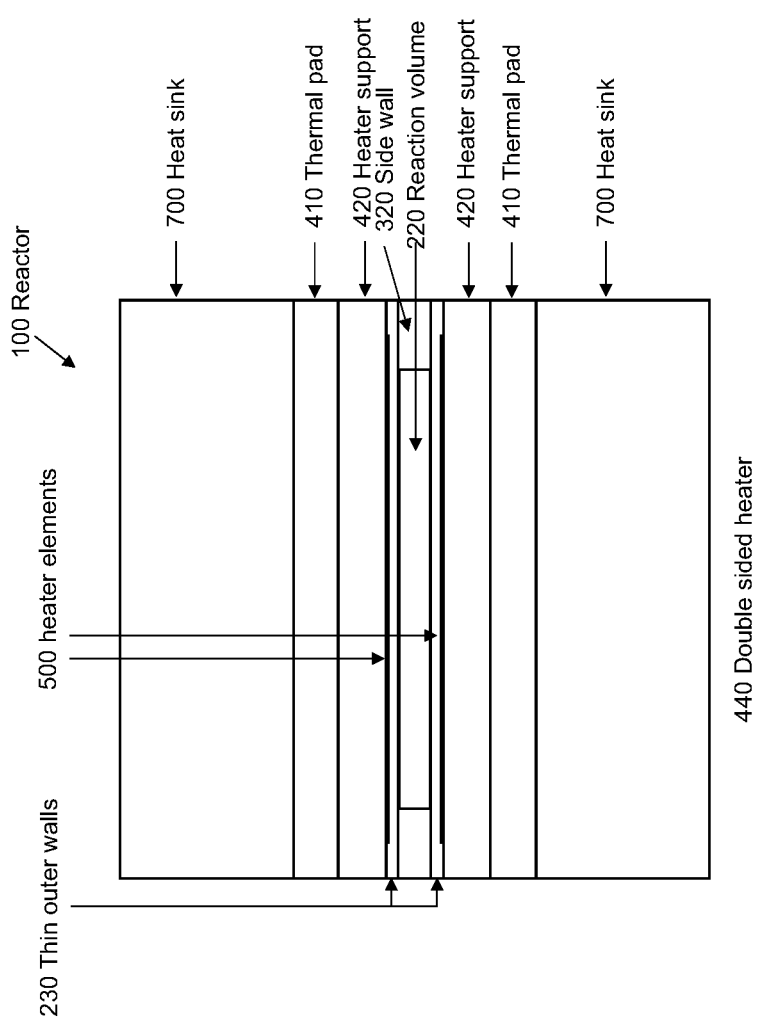

FIG. 9 shows a side view of a single sided reactor A (left) and a double sided reactor B (right) according to the invention.

Figure 10A:
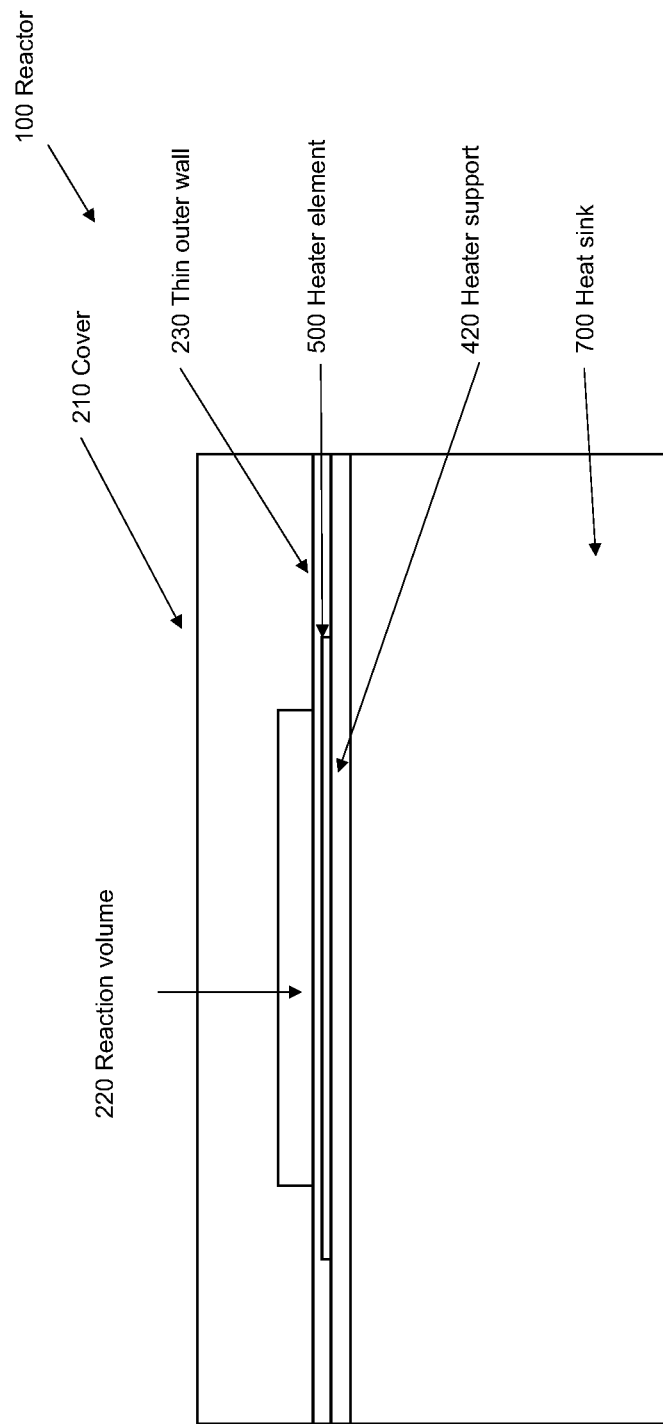
FIG. 10A shows a side view of a single sided reactor and FIG. 10B shows a side view of a double sided reactor according to the invention without thermal pads according to the invention.
Figure 10B:
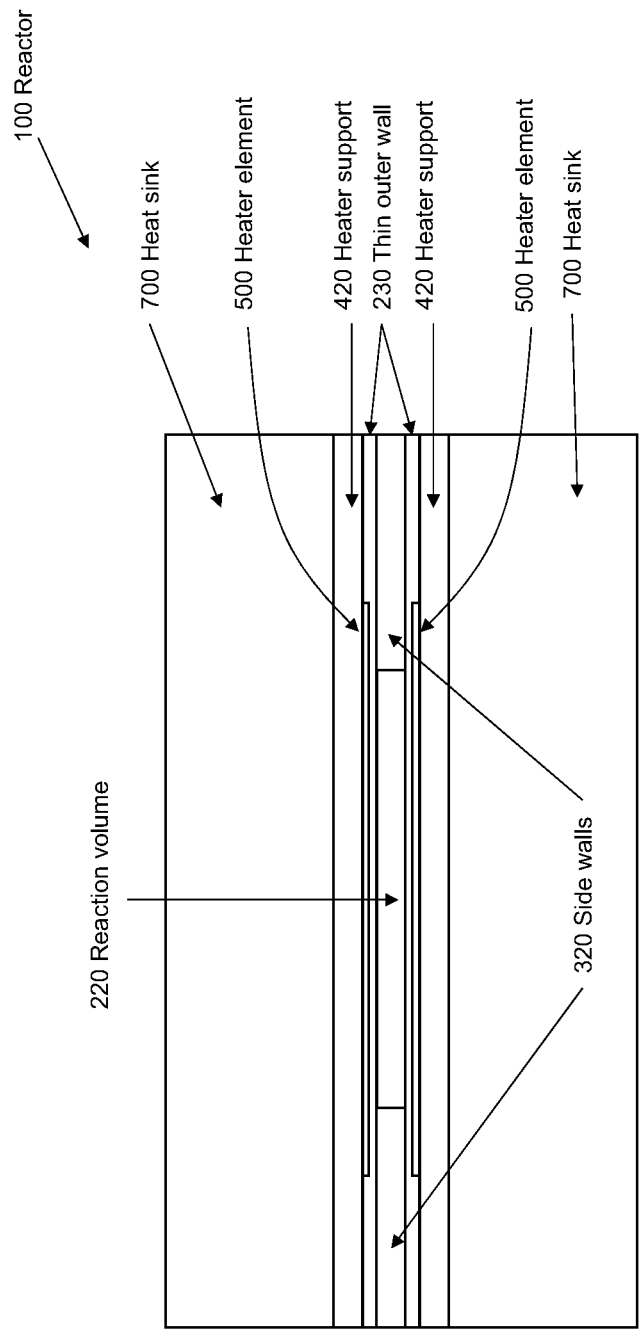

FIG. 10 shows a side view of a single sided reactor A (left) and a double sided reactor B (right) without thermal pads according to the invention.

Figure 11:
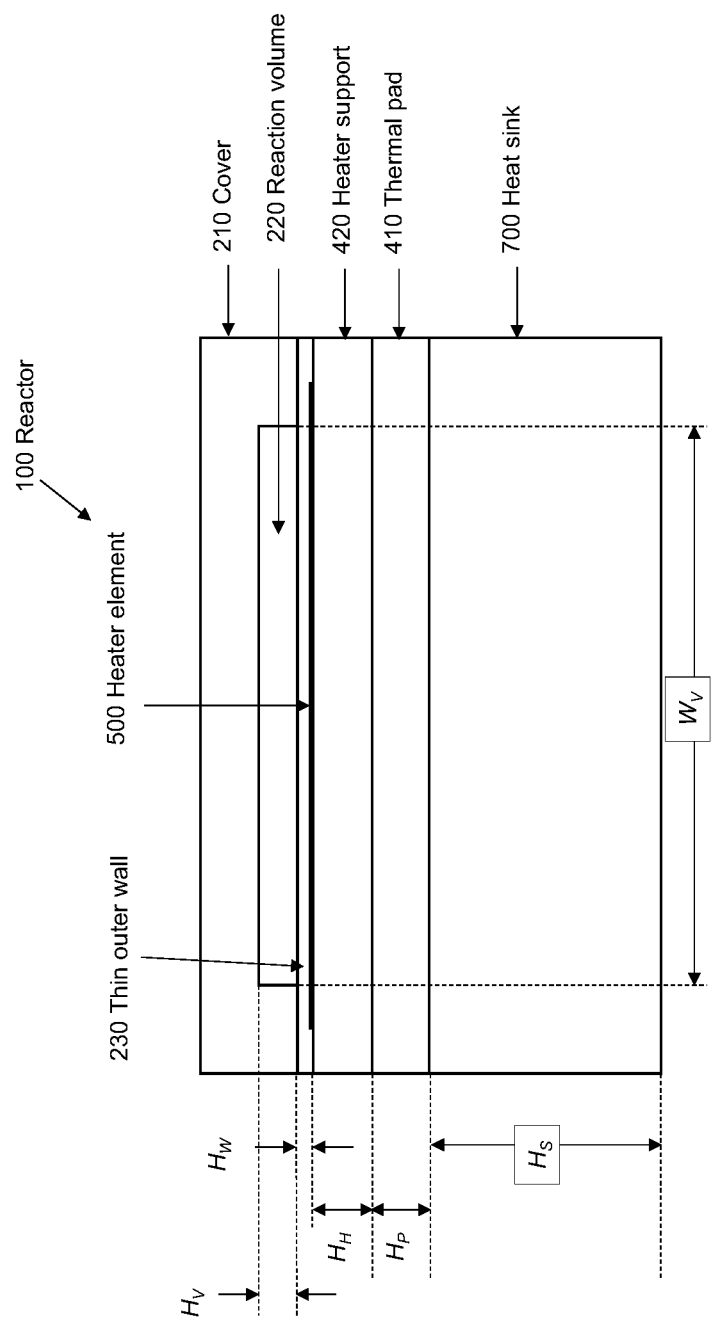
FIG. 11 shows dimensions of a reactor according to the invention.

FIG. 11 shows dimensions of a reactor according to the invention: reaction cell height $H_V$, thin wall thickness $H_W$, heater support height $H_H$, thermal pad height $H_P$, heatsink height $H_S$ and reaction cell width $W_V$.

Figure 12A:
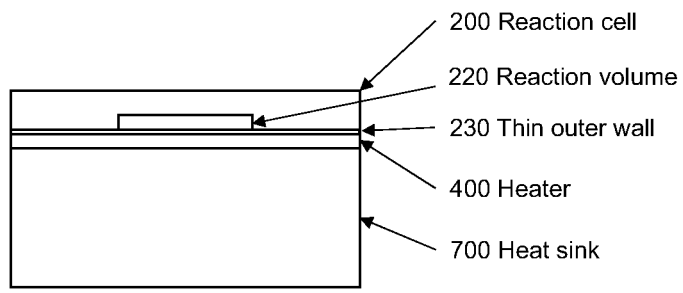
FIGS. 12A, 12B and 12C show cross-sectional views of alternative reactor geometries according to the invention.
Figure 12B:
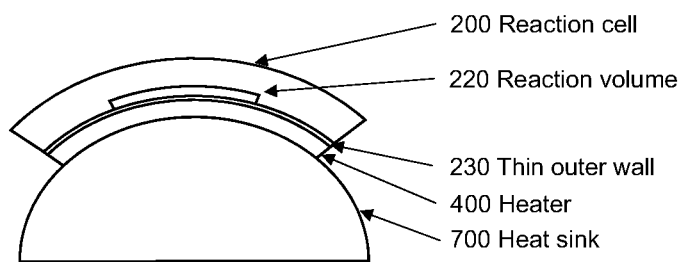
Figure 12C:
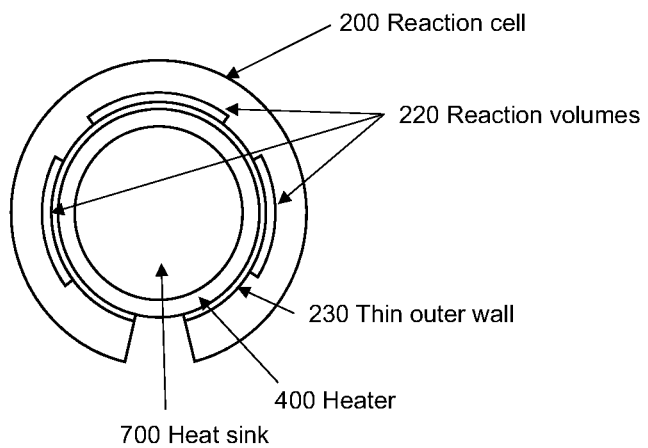

FIG. 12 shows cross-sectional views of different reactor geometries. All include a reaction cell in contact with a heater in contact with a heat sink. A planar geometry is shown in (A), a curved geometry in (B) and a cylindrical geometry in (C). In all cases the reaction volume is bounded by two larger area substantially parallel walls, and a smaller area side wall. At least one of the large area walls is a thin outer wall which is in contact with a heater.

As mentioned above, the reaction cell can have planar or curved forms. However, within the reaction cell, one or more reaction volumes to which thermocycling is applied may be constructed in a number of ways.

Figure 13A:
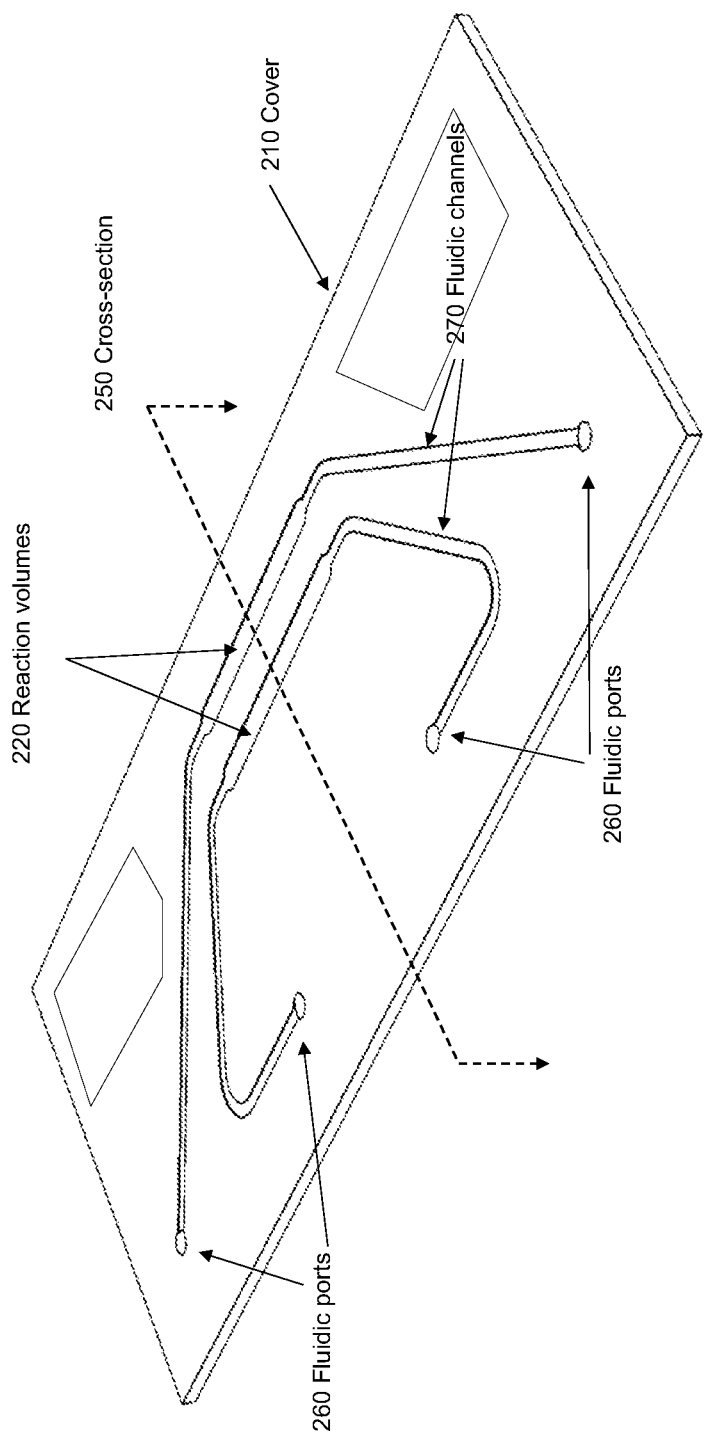
FIGS. 13A and 13B show example reaction cell covers that can be used with the invention.
Figure 13B:
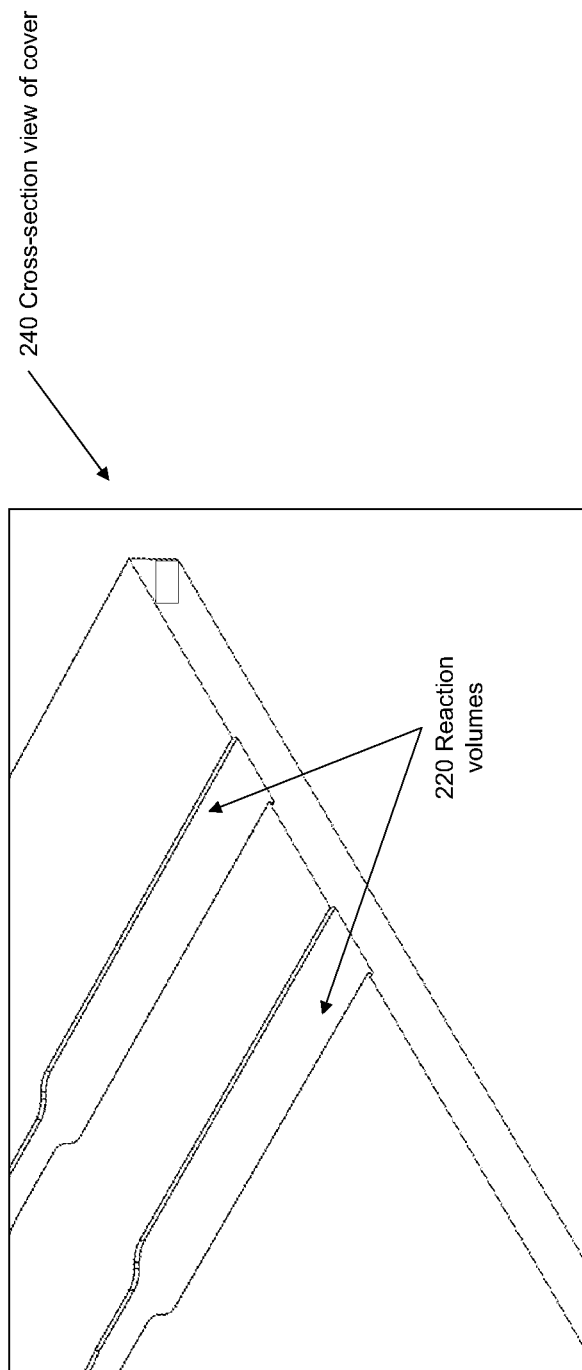

FIG. 13 shows a cover for a reaction cell cover employed in an embodiment of the invention comprising a substantially flat part with through-holes forming fluidic ports and recessed features defining reaction volumes and fluidic channels connecting the reaction volumes to the fluidic ports. The cover is shown in full (A) and in cross-section (B).

Figure 14A:
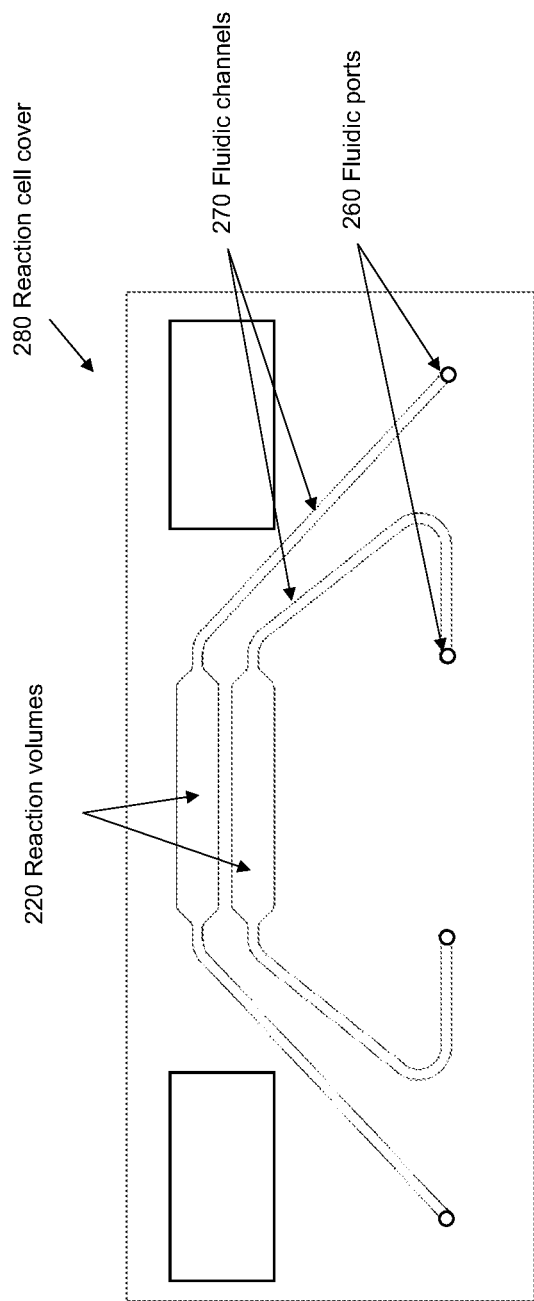
FIGS. 14A and 14B show a plan view of a reaction cell cover employed in an embodiment of the invention.
Figure 14B:
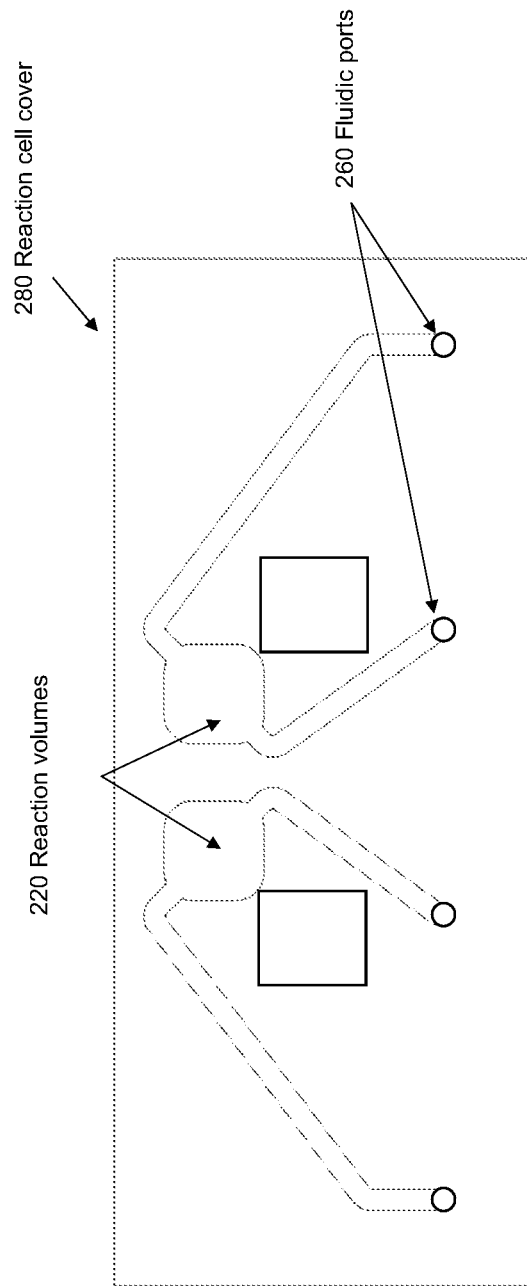

FIG. 14 shows a plan view of a reaction cell cover employed in an embodiment of the invention comprising reaction volumes connected by fluidic channels to fluidic ports. The reaction volumes may have an elongated or rectangular shape (A) or a substantially square shape (B).

Figure 15:
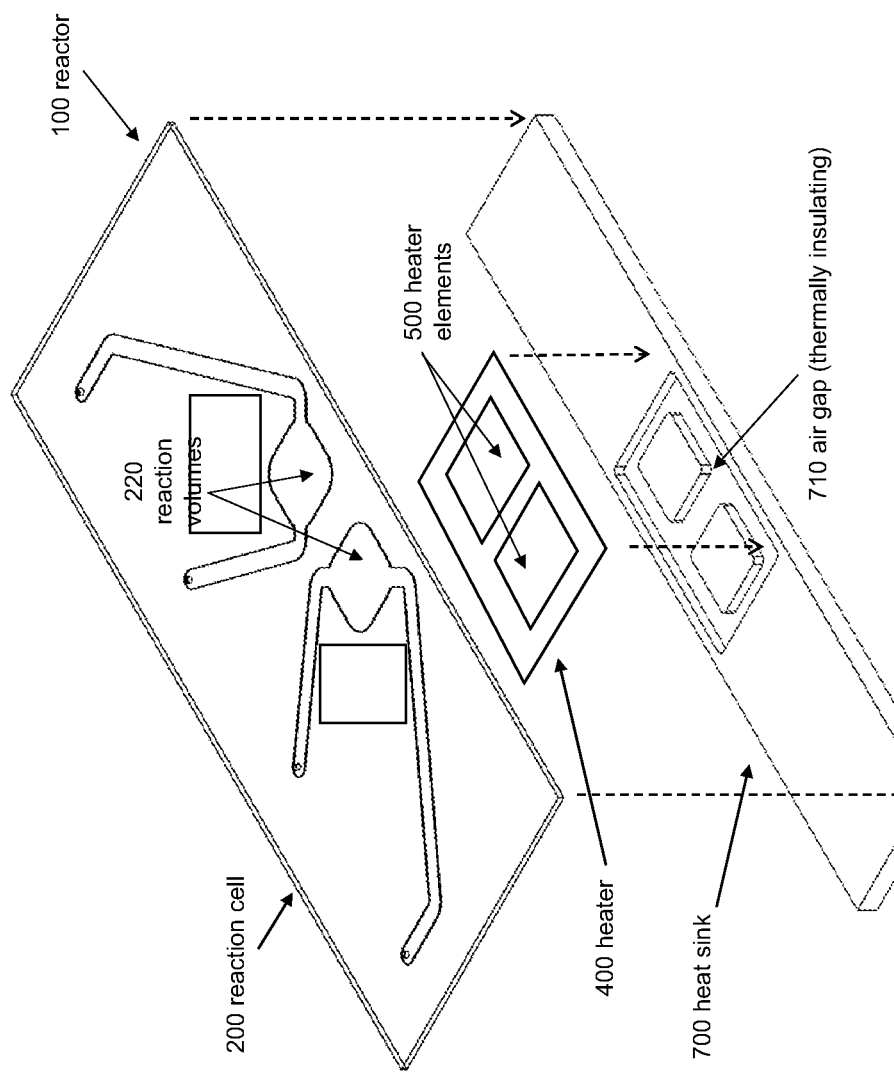
FIG. 15 shows an exploded view of a reactor according to the invention.

FIG. 15 shows an exploded view of a reactor according to the invention, which comprises the assembly of a reaction cell, heater and heat sink. The reaction cell contains two reaction volumes, with each reaction volume located above a heater element which extends laterally beyond the edge of the reaction volume. The heater makes thermal contact with the heat sink (optionally via a thermal pad, not shown in this figure). A thermally insulating air gap located near the perimeter of the heater element region may be used to locally reduce the rate of heat flow from the heater to the heat sink, thereby reducing the tendency for the edges of the heater element regions to be cooler than the centre, and improving the thermal uniformity within the reaction volume.

Figure 16B:
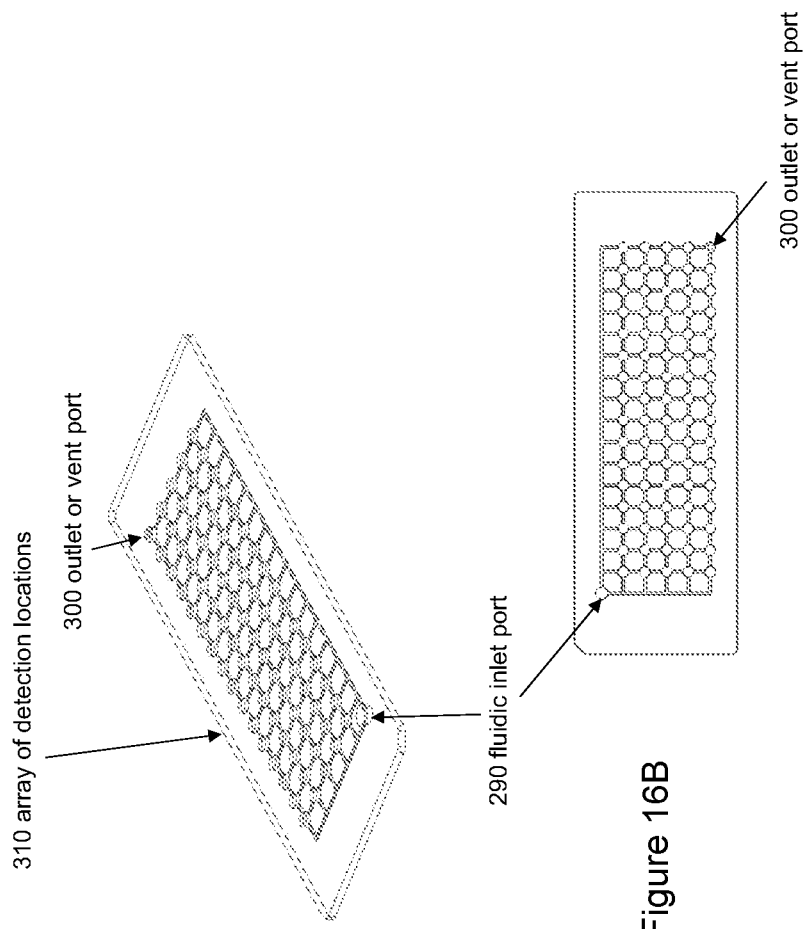
FIGS. 16A and 16B show two formats of reaction cell employed in the invention.
Figure 16A:
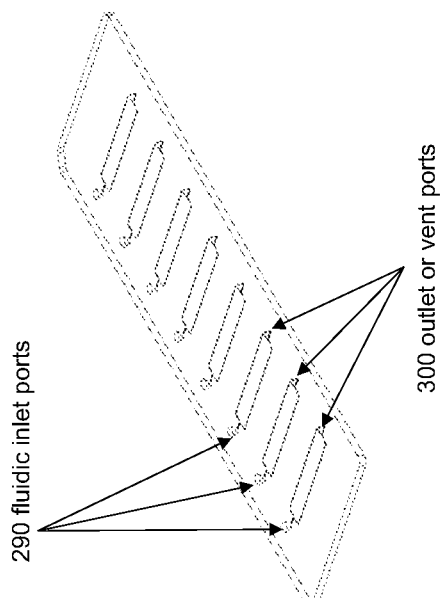

FIG. 16 shows two formats of reaction cell employed in embodiments of the invention: (A) reaction cell for multiple samples (8-sample format shown), and (B) reaction cell for a single sample with multiple detection locations. The detection locations may be used to implement digital PCR where the number of locations at which amplified DNA is detected is used to calculate the concentration of the target sequence in the sample. The detection locations may also be used to implement multiplexed PCR to detect multiple different target sequences, for example by providing different sequence-specific PCR primers at different detection locations. The reaction cell in each of FIGS. 16(A) and 16(B) may have a single reaction volume associated with a single heater element.

In one embodiment, we provide a wall-free multiplexed PCR system and method where the sample is not partitioned into discontinuous sub-samples. Instead, the reactor is pre-loaded with an array of different reagents for amplification or detection of different oligonucleotide sequences, with different reagents present at different locations. The sample is then loaded into the reactor and analysed as a continuous body of liquid. The spacing of the target-specific reagents is chosen such that the distance from one location to an adjacent location is greater than the diffusion length for the time required for the detection reaction, typically 30-50 cycles of PCR in the case of oligonucleotide detection.

In the case of PCR amplification of different target sequences, with this example different primer pairs can be pre-loaded at different locations within the reaction volume, for example by deposition of an array of primer pairs onto an array of locations on one of the large area walls of the reaction cell, followed by drying. Primer-specific amplification can occur at the location of each primer-pair and the result of this amplification can be determined independently of the outcome of PCR amplification at neighbouring locations, provided that the PCR amplification is carried out in less time than the time required for reaction products or primers to diffuse to neighbouring locations.

A typical primer is an oligonucleotide sequence with approximately 20 bases and is shorter than the target DNA sequence, with correspondingly larger diffusion coefficient. Applying the same formula as for DNA diffusion, a 20 base primer may diffuse 151 µm within a time of 100 s. Independent detection requires that adjacent locations for multiplexed detection must be separated by at least twice this distance, and preferably at least 4 to 6 times this distance. As an example, we can consider a 5 µl reaction volume with height 100 µm, area 50 mm2, and approximately 1 mm spacing between adjacent locations. Each detection location occupies an area of 1 mm2, giving 50 independent detection locations for multiplexing.

Figure 17:
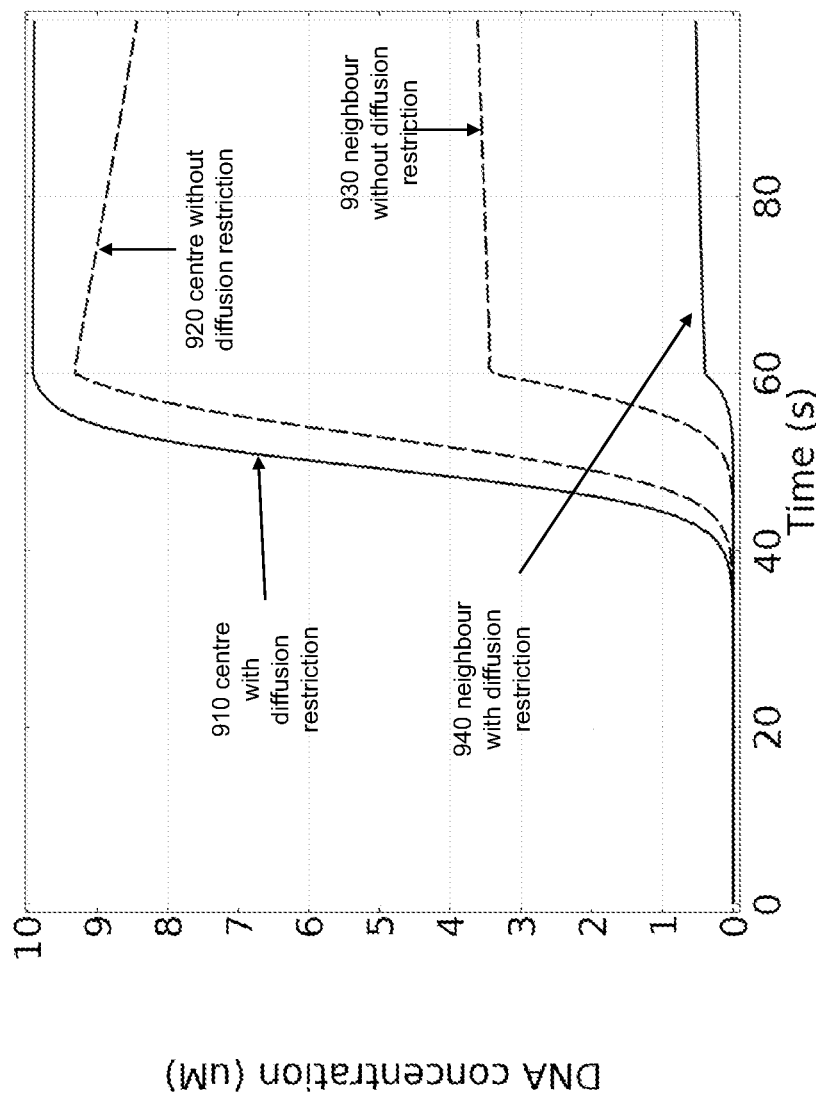
FIG. 17 shows a simulation of simultaneous DNA amplification and diffusion up to time 60 s followed by DNA diffusion only after time 60 s during operation of the invention.

Diffusion restriction channels can be used to limit diffusion of reagents and reaction products between neighbouring reaction zones for the duration of a reaction. FIG. 17 shows a simulation of simultaneous DNA amplification and diffusion up to time 60 s followed by DNA diffusion only after time 60 s in a reactor according to the invention. At the start of the simulation, a centre cell contains one DNA molecule and this is amplified by PCR with a cycle time of 2 s. The case of a reaction cell with diffusion restriction channels is shown with a solid line, while the case of a reaction cell without diffusion restriction channels is shown with a dashed line. Fast amplification is required in to amplify fully in one reaction zone before significant diffusion and amplification in a neighbouring zone can occur. In this example, the DNA concentration in the neighbouring cell with diffusion restriction channel is approximately 5% of the DNA concentration in the main cell at time 60 s, while the DNA concentration in the neighbouring cell is approximately 35% in the case without diffusion restriction channels.

Figure 18B:
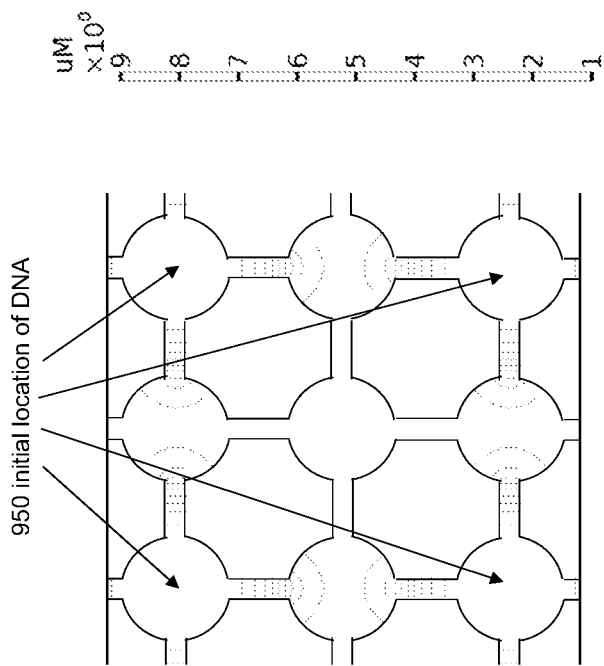
FIGS. 18A and 18B show the DNA concentration at time 100 s after the start of PCR amplification for two example cells employed with the invention.
Figure 18A:
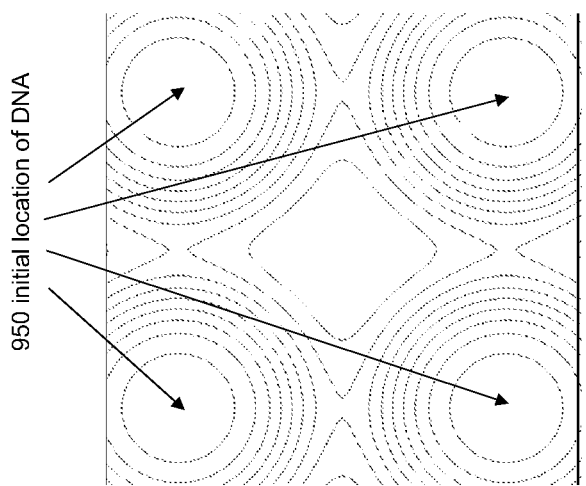

FIGS. 18A and 18B shows the results of a simulation of DNA concentration in a method employing the invention at time 100 s for two cases: FIG. 18A is a reaction cell without diffusion restriction channels, while FIG. 18B is a reaction cell with separate reaction zones (detection locations) separated by diffusion restriction channels. DNA diffusion to neighbouring cells is reduced by the diffusion restriction channels. In both cases, PCR amplification is simulated for 60 s (30 cycles of PCR amplification with 2 s per cycle), followed by diffusion for a further 40 s. The reaction cell in each of FIGS. 18(A) and 18(B) may have a single reaction volume associated with a single heater element.

Figure 19:
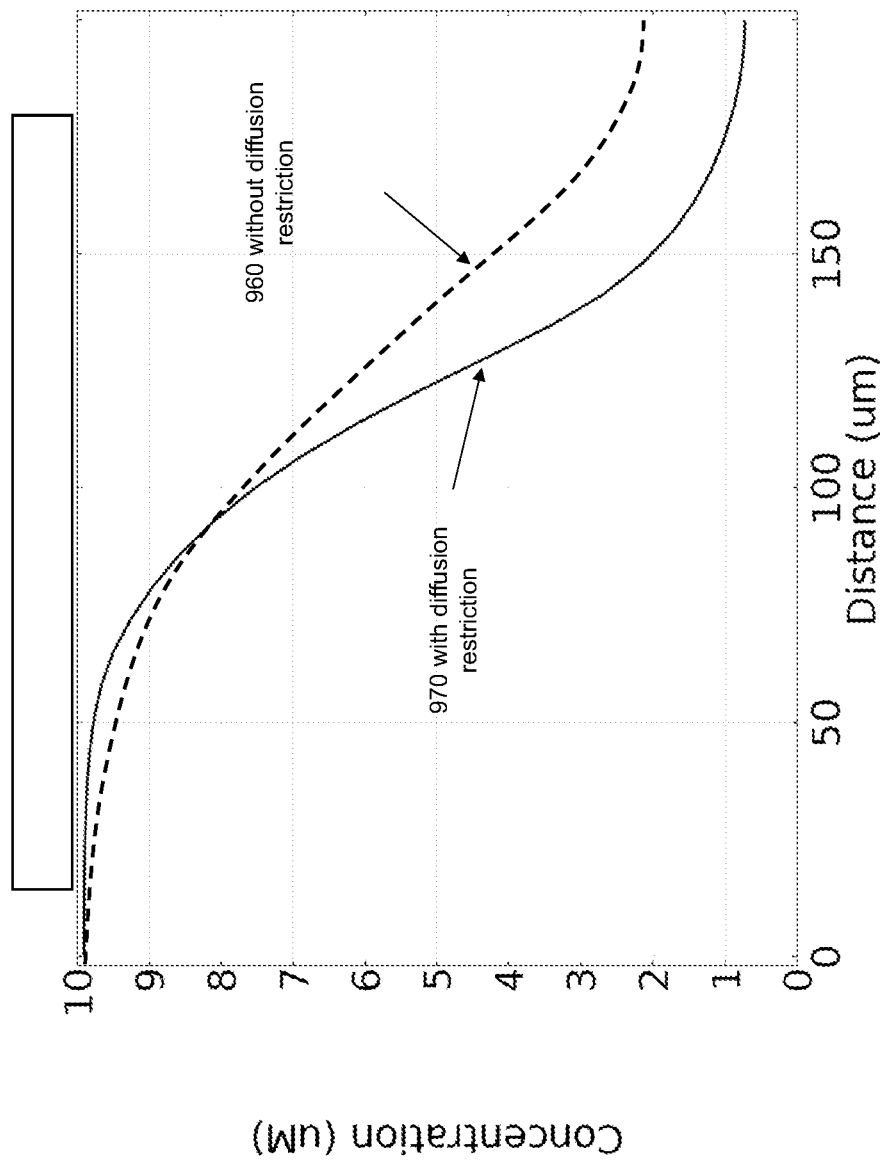
FIG. 19 shows the concentration variation in a method employing the invention with position at time 100 s after the start of PCR amplification.

FIG. 19 shows the concentration variation in a method employing the invention with position at time 100 s after the start of PCR amplification. The diffusion barrier helps to maintain high DNA concentrations near the locations where DNA has been amplified and low concentrations in neighbouring reaction locations. This allows digital PCR or multiplexed PCR or other reactions to be carried out in a reactor with a continuous fluid path for reagent and sample flow, avoiding the need for droplets or other measures to isolate the reacting volumes.

Figure 20:
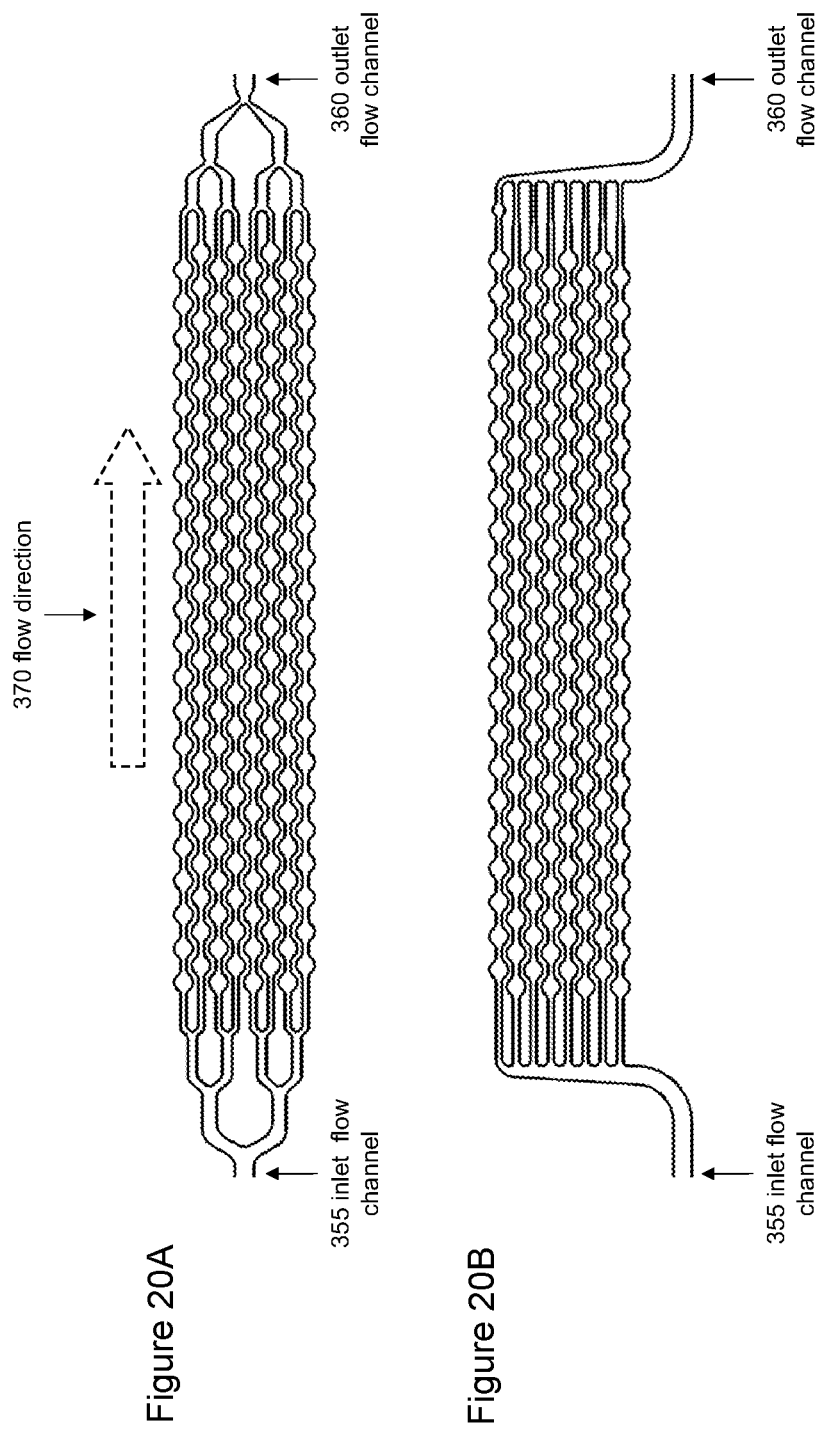
FIGS. 20A and 20B show two different designs of fluidic cell arrays that may be employed with the invention.
Figure 21:
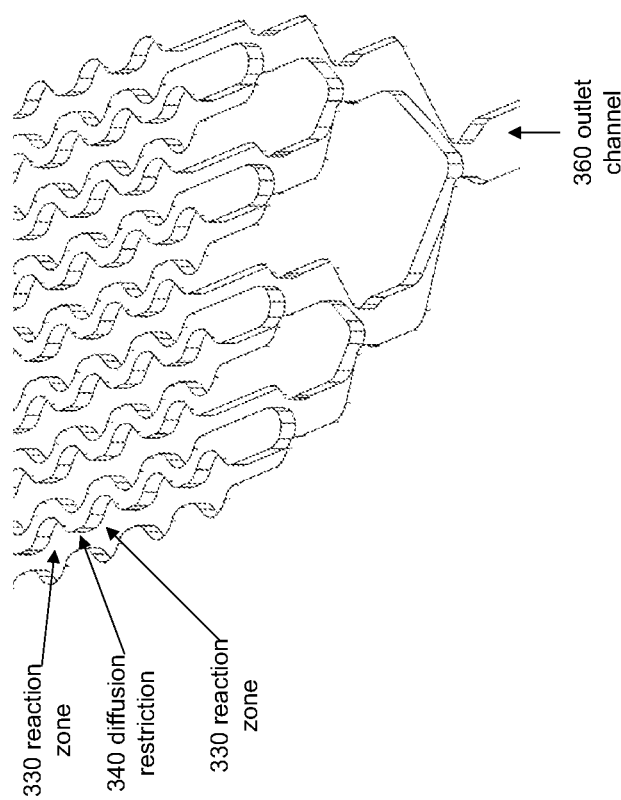
FIG. 21 shows detail of fluidic cell with reaction zones separated by diffusion restrictions.

FIG. 20 shows two different designs of fluidic cell with an array of reaction zones connected by smaller channels which restrict diffusion between adjacent reaction zones according to the invention. The reaction zones may contain different reagents such as PCR primers in order to carry out a multiplexed amplification and detection of different DNA sequences at different locations. Alternatively, the reaction zones may all contain the same reagents in order to carry out digital PCR. The diffusion restriction channels allow the array of reaction zones to be filled without the need for generation of aqueous droplets in oil to provide isolated reaction zones, thus simplifying and reducing the cost of carrying out the reaction. The fluidic cell in each of FIGS. 20(A) and 20(B) may have a single reaction volume associated with a single heater element FIG. 21 shows detail of a fluidic cell with reaction zones 330 separated by diffusion restrictions 340. The fluidic paths from the reaction zones recombine to allow the reaction product to be collected and transferred out of the reaction cell.

Figure 22A:
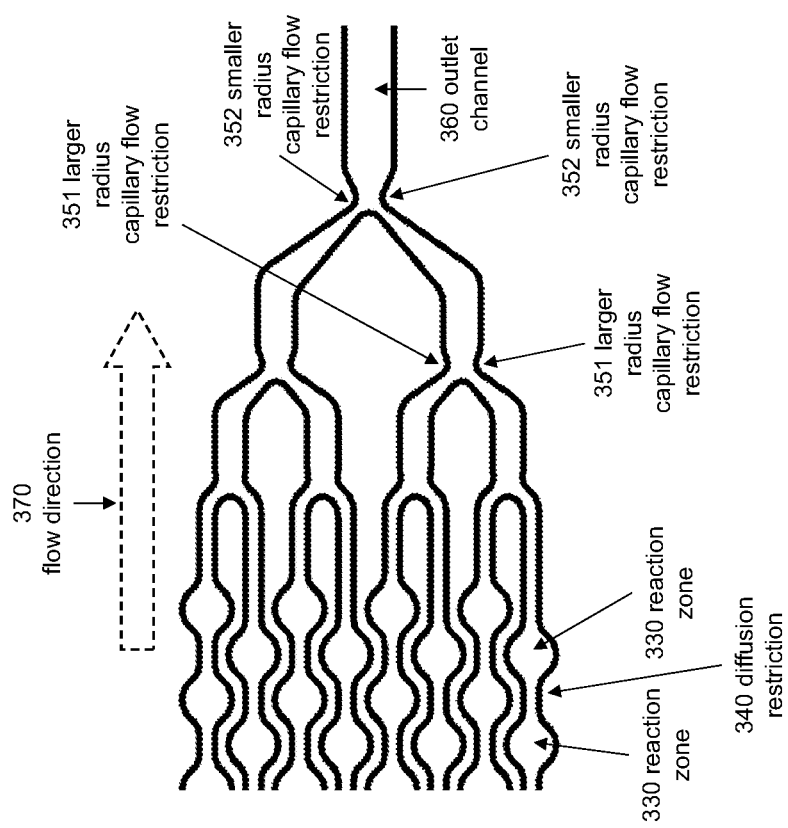
FIGS. 22A and 22B show detail of outlets of reaction cells with recombining fluidic paths.
Figure 22B:
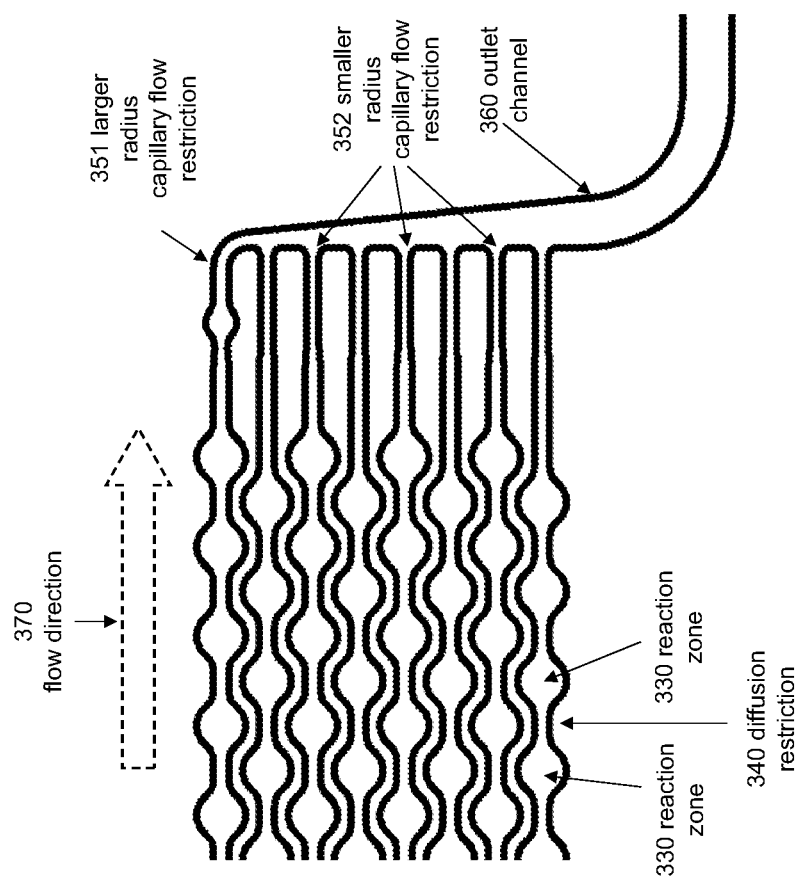

FIG. 22 shows detail of the outlets of reaction cells with recombining fluidic paths. In order to avoid formation of air bubbles, a sequence of capillary flow restrictions are placed in the fluidic path, with the capillary burst pressure increasing in the flow direction. In FIG. 22(A) the larger radius capillary flow restriction 351 has a lower burst pressure than the smaller radius capillary flow restriction 352. When flows from two channels join, one channel can pin at a capillary flow restriction until the adjacent channel is filled, at which point the menisci of the two advancing liquid fronts can touch and the flows recombine without generation of air bubbles. In FIG. 22(B) liquid flow is stopped at the smaller capillary radius flow restriction points 352 while liquid flows past the larger capillary radius flow restriction point 351. Liquid streams recombine as the advancing meniscus reaches each of the restriction points 352.

Figure 23B:
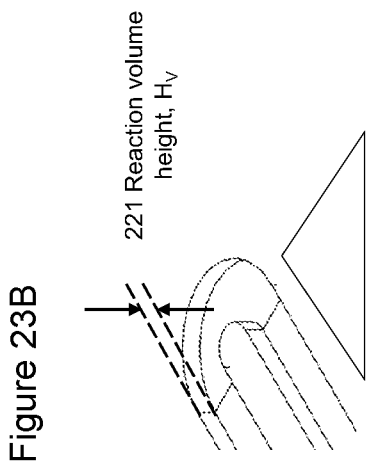
FIGS. 23A, 23B and 23C show reaction volumes according to the invention.
Figure 23A:
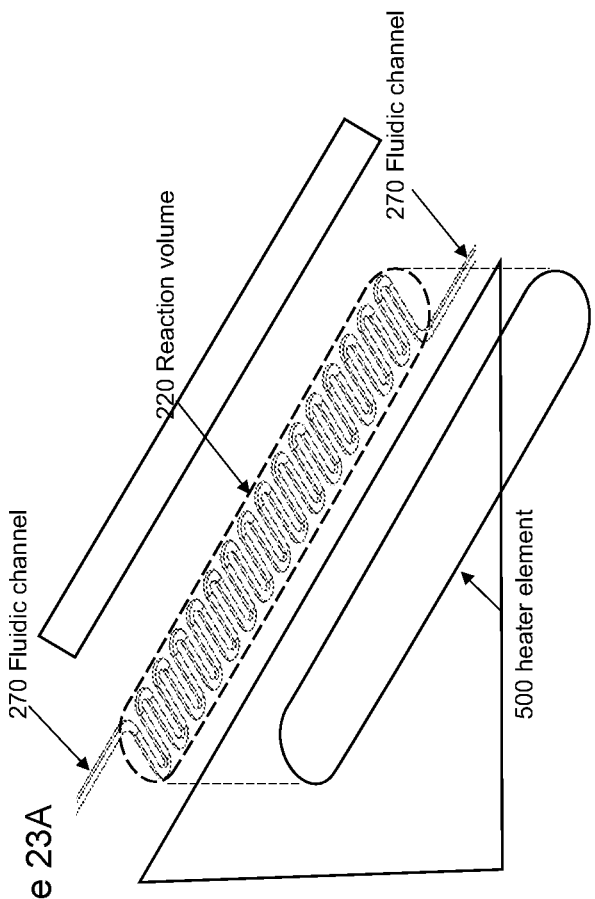
Figure 23C:
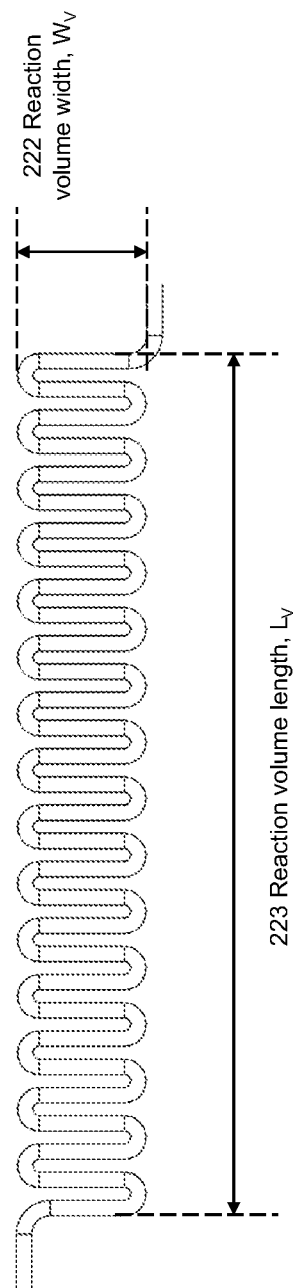

FIG. 23 shows another embodiment of a reaction cell in which a reaction volume 220 has width $W_V$, length $L_V$ and height $H_V$. In this example, the construction of the cell is made more robust by avoiding wide fluidic channels with large unsupported spans. The reaction volume 220 is located in register with and arranged to be heated by a heater element 500, and is constructed from a serpentine fluidic channel 270 with height $H_V$ which distributes a sample across the reaction volume area $W_V \times L_V$. The dimensions may, for example, be $W_V$=2.5 mm, $L_V$=16 mm, and $H_V$=0.1 mm. A reaction cell containing a reaction volume with this form provides several advantages: the fluidic path is easily controlled, bubbles can be flushed out, and the part can be manufactured using an embossing and laminating process to attach a thin outer wall 230 to the fluidic cell. To carry out PCR amplification, a sample is introduced into the reaction volume, liquid motion is stopped, positive pressure is applied, and the reaction volume is then thermocycled. PCR primers may be provided as a linear array along the serpentine channel. Primers may be chosen in view of their solubility, such that the primers remain substantially fixed along the channel.

Figure 24A:
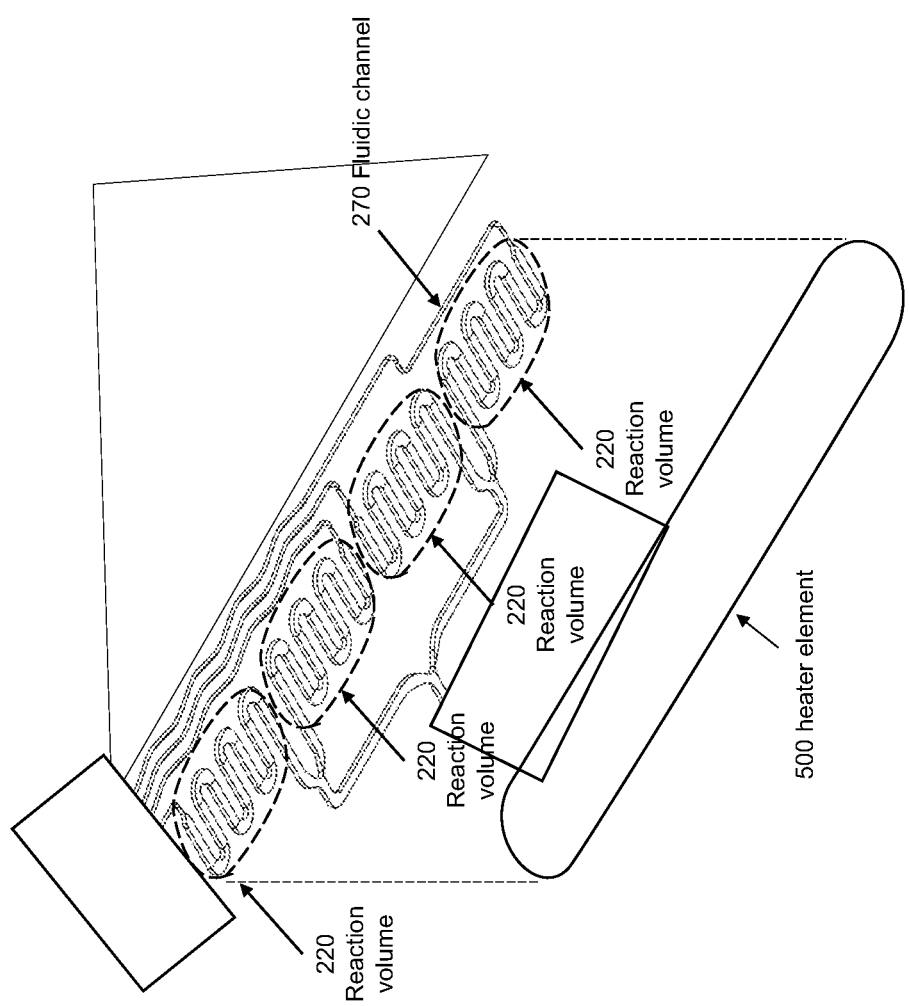
FIGS. 24A and 24B show reaction volumes according to the invention.
Figure 24B:
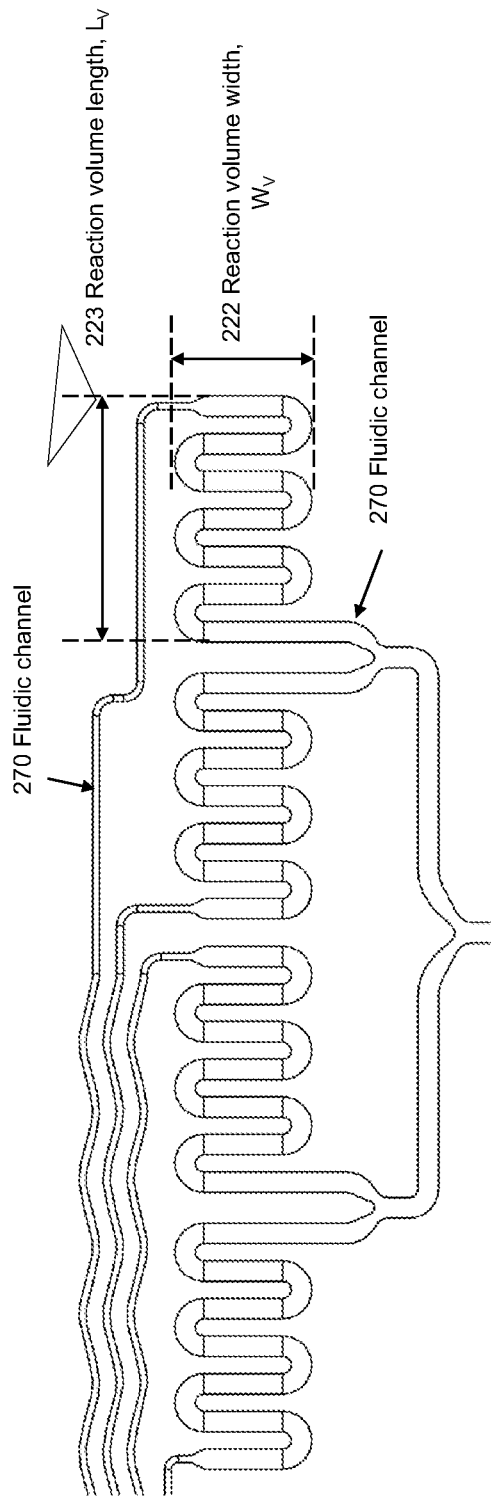

FIG. 24 shows another embodiment with a serpentine fluidic channel. In this embodiment, four reaction volumes 220 are arranged to be filled from a single sample via serpentine fluidic channels 270 and thermocycled by a heater element 500. Each reaction volume has width $W_V$ and length $L_V$. In this embodiment, the dimensions may, for example, be $W_V$=2.0 mm, $L_V$=3.6 mm, and $H_V$=0.1 mm.

Figure 25:
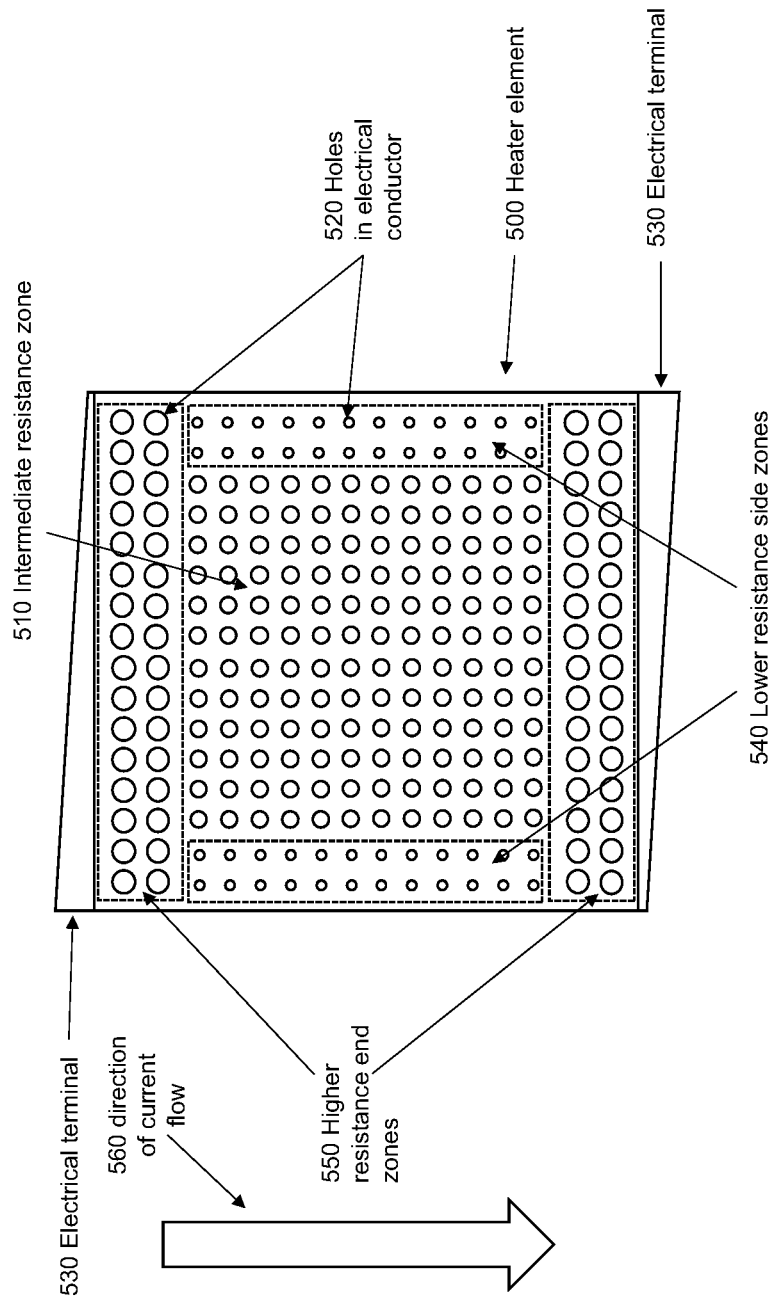
FIG. 25 shows an electrically conductive heater element according to the invention.

FIG. 25 shows an electrically conductive heater element employed in an embodiment of the invention with zones of intermediate, low and high sheet resistance to provide increased heating near the edges of the heater element, in order to increase the uniformity of the temperature across the element. The heater element is formed from a thin film conductor supported on an electrically insulating support. The sheet resistance of the heater element is locally increased by forming holes in the electrically conductive thin film, with a larger hole area fraction causing a larger increase in sheet resistance. An electric current flows between the electrical terminals to provide higher heating power density due to increased sheet resistance in the upper and lower high resistance zones and higher heating power density due to increased current density in the left and right lower resistance zones. The heater is also made partially transparent by forming holes in the electrically conductive layer, which is typically opaque. A partially transparent heater element is useful to allow optical monitoring of the reaction and in particular fluorescence detection of amplified DNA.

Figure 26:
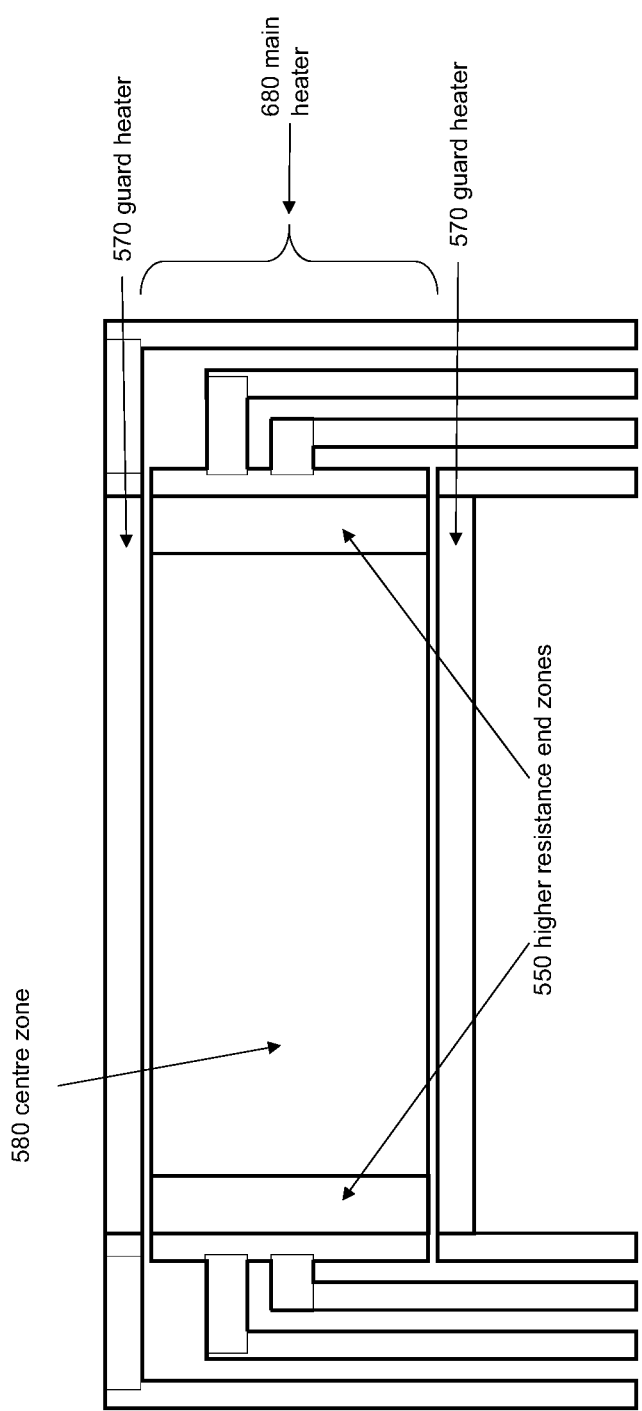
FIG. 26 shows an alternative approach to edge effect compensation in a heater element employed in an embodiment of the invention.

FIG. 26 shows an alternative approach to edge effect compensation in a heater element employed in an embodiment of the invention. Guard heaters are provided at one or more edges of the main heater, and the guard heaters are driven electrically to the same temperature setpoint as the guard heater. The main heater also has end heater zones with higher electrical resistance to provide increased heating near the ends, thereby reducing edge effects. The main heater is provided with four-terminal Kelvin connections so that its resistance can be measured accurately and used to calculate the temperature of the heater element. The resulting temperature measurement is used to control the heater drive power and thermocycling behaviour.

Figure 27:
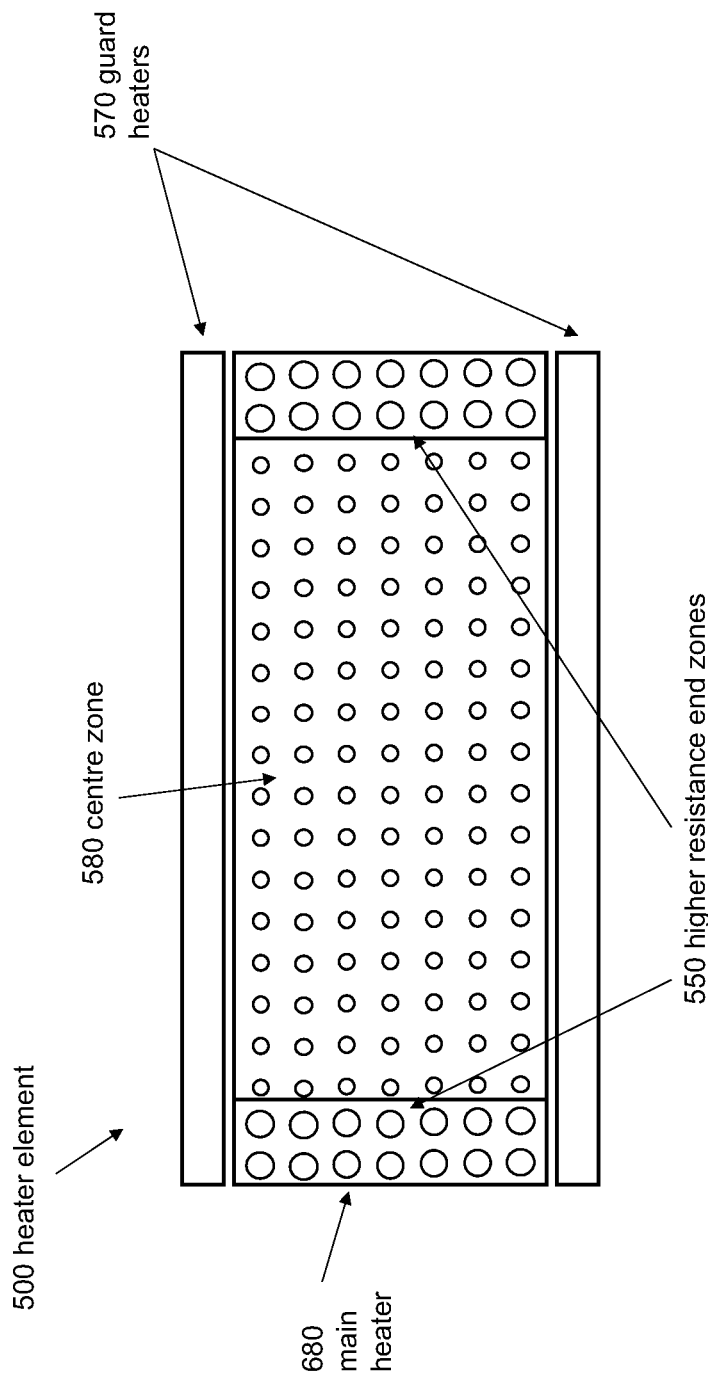
FIG. 27 shows a heater element employed in an embodiment of the invention.

FIG. 27 shows a heater element employed in an embodiment of the invention comprising a main heater with guard heaters located near two of the edges. In this case the main heater is elongated and the guard heaters are located near the long edges. The main heater has a lower resistance central zone and higher resistance end zones, such that a current flowing in the long direction of the heater will cause increased heat output in the high resistance end zones and this increased heat output will compensate for edge effects, increasing the temperature uniformity of the heater. A benefit of an elongated heater element is that it matches the form of an elongated reaction volume which is convenient to manufacture and convenient to fill without trapping air bubbles. The perforations in the main heater make the heater partially transparent.

Figure 28B:
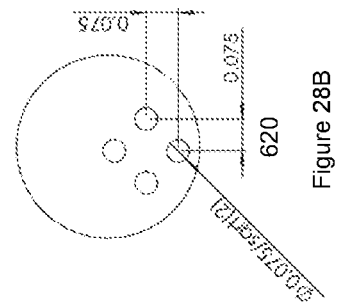
FIGS. 28A, 28B and 28C show the design of a heater for two reaction volumes employed in an embodiment of the invention.
Figure 28C:
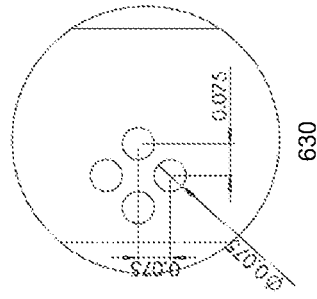
Figure 28A:
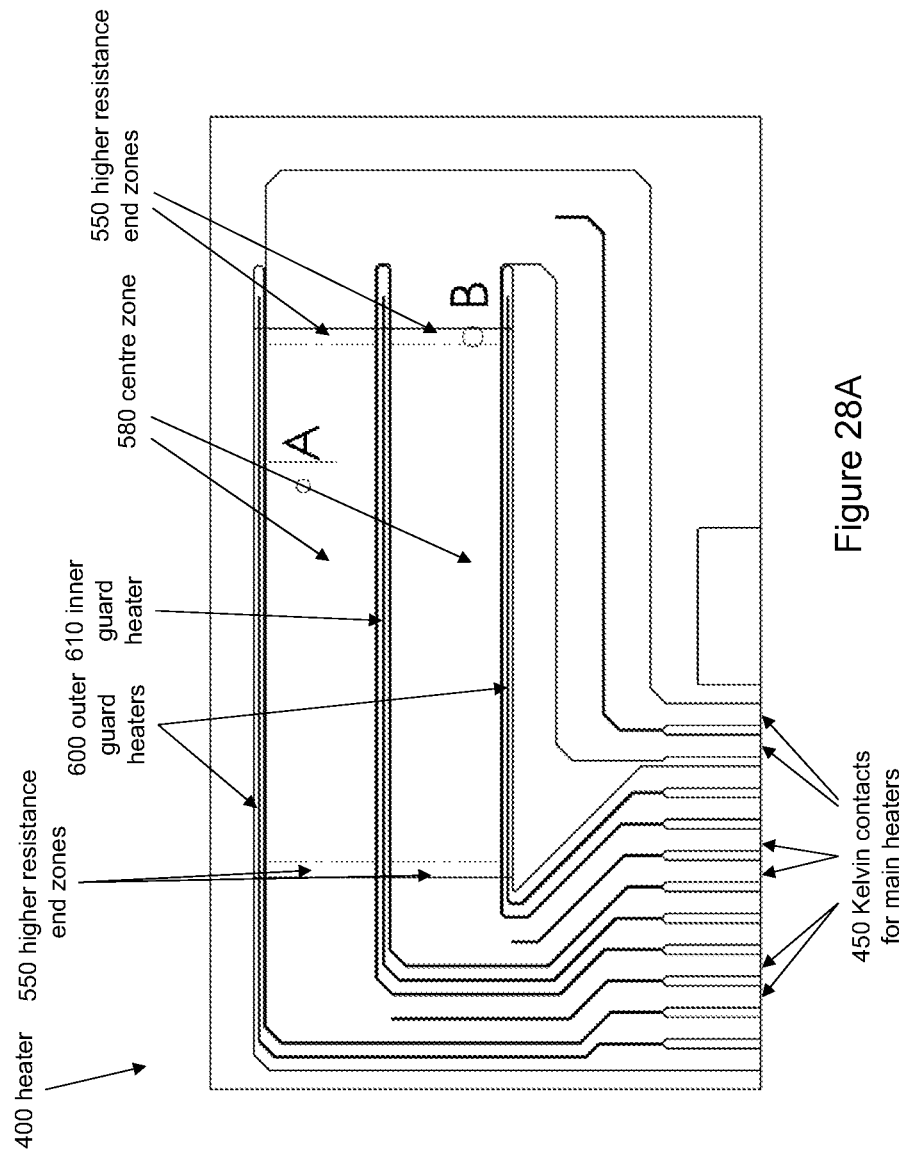
Figure 29A:
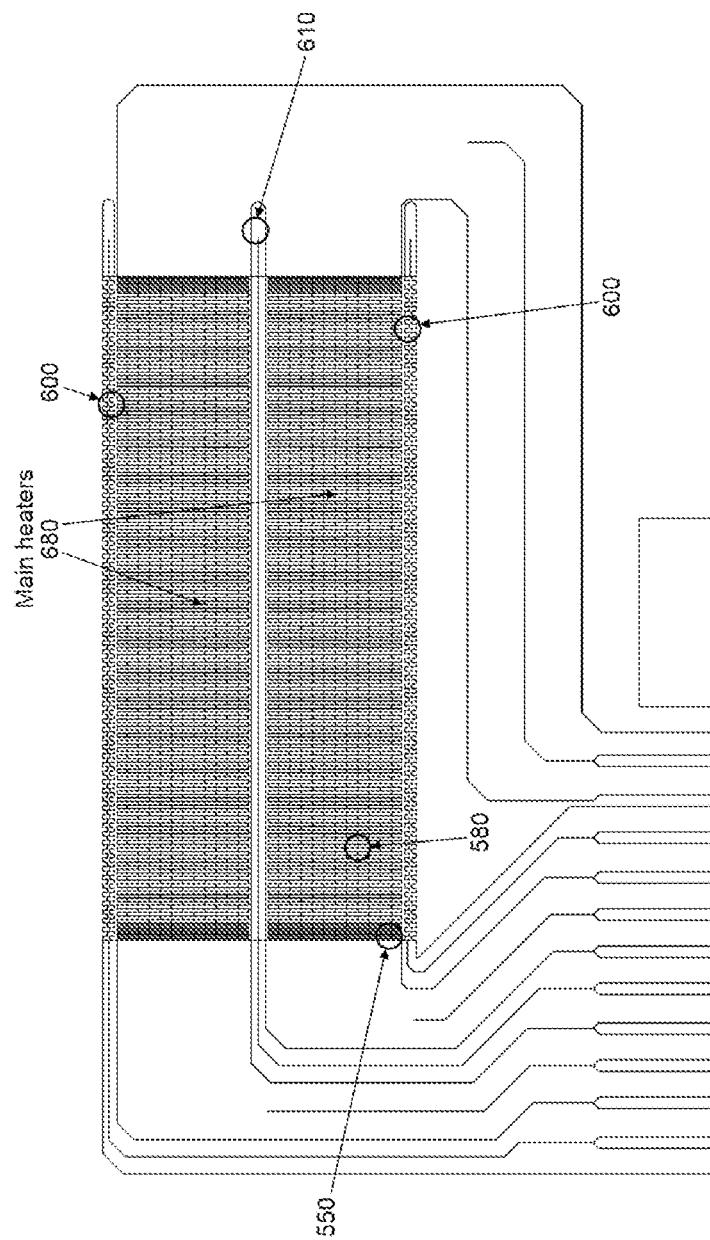
FIGS. 29A, 29B, 29C and 29D show a heater employed in an embodiment of the invention with patterned electrodes.
Figure 29C:
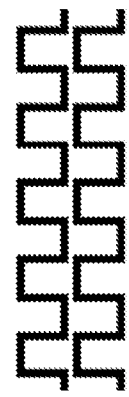
Figure 29D:
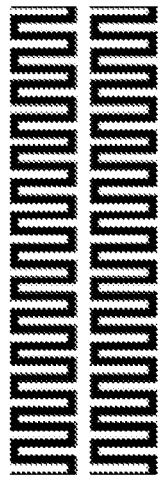
Figure 29B:
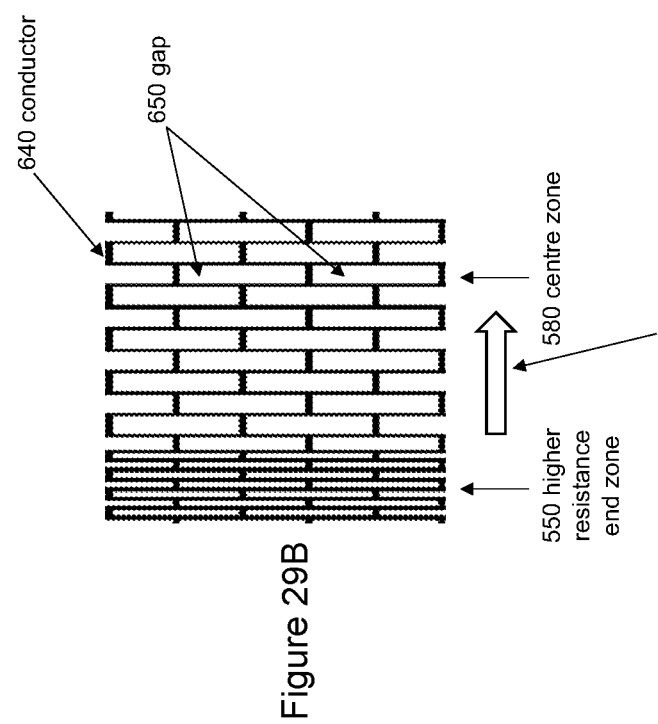

FIG. 28A shows the design of a heater for two reaction volumes employed in an embodiment of the invention. The heater contains two elongated main heater elements with three guard heater elements adjacent to the long edges of the main heater element. The end zones of the main heaters have a higher sheet resistance created by increasing the area fraction of holes in a thin film conductor (FIG. 28C), while the central zones of the main heaters have a lower sheet resistance created by decreasing the area fraction of holes in a thin film conductor (FIG. 28B). The main heaters are provided with Kelvin contacts to allow the heater resistance to be measured accurately. The change in heater resistance with temperature is used to monitor and control the heater temperature. Separate electrical contacts are provided for the guard heaters, allowing independent electrical drive and control. The outer guard heaters may be designed to have a lower resistance than the inner guard heater so that when all the guard heaters are driven with the same voltage, the outer guard heaters generate more heat which improves the temperature uniformity as greater heat output compensates for the greater heat loss at the edge of the heater.

FIG. 29 shows a heater employed in an embodiment of the invention with patterned electrodes to vary resistance. The heater (A) has two main heaters which have higher resistance regions near their short ends and lower resistance regions in the centre. The resistance can be adjusted by the geometry of gap regions which provide variable conductor geometry. (B) shows an example of a higher and lower resistance region. The elongated gap is oriented perpendicular to the direction of current flow in order to increase the sheet resistance of the heater element. The larger aspect ratio gap provides a higher resistance end zone, while the smaller aspect ratio gap provides a lower resistance centre zone. The design of the main heater is robust to a single track breaking, by providing parallel electrical conduction paths. Guard heaters are placed near the long sides of the main heaters. The outer guard heaters (C) have lower resistance than the inner guard heater (D) in order to provide greater heat output when driven with the same drive voltage.

It will be appreciated that the heater element is substantially continuous with any holes having diameter less than the thickness of the reaction volume, $H_V$, or in the case of elongated gaps in the heating element, the gap width less than the thickness of the reaction volume, $H_V$.

Figure 30:
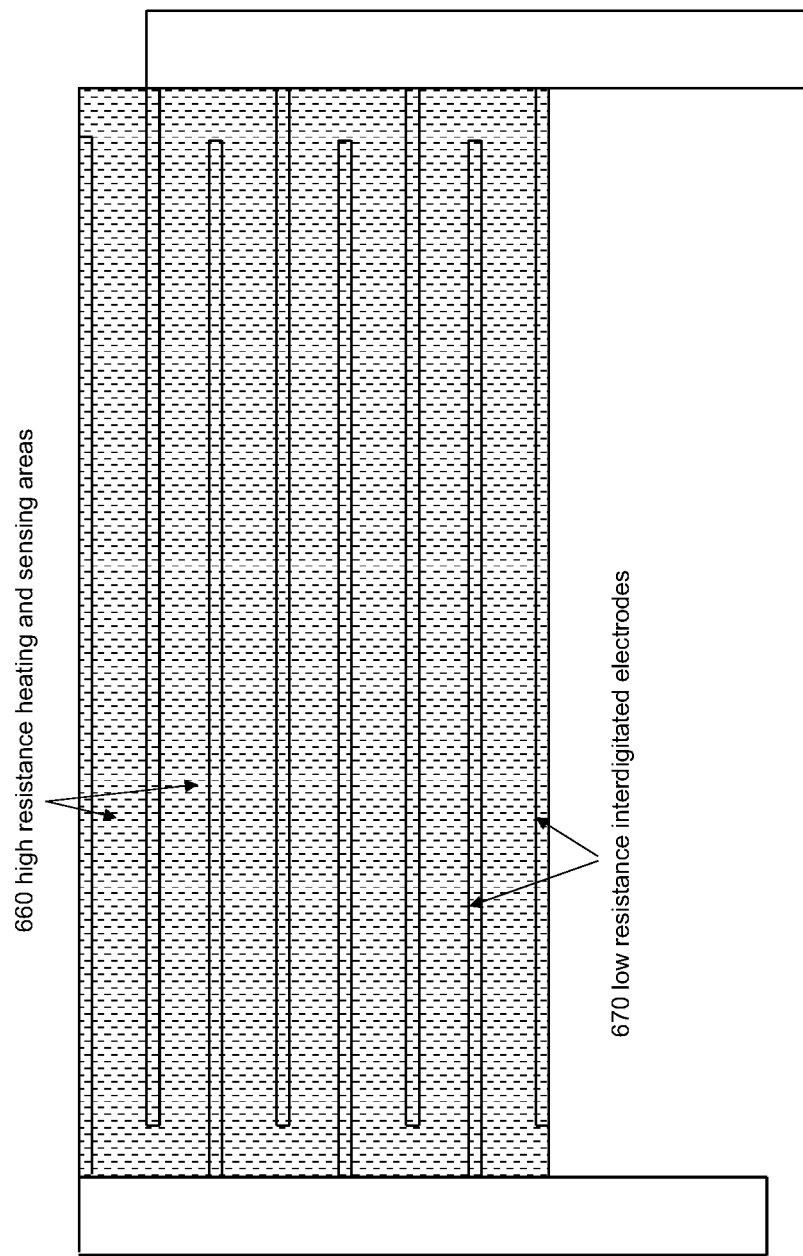
FIG. 30 shows heater element employed in an embodiment of the invention using combination of low resistance interdigitated electrodes and high resistance areas for heating and temperature sensing.

FIG. 30 shows a heater element employed in an embodiment of the invention using a combination of low resistance interdigitated electrodes and high resistance areas for heating and temperature sensing. The high resistance areas could be fabricated using a metal oxide material such as Vanadium Oxide with a large temperature coefficient of resistance (TCR) in the temperature range of interest, and the low resistance interdigitated electrodes could be fabricated using a thin film of a metal such as gold, aluminium or copper with lower sheet resistance than the high resistance heating and sensing areas.

Figure 31:
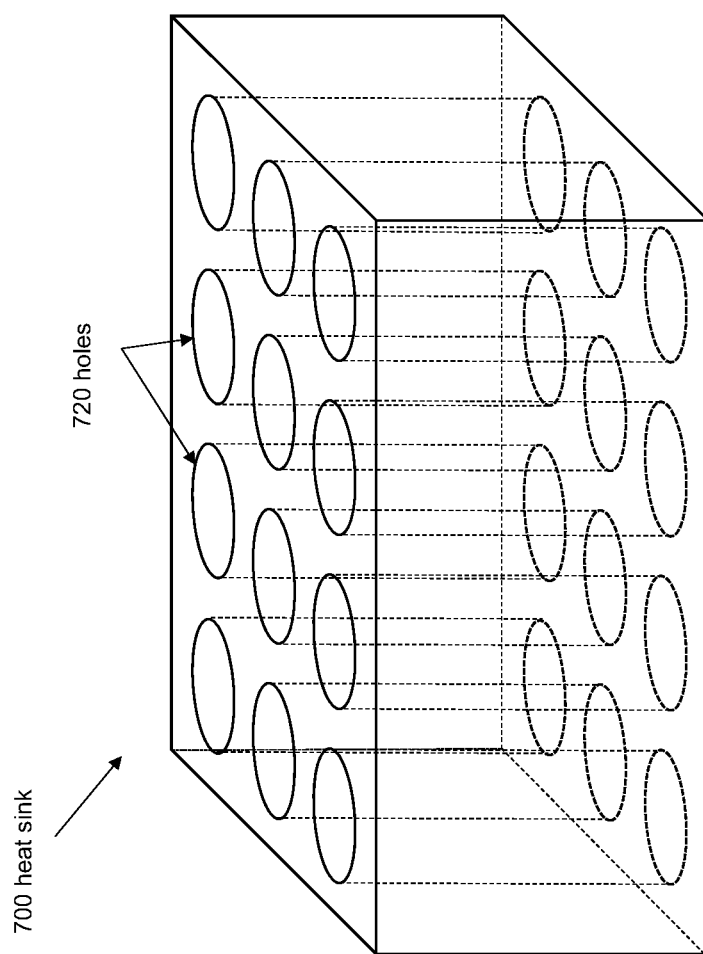
FIG. 31 shows a heat sink that can be employed with the invention.

FIG. 31 shows a heat sink employed in an embodiment of the invention perforated with holes to allow optical monitoring of a reaction, when used in combination with a partially transparent heater element. The diameter and pitch of the holes are chosen to be small enough not to disturb the temperature uniformity of the reaction cell. A typical example uses holes with dimeter 1 mm on a 2 mm pitch in an aluminium heat sink block with a thickness of 2 mm. This arrangement allows optical monitoring of a reaction even in the case where the reactor has heaters and heat sinks on both sides.

Figure 32A:
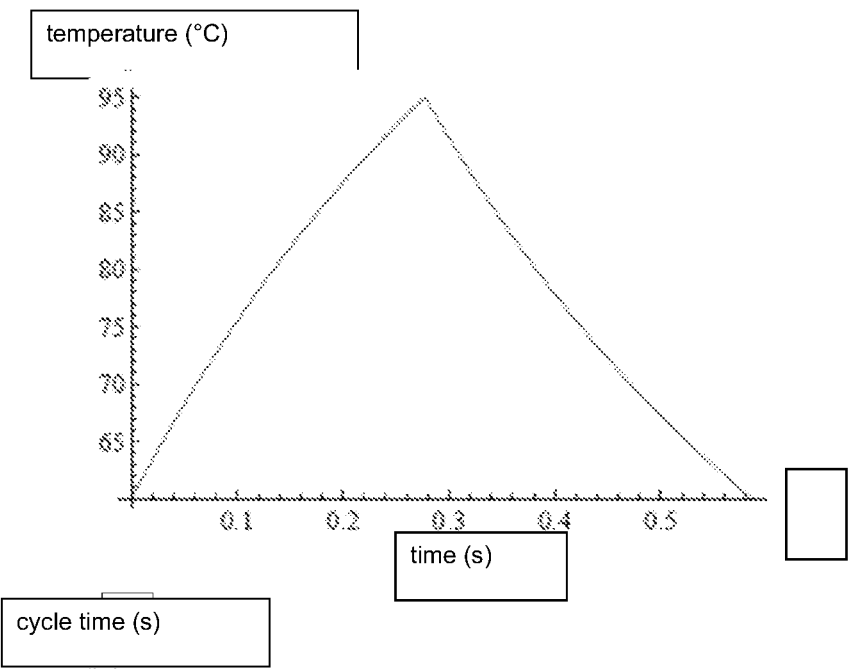
FIGS. 32A and 32B show variation of temperature with time for a heater connected to a heat sink via a thermal resistance.
Figure 32B:
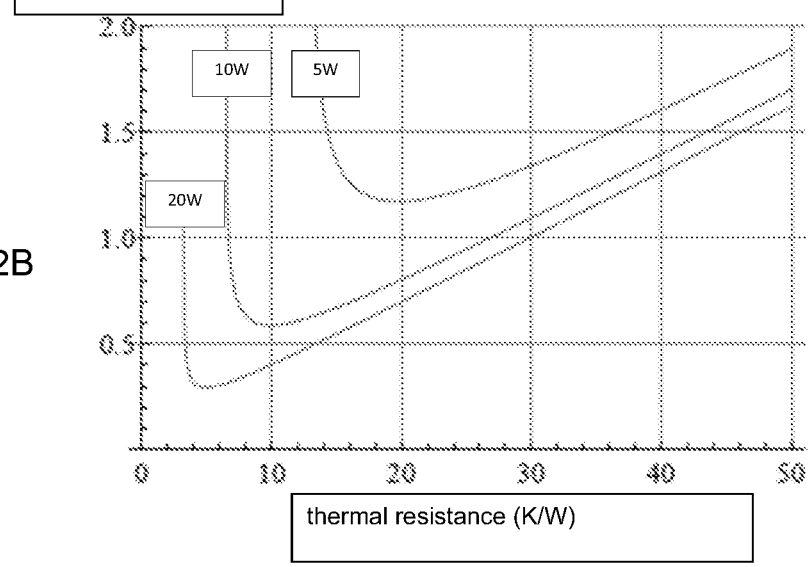

FIG. 32 shows variation of temperature with time for a heater connected to a heat sink via a thermal resistance (A) in accordance with the invention. The heater is driven at a fixed power of 10 W until the upper setpoint temperature is reached (time=0.26 s), when the heater power is reduced to zero until the lower setpoint temperature is reached (time=0.59 s). For a given heater power and heater geometry, there is a thermal resistance which minimises the thermal cycling time, shown in (B). In the case of the 10W heater, the optimum thermal resistance is approximately 10K/W. A higher power heater requires a lower thermal resistance for minimised thermal cycling time, and a lower power heater requires a higher thermal resistance for minimised thermal cycling time. For example, a 5W heater requires 20K/W thermal resistance, and a 20W heater requires 5K/W.

Figure 33:
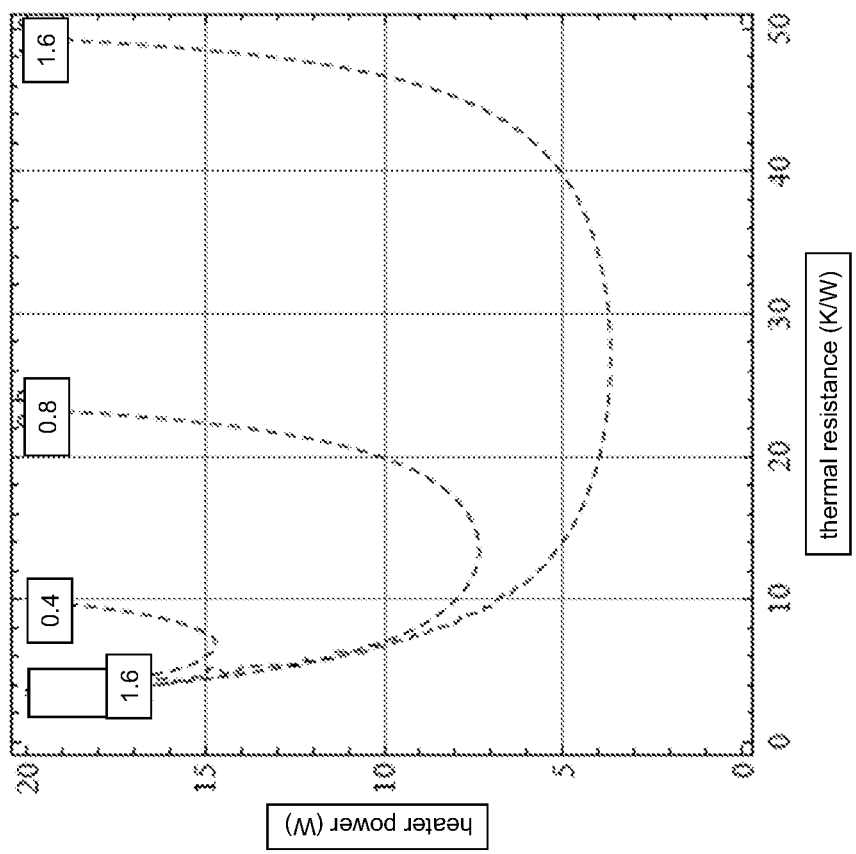
FIG. 33 shows the variation of heater power and thermal resistance for thermal cycling times in an example reactor according to the invention.

FIG. 33 shows the variation of heater power and thermal resistance for thermal cycling times of 0.4 s, 0.8 s and 1.6 s in an example reactor according to the invention. For a fixed thermal cycling time, there is an optimum thermal resistance which minimises the heater power required.

Figure 34:
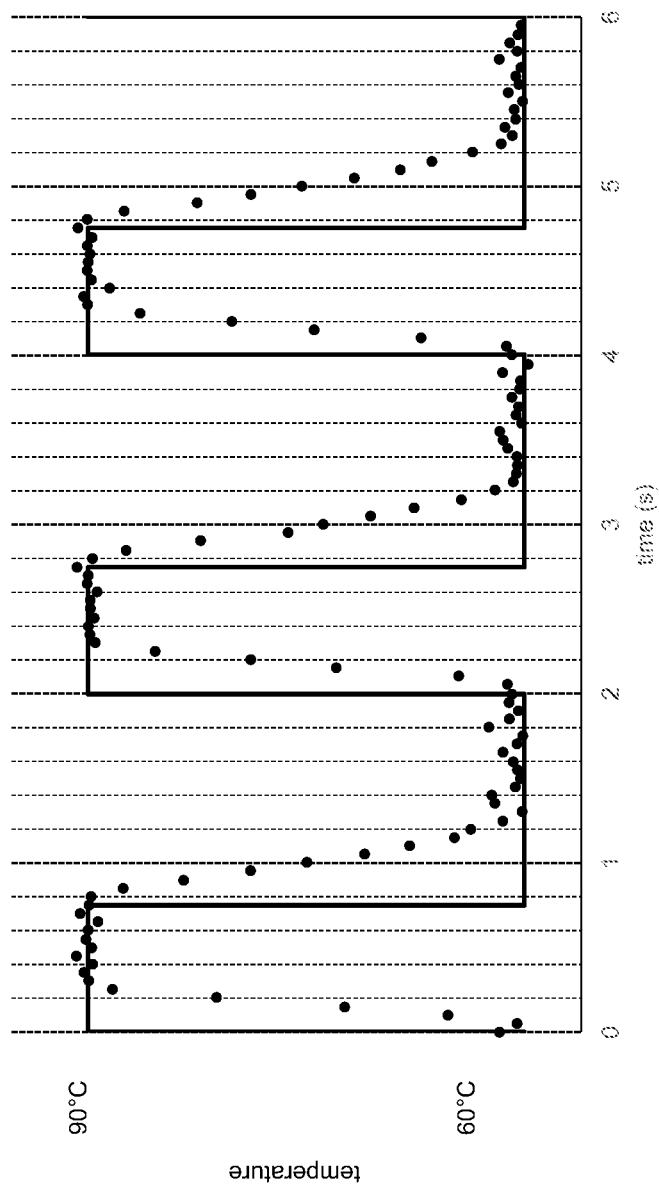
FIG. 34 shows the temperature variation over time for a heater employed in an embodiment of the invention.

FIG. 34 shows the temperature variation over time for a heater employed in an embodiment of the invention driven between 90° C. and 60° C. The thermal cycling time is 2 s. The solid line shows the temperature setpoint and the dotted lines show temperature measurements.

Figure 35A:
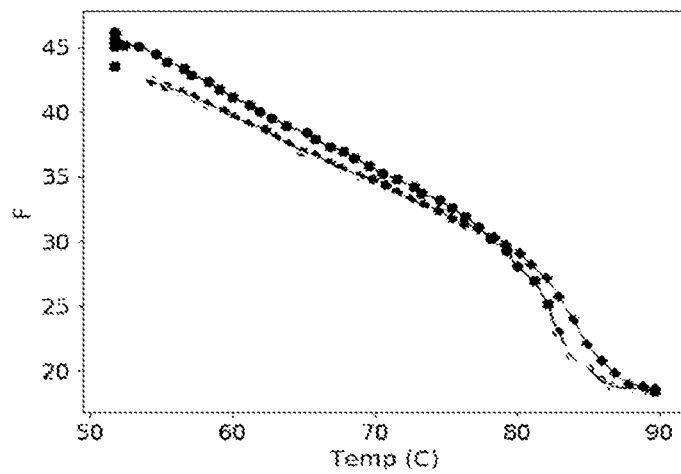
FIGS. 35A and 35B show a DNA melt curve data obtained using the reactor of an embodiment of the invention.
Figure 35B:
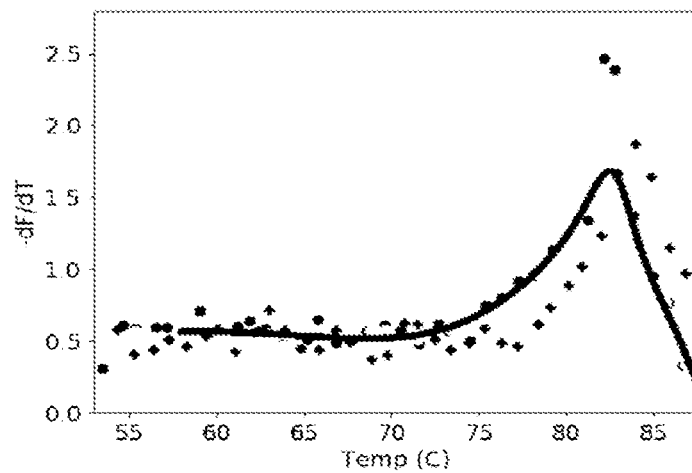

FIG. 35 shows a DNA melt curve data obtained using the reactor of an embodiment of the invention. The presence of double-stranded DNA is indicated using an intercalating dye SYBR-GREEN which shows a sudden reduction in fluorescence as the temperature rises above the melting temperature of the DNA, in this case around 83° C. The variation of fluorescence with temperature is shown in A and the gradient—dF/dT is shown in B.

Figure 36:
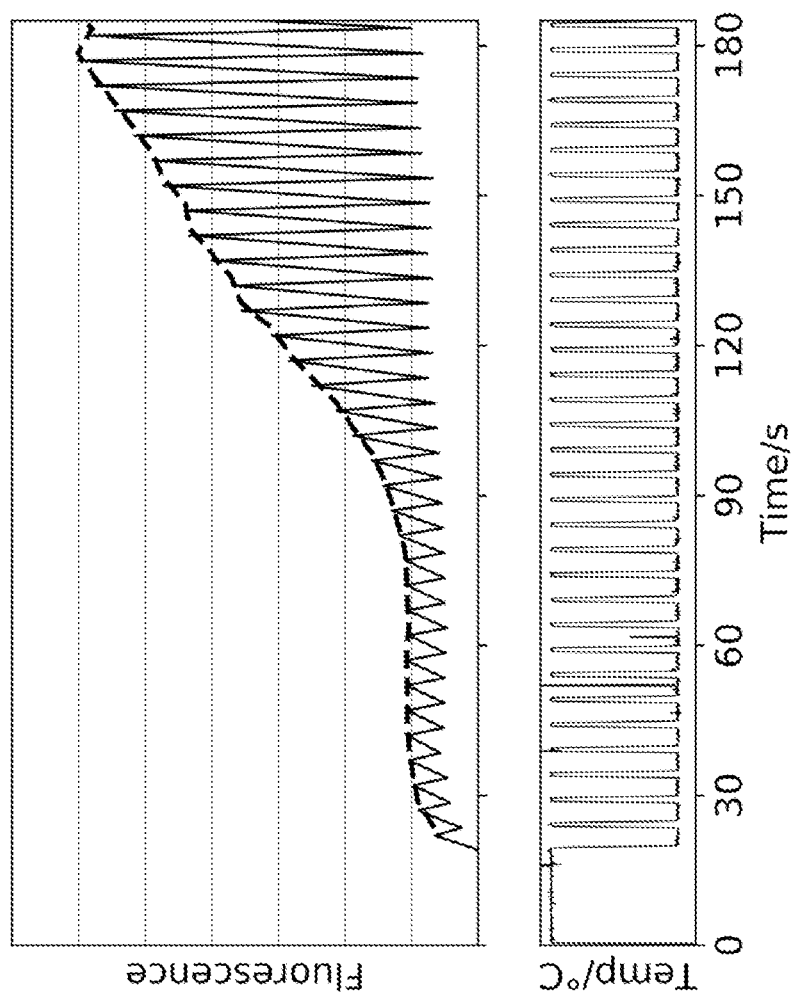
FIG. 36 shows a DNA amplification curve data for thermocycled PCR amplification using the reactor of an embodiment of the invention.

FIG. 36 shows a DNA amplification curve data for thermocycled PCR amplification using the reactor of an embodiment of the invention. The upper graph shows fluorescence of an intercalating dye against time, showing growth of DNA concentration above the background level at approximately 120 s. The lower graph shows temperature against time. An initial hot-start is used to activate the polymerase enzyme, following which a 5 s thermocycling time is used with high and low temperatures of 95° C. and 60° C.

Figure 37A:
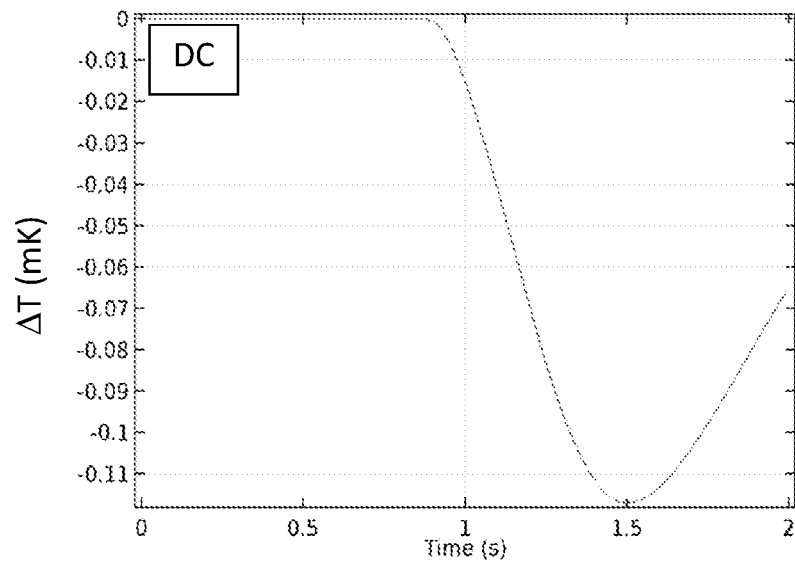
FIGS. 37A and 37B show the temperature differences between a sample and reference cell used to carry out calorimetric detection of DNA melting in an embodiment of the invention.
Figure 37B:
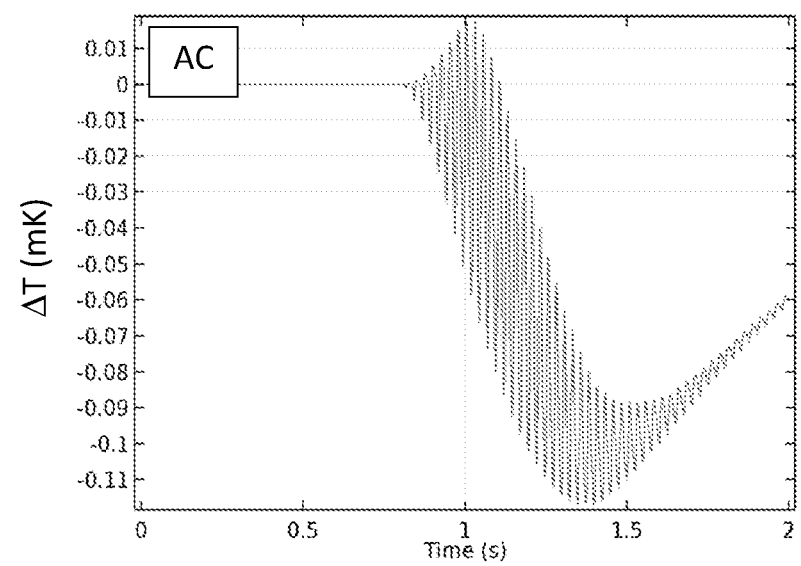

FIG. 37 shows the temperature difference between a sample and a reference cell used to carry out calorimetric detection of DNA melting in an embodiment of the invention. The sample cell contains a DNA concentration of 1 µM and the reference cell contains no DNA. The increase in heat capacity due to the DNA melting causes a depression in the temperature when the sample and reference cells are driven with equal power. A direct current drive is shown in A while an alternating current drive is shown in B. The alternating current drive gives an temperature oscillation at twice the drive frequency when the DNA is undergoing the melting transition. Electrical detection of the signal generated by the alternating current drive may be easier to detect than the direct current drive. The frequency of the alternating current drive is chosen to give a heating period approximately equal to the time for thermal diffusion through the height of the reactor. The heating period is equal to ¼ of the cycle time of a sinusoidal drive.

Figure 38:
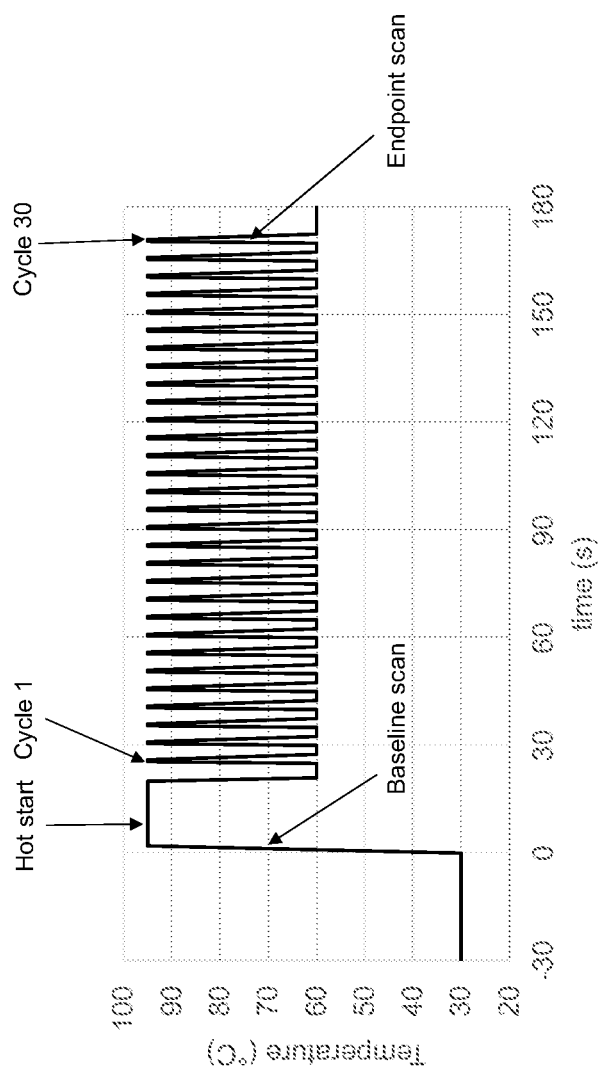
FIG. 38 shows the temperature profile of a PCR amplification scheme in a method employing the invention.

FIG. 38 shows the temperature profile of a PCR amplification scheme in a method employing the invention with a 20 s hot start period followed by a 5 s thermal cycle repeated 30 times. Differential scanning calorimetry is used to detect the amplified DNA as follows: a baseline differential temperature scan (recording the temperature difference between sample and reference cells against temperature) is measured during the temperature ramp of the hot start period. An endpoint temperature scan is made during the temperature ramp of the last PCR cycle. The difference between the baseline and endpoint scans is proportional to the heat of melting of the DNA.

Figure 39:
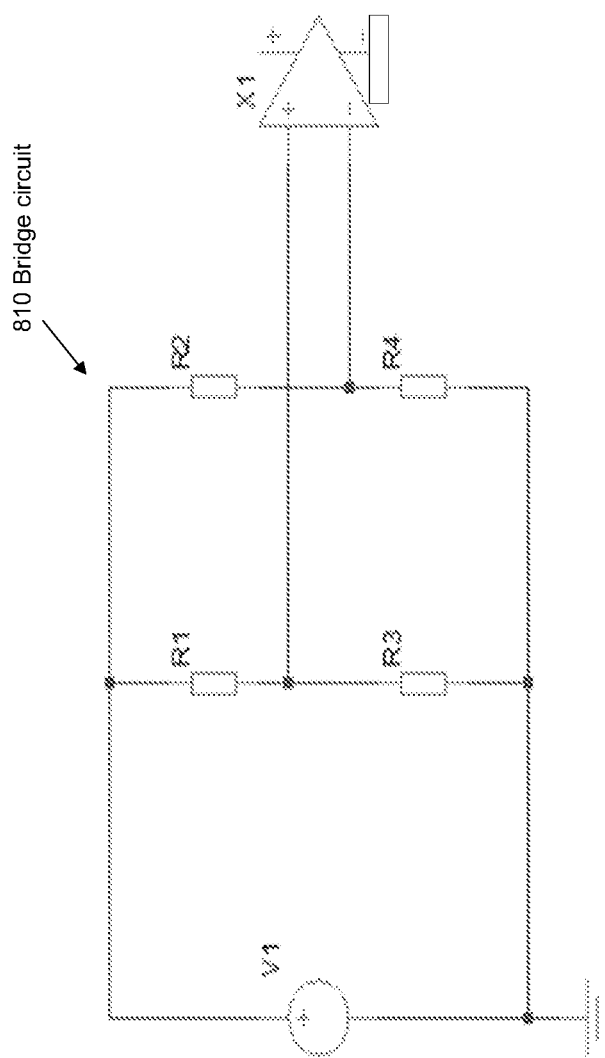
FIGS. 39, 40 and 41 show circuits according to the invention.

FIG. 39 shows a bridge circuit according to the invention for calorimetric detection of DNA melting. A sample cell is heated by resistors R1 and R4, while a reference cell is heated by resistors R2 and R3. In the case of DNA melting, the sample cell will have a lower temperature and the resistance values of R1 and R4 will be reduced, generating a higher voltage at the positive (non-inverting) input of amplifier X1 and a lower voltage at the negative (inverting) input of the amplifier X1. This results in a positive output from X1. In this case a direct current drive V1 is shown, but an alternating current drive could also be used. In the case of a sinusoidal alternating current drive, a frequency selective detection scheme can be used to detect signals only at twice the drive frequency. In the case of a square wave drive (pulsed +V or 0V), frequency-selective detection can be used detect signals at the same frequency as the drive frequency. It is desirable for the heater resistors to have a large temperature coefficient of resistance in order to generate a measurable signal voltage from a small temperature difference. In an alternative approach, thermocouples connected between the sample and reference cells generate a signal voltage proportional to the temperature difference between the cells.

Figure 40:
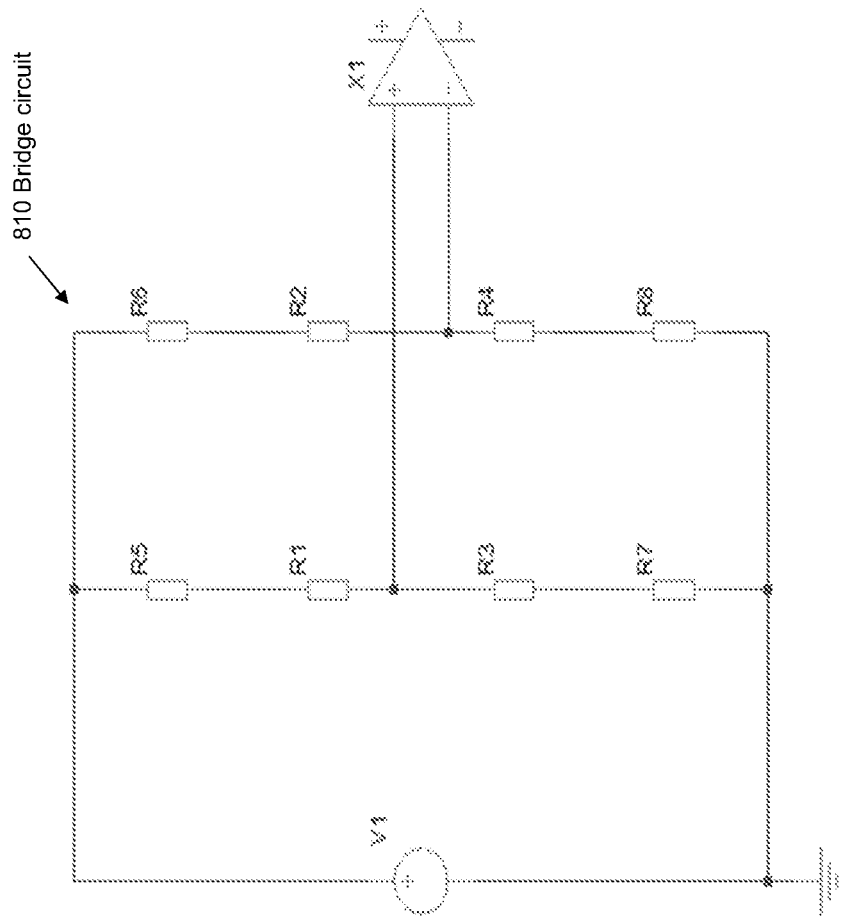

FIG. 40 shows a balancing circuit according to the invention using additional series resistors R5, R6, R7, and R8 to minimise the differential voltage output of the bridge circuit and to minimise the differences in power output of the sample heater comprising R1 and R4 and the reference heater comprising R2 and R3. The values of R5, R6, R7 and R8 can be set on manufacture or can be adjusted before detection. It is desirable to minimise the bridge circuit voltage imbalance to enable high amplification gain and sensitive detection without saturating X1. Equal power input to the sample and reference cells is desirable to ensure that both cells reach the DNA melting temperature at the same time, giving a signal proportional to the difference in DNA concentration between the two cells.

Figure 41:
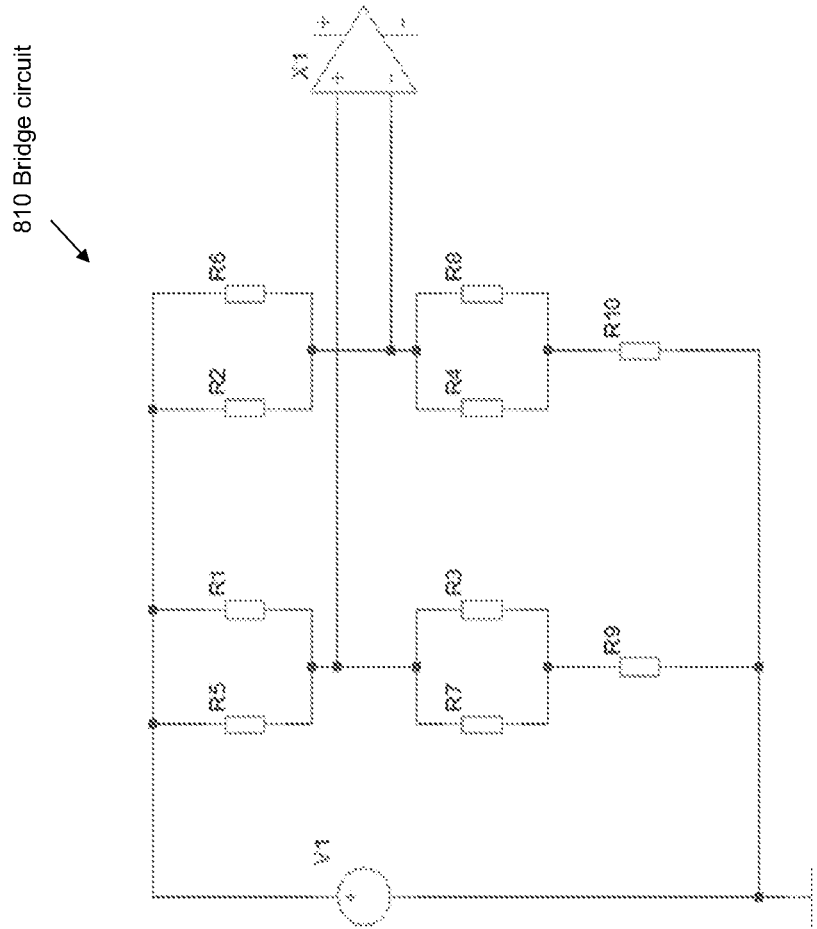

FIG. 41 shows additional parallel resistors R5, R6, R7, and R8 that may be employed with the invention to minimise the differential voltage output of the bridge circuit and to minimise the differences in power output of the sample heater and the reference heater.

As will be appreciated by a person skilled in the art, we describe a number of example reactor, heater and circuit structures in accordance with the invention that can be used in combination with any of the other examples described to achieve the invention.

The subject-matter of the application further includes the following numbered clauses.

1. A variable-temperature reactor for hosting a predetermined reaction therein, the reactor comprising a reaction cell, a heater, and a heat sink, wherein the reaction cell has a reaction volume with thickness $H_V$ and width $W_V$ where $W_V > 4 H_V$ and is defined by faces with one of the larger area faces of the reaction volume being bounded by an outer wall with thickness $H_W$;

wherein the heater is in contact with the said outer wall, where the heater comprises a heat-generating heater element located on the face closer to the reaction volume and a heater support on the opposite face, the heater support being in contact with a heat sink, such that the heater support provides a thermal resistance $R_T$ between the heater element and the heat sink, where the reactor, when filled with reagents having thermal diffusion coefficient $D_V$ has a diffusion time $t_V$, in the thickness direction, $t_V = H_V^2/D_V$ and in $t_V$ is less than the reaction time constant $t_R$, and wherein the outer wall has a thermal diffusion coefficient $D_W$ and has a thermal diffusion time $t_W = H_W^2/D_W < t_V$.

2. The reactor of clause 1, wherein the heater element functions both as a heater and as a temperature sensor.

3. The reactor of clause 1 or clause 2, further comprising a controller, wherein the heater is connected to the controller and is controlled by the controller to vary the temperature of the reactor between a higher temperature $T_{High}$ and a lower temperature $T_{Low}$, both temperatures being above the temperature of the heat sink $T_{Sink}$.

4. The reactor of any of clauses 1 to 3, where the reaction volume thickness, $H_V$, is less than 250 microns.

5. The reactor of any preceding clause, wherein the reaction cell contains a reaction volume with width $W_V$ and length $L_V$ formed by a serpentine channel located within an area having width $W_V$ and length $L_V$.

6. The reactor of any preceding clause where the reaction volume is bounded on both of its large area faces by outer walls with thickness $H_W$, with heaters in contact with both said outer walls, and with heat sinks in contact with both heaters.

7. The reactor of any preceding clause where the heater element is a resistive heating element.

8. The reactor of any preceding clause where the heater element is fabricated from an electrically conductive material and the heater support is fabricated from an electrically insulating material.

9. The reactor of any preceding clause where the heater support is formed from a softer and more flexible layer which is in contact with a harder and more rigid heat sink layer.

10. The reactor of clause 9 where the heater support is further formed from a harder and more rigid layer in contact with the softer and more flexible layer, where the softer and more flexible layer is in contact with the heat sink layer.

11. The reactor of any preceding clause where the reaction cell is separable from the heater.

12. The reactor of any preceding clause where the heater is separable from the heat sink.

13. The reactor of any preceding clause where the heat sink is cooled by forced air cooling or circulating liquid cooling or spray cooling or a heat pipe or active cooling with a Peltier element or heat pump.

14. The reactor of any preceding clause, wherein the reaction cell has an inlet channel and an outlet channel connecting fluid inlet and outlet ports to the reaction volume.

15. The reactor of any preceding clause, wherein the reaction cell comprises liquid-contact material which is an inert polymer.

16. The reactor of any preceding clause, arranged such that the thermal resistance $R_T$ between the heater element and the heat sink is chosen to satisfy the following relationships:

$$R_T > (T_{HIGH} - T_{Sink})/p_{Heat} \text{ and}$$

$$0.5 R_{T,Opt} < R_T < 2 R_{T,Opt}$$

where $R_{T,Opt} = (T_{HIGH} + T_{LOW} - 2 T_{Sink})/p_{Heat}$, and the reactor is arranged to cycle repeatedly between a lower temperature $T_{LOW}$ and a higher temperature $T_{HIGH}$ using a heater with power output $p_{Heat}$ and a heat sink at a temperature $T_{Sink}$.

17. The reactor of any preceding clause, arranged such that the thermal resistance of the heater support $R_T$ and the sum of the heat capacity of the filled reaction volume and the heat capacity of the part of the thin outer wall located between the reaction volume and the heater element, $C_V$ satisfy the relationship $R_T C_V < t_R$, where $t_R$ is the time constant for the reaction.

18. The reactor of any preceding clause, arranged such that the sum of the heat capacity of the filled reaction volume and the heat capacity of the part of the thin outer wall located between the reaction volume and the heater element, $C_V$, and the heat capacity of the heat sink, $C_S$, satisfy the relationship: $C_S/C_V > 100$.

19. The reactor of any preceding clause, wherein the thermal conductivity of the heat sink material is more than 10 times the thermal conductivity of the heater support material.

20. The reactor of any preceding clause, wherein the heat capacity of the part of the thin outer wall and heater located between the reaction volume and the heat sink is lower than the heat capacity of liquid within the reaction volume.

21. The reactor of any preceding clause, wherein the thermal effusivity of the heat sink material is more than 10 times the thermal effusivity of the heater support material, where thermal effusivity e is a function of the material's thermal conductivity k, density $\rho$ and specific heat capacity $c_p$ and is defined as $e = \sqrt{k \rho c_p}$.

22. The reactor of any preceding clause, wherein the heater element extends across the full area of the reaction volume.

23. The reactor of any preceding clause, wherein the heater element is resistive and has a rectangular or square shape.

24. The reactor of any preceding clause, wherein the heater element is fabricated from an electrically conductive material with absolute value of temperature coefficient of resistance greater than 500 ppm/K across the operating temperature range of the heater.

25. The reactor of any preceding clause, wherein the heater element is fabricated from an electrically conductive material with absolute value of temperature coefficient of resistance greater than 2,500 ppm/K across the operating temperature range of the heater.

26. The reactor of any preceding clause, wherein the heater element is fabricated from an electrically conductive material with absolute value of temperature coefficient of resistance greater than 10.00 ppm/K across the operating temperature range of the heater.

27. The reactor of any preceding clause, wherein the heater element is fabricated by evaporating or sputtering or printing or laminating or lithographically patterning or laser-patterning the electrically conductive material.

28. The reactor of any preceding clause, wherein the heater element is fabricated from an electrically conductive material with a positive TCR, and may comprise one of Pt, Ti, Al, Mo, Ni, Cu, Au.

29. The reactor of any preceding clause, wherein the resistive heating element is fabricated from a material with a negative TCR, such as a metal oxide which undergoes a transition from being electrically insulating to electrically conducting as temperature rises, such as Vanadium Oxide.

30. The reactor of any preceding clause, wherein electrical contacts are provided on opposite corners of the heater element and the current is distributed along opposite edges of the heater element by electrically conducting tracks with tapered width, reducing from a larger width at the electrical contact corners to a narrower width at the distal side of the electrical contact edge.

31. The reactor of any preceding clause, wherein the heater comprises Kelvin contacts for electrical resistance measurements.

32. The reactor of any preceding clause, wherein the heater element is arranged to have higher heat output per unit area near its perimeter than near its centre.

33. The reactor of clause 32, wherein the heater element has a square or rectangular form with electrical contacts along two opposite edges with higher sheet resistance regions at the electrical contact edges and lower sheet resistance regions at the other two edges.

34. The reactor of any preceding clause, wherein the heater element comprises a main heater surrounded by one or more guard heaters.

35. The reactor of clause 34, comprising means to control the temperature of the guard heaters to the same temperature setpoint as the main heater.

36. The reactor of clause 34 or 35, wherein the guard heaters have lower sheet resistance than the main heater.

37. The reactor of any of clauses 34 to 36, wherein the main heater is elongate in the direction of current flow and where guard heaters are placed adjacent to the long sides of the main heater.

38. The reactor of any preceding clause, wherein the sheet resistance of the heater element is locally increased in end zones located on the heater element edges perpendicular to the direction of current flow.

39. The reactor of any preceding clause, wherein the sheet resistance of the heater element is locally decreased in side zones located on the heater element edges parallel to the direction of current flow.

40. The reactor of clause 38, wherein the increased sheet resistance in the heater element is provided by partial coverage of an electrically conductive material, for example by forming a layer of an electrically conductive material perforated by array of holes or slots.

41. The reactor of any preceding clause, wherein the heater support or heat sink comprise thermal breaks located near the perimeter of the heater element and between the heater element and the heat sink.

42. The reactor of any preceding clause, wherein the reaction volume is arranged to contain, in use, reagents used for polymerase chain reaction (PCR) amplification of nucleic acid sequences.

43. The reactor of any of clauses 1 to 41, wherein the reactor is configured to carry out DNA amplification by polymerase chain reaction (PCR) thermocycling.

44. The reactor of any preceding clause, wherein the reactor comprises a controller configured to control temperature with different temperature setpoints for different reaction steps in a multi-step reaction.

45. The reactor of clause 44, wherein the reactor is configured to carry out a multi-step reaction for DNA sequencing.

46. The reactor of any preceding clause, wherein the heat sink comprises holes to allow optical inspection of the reaction volume.

47. The reactor of any preceding clause, arranged such that the result of the reaction in the reaction volume is detected using fluorescence or colorimetric or UV absorption or electrochemical or calorimetric or electrophoresis or oligonucleotide sensing.

48. The reactor of any preceding clause, arranged such that the reaction output is detected by monitoring the evolution of a reaction measurement over multiple thermal cycles.

49. The reactor of any preceding clause, wherein reaction sensors are located within the outer wall of the reaction volume or in are contact with the outer wall of the reaction volume.

50. The reactor of any preceding clause, configured for calorimetric detection of the result of the reaction by comprising a measurement component for measuring a change in the heat capacity of a sample in the reactor.

51. The reactor of any preceding clause, wherein the reactor is configured for DTA or DSC by being structured to use a sample reaction and a reference reaction.

52. The reactor of any of clauses 1 to 50, configured for DTA or DSC with baseline correction by comprising means for subtracting a first temperature scan from a second temperature scan measured at a different time.

53. The reactor of any preceding clause, configured for label-free detection of the result of the reaction.

54. The reactor of clause 51, configured such that measurement is made while heating the sample and reference reaction volumes.

55. The reactor of any preceding clause, arranged to handle reaction product which is DNA or RNA and arranged so that melting of the reaction product is detected calorimetrically.

56. The reactor of clause 51 or 54, arranged such that a first DTA or DSC measurement is carried out while ramping the temperature of a sample and a reference for the hot start phase preceding thermocycling for PCR amplification of DNA and a second DTA or DSC measurement is carried out following thermocycling for PCR amplification of DNA.

57. A plurality of reactors of any preceding clause, wherein at least one reaction volume contains a sample material and at least one reaction volume contains a reference material in use.

58. The reactor of any preceding clause, wherein the heater element has a driver arranged to provide the heater with a pulsed or oscillating heat output.

59. The reactor of any preceding clause, wherein the reaction volume with height $H_V$ and contents with thermal diffusivity $D_V$ and thin reaction chamber wall with thickness $H_W$ and with thermal diffusivity $D_W$ are arranged to be heated by a heater on one side only where the frequency of the heater drive satisfies the relationship:

$$\frac{1}{2\pi} \frac{D_W}{H_W^2} \geq f_{DRIVE} \geq \frac{1}{2\pi} \frac{D_V}{H_V^2}$$

60. The reactor of any preceding clause, wherein the reaction volume with height $H_V$ and contents with thermal diffusivity $D_V$ and thin reaction chamber wall with thickness $H_W$ and with thermal diffusivity $D_W$ are arranged to be heated by heaters on both sides where the frequency of the heater drive satisfies the relationship:

$$\frac{1}{2\pi}\frac{D_W}{H_W^2} \geq f_{DRIVE} \geq \frac{4}{2\pi}\frac{D_V}{H_V^2}$$

61. The reactor of any preceding clause, further comprising a resistive heater element which is driven with a sinusoidal waveform at a drive frequency and comprising means for measuring the temperature of the heater element by measuring variations in heater element resistance at a frequency of 2× the drive frequency, or by measuring variations in the heater voltage or current at 3× the drive frequency.

62. The reactor of any preceding clause, wherein the temperature difference between a sample and reference is sensed using a sample resistive heater and a reference resistive heater and two fixed resistors arranged in a bridge circuit.

63. The reactor of any of clauses 1 to 61, wherein the temperature difference between a sample and a reference is sensed using two sample resistive heaters and two reference resistive heaters arranged in a bridge circuit, where each side of the bridge circuit contains one resistive heater from each of the sample and reference vessels.

64. The reactor of clause 62 or 63, wherein trim resistors are used to balance simultaneously the bridge circuit output voltage and the heater power applied to the sample and reference vessels.

65. The reactor of any preceding clause, wherein the heater element comprises holes to allow optical inspection of the reaction volume.

66. The reactor of any preceding clause, wherein the heater element is formed with holes or slots or gaps or a serpentine path that enables light transmission and optical monitoring of the reaction.

67. The reactor of any preceding clause, wherein the heater element is formed from a transparent conductive material such as ITO or graphene or nanowire materials.

68. The reactor of any preceding clause, wherein the reaction volume contains a plurality of spatially separated zones with different reagents located in different zones of the reaction volume, and with the zone spacing greater than the greater of the mass diffusion length of the reaction products and mass diffusion length of the reagents on the timescale of the reaction time constant, $t_R$, and different reactions are monitored independently within each reaction zone.

69. The reactor of clause 68, further comprising means to thermally cycle the reaction volume N times with cycle time $t_C$ and the reagent pitch is greater than the mass diffusion length of the reaction products and reagents for a diffusion time equal to N multiplied by $t_C$.

70. The reactor of any clause 68 or 69, where when the same reagents are located in each zone of the reaction volume in use, means is provided to independently monitor each zone to detect presence or absence of a reaction products within each zone.

71. The reactor of any of clauses 68 to 70, further comprising a processor for processing the statistics of the number of zones containing reaction products and not containing reaction products to calculate the concentration of an analyte in use.

72. The reactor of any of clauses 68 to 71, where there are at least 100 reaction zones within the reaction volume, or where there are at least 1,000 reaction zones within the reaction volume, or where there are at least 10,000 reaction zones within the reaction volume.

73. The reactor of any of clauses 68 to 72, where the reaction volume is divided into reaction zones connected by diffusion restricting channels with cross-sectional area <0.25 of the cross-sectional area of the reaction zones, and where the diffusion restriction channels have length >0.25 of the width of the reaction zones.

74. A heater for a variable temperature reactor, the heater comprising a heating element, wherein the heating element functions both as a heater and as a temperature sensor.

75. The heater of clause 74, wherein the heater element is resistive and has a rectangular or square shape.

76. The heater of clause 74 or 75, wherein the heater element is fabricated from an electrically conductive material with absolute value of temperature coefficient of resistance greater than 500 ppm/K across the operating temperature range of the heater.

77. The heater of any of clauses 74 to 76, wherein the heater element is fabricated from an electrically conductive material with absolute value of temperature coefficient of resistance greater than 2,500 ppm/K across the operating temperature range of the heater.

78. The heater of any of clauses 74 to 77, wherein the heater element is fabricated from an electrically conductive material with absolute value of temperature coefficient of resistance greater than 10.00 ppm/K across the operating temperature range of the heater.

79. The heater of any of clauses 74 to 78, wherein the heater element is fabricated by evaporating or sputtering or printing or laminating or lithographically patterning or laser-patterning the electrically conductive material.

80. The heater of any of clauses 74 to 79, wherein the heater element is fabricated from an electrically conductive material with a positive TCR, and may comprise one of Pt, Ti, Al, Mo, Ni, Cu, Au.

81. The heater of any of clauses 74 to 80, wherein the resistive heating element is fabricated from a material with a negative TCR, such as a metal oxide which undergoes a transition from being electrically insulating to electrically conducting as temperature rises, such as Vanadium Oxide.

82. The heater of any of clauses 74 to 81, wherein electrical contacts are provided on opposite corners of the heater element and the current is distributed along opposite edges of the heater element by electrically conducting tracks with tapered width, reducing from a larger width at the electrical contact corners to a narrower width at the distal side of the electrical contact edge.

83. The heater of any of clauses 74 to 82, wherein the heater comprises Kelvin contacts for electrical resistance measurements.

84. The heater of any of clauses 74 to 83, wherein the heater element is arranged to have higher heat output per unit area near its perimeter than near its centre.

85. The heater of clause 84, wherein the heater element has a square or rectangular form with electrical contacts along two opposite edges with higher sheet resistance regions at the electrical contact edges and lower sheet resistance regions at the other two edges.

86. The heater of any of clauses 74 to 85, wherein the heater element comprises a main heater surrounded by one or more guard heaters.

87. The heater of clause 86, comprising means to control the temperature of the guard heaters to the same temperature setpoint as the main heater.

88. The heater of clause 86 or 87, wherein the guard heaters have lower sheet resistance than the main heater.

89. The heater of any of clauses 86 to 88, wherein the main heater is elongate in the direction of current flow and where guard heaters are placed adjacent to the long sides of the main heater.

90. The heater of any of clauses 74 to 89, wherein the sheet resistance of the heater element is locally increased in end zones located on the heater element edges perpendicular to the direction of current flow.

91. The heater of any of clauses 74 to 90, wherein the sheet resistance of the heater element is locally decreased in side zones located on the heater element edges parallel to the direction of current flow.

92. The heater of clause 91, wherein the increased sheet resistance in the heater element is provided by partial coverage of an electrically conductive material, for example by forming a layer of an electrically conductive material perforated by array of holes or slots.

93. A driving and sensing circuit for a variable temperature reactor, the circuit comprising means for providing power to a sample resistive heater and a reference resistive heater and means for sensing the temperature difference between a sample and reference by monitoring the sample resistive heater and the reference resistive heater and two fixed resistors arranged in a bridge circuit.

94. A driving and sensing circuit for a variable temperature reactor, the circuit comprising means for providing power to two sample resistive heaters and two reference resistive heaters arranged in a bridge circuit, and means for measuring the temperature difference between a sample and a reference by monitoring the two sample resistive heaters and two reference resistive heaters, where each side of the bridge circuit is arranged such that, in use, it contains one resistive heater from each of a sample and reference vessel.

95. The circuit of clause 93 or 94, further comprising trim resistors to balance simultaneously the bridge circuit output voltage and the heater power applied to the sample and reference vessels.

96. A method of operating the reactor, heater and circuit of any preceding clause to provide measurements from a variable temperature reaction.

The invention claimed is:

1. A variable-temperature reactor for hosting a reaction therein, the reactor comprising:
    (a) a reaction cell comprising:
        one or more side walls,
        a first thin outer wall arranged in contact with a first end of the one or more side walls, and
        either a cover or a second thin outer wall arranged in contact with a second end of the one or more side walls and arranged substantially in parallel with the first thin outer wall,
        wherein the one or more side walls, the first thin outer wall, and the cover or the second thin outer wall enclose one or more flat reaction volumes each having a width and a thickness,
        wherein the flat reaction volume width is greater than four times the flat reaction volume thickness in each of the one or more flat reaction volumes,
        wherein the flat reaction volume thickness in each of the one or more flat reaction volumes is about 100 microns to about 250 microns, and
        wherein the first thin outer wall has a thickness of less than about 76 microns and a thermal diffusion coefficient selected to provide a thin outer wall thermal diffusion time of less than about one second;
    (b) a heater comprising:
        a heater element arranged in contact with the first thin outer wall of the reaction cell and having a size and area sufficient to extend across a full area of each of the one or more flat reaction volumes, and
        a heater support arranged in contact with the heater element and to support the heater element on a side opposite to the first thin outer wall; and
    (c) a heat sink in contact with the heater support, such that the heater support provides a thermal resistance between the heater element and the heat sink.

2. The variable-temperature reactor of claim 1, wherein the first thin outer wall comprises an inert polymer.

3. The variable-temperature reactor of claim 2, wherein the inert polymer comprises polypropylene.

4. The variable-temperature reactor of claim 1, wherein the first thin outer wall thermal diffusion time is less than a flat reaction volume thermal diffusion time.

5. The variable-temperature reactor of claim 4, wherein the flat reaction volume thermal diffusion time is equal to a square of the flat reaction volume thickness divided by a reagent thermal diffusion coefficient, and wherein the first thin outer wall thermal diffusion time is equal to a square of the first thin outer wall thickness divided by the outer wall thermal diffusion coefficient.

6. The variable-temperature reactor of claim 5, wherein the reagent thermal diffusion coefficient is about the same as a thermal diffusion coefficient of water.

7. The variable-temperature reactor of claim 1, wherein:
    the first thin outer wall has a first heat capacity;
    the heater has a second heat capacity;
    reagents in the one or more flat reaction volumes have a third heat capacity; and
    a sum of the first and second heat capacities is less than ten times the third heat capacity.

8. The variable-temperature reactor of claim 7, wherein a sum of the first and second heat capacities is less than twice the third heat capacity.

9. A variable-temperature reactor of claim 1, wherein a sum of a heat capacity of a filled reaction volume and a heat capacity of a part of the first thin outer wall located between the reaction volume and the heater element is less than one percent of a heat capacity of the heat sink.

10. The variable-temperature reactor of claim 1, wherein:
    the reactor is arranged to cycle a reactor temperature repeatedly between a lower temperature and a higher temperature using the heater with a heater power output and the heat sink at a heat sink temperature, wherein both of the higher temperature and the lower temperature are above the heat sink temperature;
    a thermal resistance between the heater element and the heat sink multiplied by the heater power output is greater than a difference between the higher temperature and the heat sink temperature, and
    a thermal resistance of the heater support arranged between the heater element and the heat sink multiplied by a heater power output is between 0.5 and 2 times the sum of respective differences between the higher temperature and the heat sink temperature and between the lower temperature and the heat sink temperature.

11. The variable-temperature reactor of claim 1, wherein the heater is configured and controlled to change a reactor temperature at a temperature ramp rate of at least 70° C./second.

12. The variable-temperature reactor of claim 1, arranged such that in use a thermal resistance of the heater support multiplied by a sum of a heat capacity of reagents within the reaction cell and a heat capacity of the first thin outer wall of the reaction cell is less than a reaction time constant, wherein a heat capacity of the reagents is about the same as a heat capacity of water.

13. The variable-temperature reactor of claim 12, wherein the reaction time constant is about one second.

14. The variable-temperature reactor of claim 1, wherein the reaction cell comprises a serpentine channel as the reaction volume.

15. The variable-temperature reactor of claim 1, comprising the second thin outer wall and further comprising a second heater in contact with the second thin outer wall of the reaction cell, and a second heat sink in contact with the second heater, wherein the second thin outer wall of the reaction cell is arranged opposite the first thin outer wall of the reaction cell.

16. The variable-temperature reactor of claim 1, wherein a thermal effusivity of a material of the heat sink is more than ten times a thermal effusivity of a material of the heater support, wherein the thermal effusivity of a material is defined as a square root of a product of a thermal conductivity of the material, a density of the material, and a specific heat capacity of the material.

17. The variable-temperature reactor of claim 1, wherein the heater element comprises a main heater surrounded by one or more guard heaters to provide a higher heat output per unit area of the heater element near its perimeter than near its center.

18. The variable-temperature reactor of claim 1, wherein the heater further comprises Kelvin contacts for electrical resistance measurements.

19. The variable-temperature reactor of claim 1, further comprising a sinusoidal electrical drive controlled at a frequency $f_{DRIVE}$ that is applied to the heater element to generate an oscillating heat output at a frequency of $2 \times f_{DRIVE}$, where $f_{DRIVE}$ satisfies the condition:

$$f_{DRIVE} \leq \frac{1}{2\pi} \frac{D_W}{H_W^2}$$

wherein $D_W$ is a thermal diffusion coefficient of the thin outer wall and $H_W$ is a thickness of the thin outer wall.

20. The variable-temperature reactor of claim 19, wherein $f_{DRIVE}$ is about 23 Hz to about 2.3 Hz, and the thin outer wall has a thickness of about 24 microns to about 76 microns.

21. The variable-temperature reactor of claim 1, wherein the first thin outer wall has a thickness of about 24 microns to about 76 microns.

22. The variable-temperature reactor of claim 1, wherein the first thin outer wall has a thermal diffusion time of less than 0.07 seconds.

23. The variable-temperature reactor of claim 1, wherein the first thin outer wall has a thermal diffusion time of less than 0.007 seconds.

24. The variable-temperature reactor of claim 1, wherein the reaction cell is manufactured by an embossing and laminating process to attach the first thin outer wall to the one or more side walls of the reaction cell.

* * * * *